US011406696B2

(12) United States Patent
Feron et al.

(10) Patent No.: US 11,406,696 B2
(45) Date of Patent: Aug. 9, 2022

(54) *P AERUGINOSA* PCRV-LINKED ANTIGEN VACCINES

(71) Applicant: GLAXOSMITHKLINE BIOLOGICALS, S.A., Rixensart (BE)

(72) Inventors: Christiane Marie-Paule Simone Jeanne Feron, Rixensart (BE); Stefan Jochen Kemmler, Schlieren (CH); Michael Thomas Kowarik, Schlieren (CH); Julien Laurent Quebatte, Schlieren (CH)

(73) Assignee: GlaxoSmithKline Biologicals SA

( * ) Notice: Subject to any disclaimer, the term of this patent is extended or adjusted under 35 U.S.C. 154(b) by 214 days.

(21) Appl. No.: 15/769,646

(22) PCT Filed: Oct. 19, 2016

(86) PCT No.: PCT/EP2016/075048
§ 371 (c)(1),
(2) Date: Apr. 19, 2018

(87) PCT Pub. No.: WO2017/067964
PCT Pub. Date: Apr. 27, 2017

(65) Prior Publication Data
US 2019/0091319 A1 Mar. 28, 2019

(30) Foreign Application Priority Data
Oct. 21, 2015 (GB) .................................. 1518668

(51) Int. Cl.
| A61K 39/02 | (2006.01) |
| A61K 39/104 | (2006.01) |
| A61K 39/385 | (2006.01) |
| C07K 14/21 | (2006.01) |
| A61K 47/64 | (2017.01) |
| A61K 45/06 | (2006.01) |
| A61P 31/04 | (2006.01) |
| C12N 9/10 | (2006.01) |
| A61K 39/00 | (2006.01) |

(52) U.S. Cl.
CPC .......... *A61K 39/104* (2013.01); *A61K 39/385* (2013.01); *A61K 45/06* (2013.01); *A61K 47/646* (2017.08); *A61K 47/6415* (2017.08); *A61P 31/04* (2018.01); *C07K 14/21* (2013.01); *C12N 9/1014* (2013.01); *C12N 9/1051* (2013.01); *C12N 9/1081* (2013.01); *A61K 2039/6037* (2013.01); *A61K 2039/6068* (2013.01); *A61K 2039/6087* (2013.01); *A61K 2039/64* (2013.01); *C07K 2319/00* (2013.01); *C12Y 201/02002* (2013.01); *C12Y 204/01019* (2013.01); *C12Y 204/99* (2013.01); *Y02A 50/30* (2018.01)

(58) Field of Classification Search
USPC ..................................................... 424/200.1
See application file for complete search history.

(56) References Cited

U.S. PATENT DOCUMENTS

2015/0044215 A1* 2/2015 De Tavernier ....... C07K 16/468
424/136.1

FOREIGN PATENT DOCUMENTS

| WO | 2006/119987 A2 | 11/2006 | |
| WO | 2009/104074 A2 | 8/2009 | |
| WO | WO-2009104074 A2 * | 8/2009 | ........... C07K 14/195 |
| WO | 2014072405 A1 | 5/2014 | |
| WO | 2015/158403 A1 | 10/2015 | |
| WO | 2015158403 A1 | 10/2015 | |
| WO | 2016/020499 A2 | 2/2016 | |

OTHER PUBLICATIONS

Isar Dejban Golpasha et al: "Immunization with 3-oxododecanoyl-L-homoserine lactone-r-PcrV conjugate enhances survival of mice against lethal burn infections caused by Pseudomonas aeruginosa", Bosnian Journal of Basic Medical Sciences, vol. 15, No. 2 Mar. 2015 (Year: 2015).*
Bork (Genome Research, 2000, 10:398-400) (Year: 2000).*
Burgess et al (J. of Cell Bio. 111:2129-2138, 1990) (Year: 1990).*
Bowie et al (Science, 1990, 257:1306-1310) (Year: 1990).*
Isar Dejban et al. Bosnian Journal of Basic Medical Sciences, vol. 15, No. 2, Mar. 2, 2015 (Year: 2015).*
Cuccui, et al., "Hijacking bacterial glycosylation for the production of glycoconjugates, from vaccines to humanised glycoprotiens." Journal of Pharmacy and Pharmacology; 2014; pp. 338-350; vol. 67 (3).
Frank, et al., "Generation and Characterization of a Protective Monoclonal Antibody to Pseudomonas Aeruginosa PcRV." Journal of Infectious Diseases; 2002; pp. 64-73; vol. 186(1).
Poolman, et al., "Extraintestinal Pathogenic *Escherichia coli*, a Common Human Pathogen: Challenges for Vaccine Development and Progress in the Field." Journal of Infectious Diseases; 2015; pp. 6-13; vol. 213 (1).
Priebe, et al., "Vaccines for Pseudomonas aeruginosa: a long and winding road." Expert Review of Vaccines; 2014; pp. 507-519; vol. 13(4).
Ravenscroft, et al., "Purification and characterization of a Shigella conjugate vaccine, produced by glycoengineering *Escherichia coli*." Glycobiology; 2015; pp. cwv077.

(Continued)

*Primary Examiner* — Jana A Hines
*Assistant Examiner* — Khatol S Shahnan Shah
(74) *Attorney, Agent, or Firm* — Dana L. Broughton

(57) ABSTRACT

The present invention discloses a conjugate comprising an antigen (for example a saccharide antigen) covalently linked to a *Pseudomonas aeruginosa* PcrV carrier protein comprising an amino acid sequence which is at least 80% identical to the sequence of SEQ ID NO:1-4, wherein the antigen is linked (either directly or through a linker) to an amino acid residue of the *P. aeruginosa* PcrV carrier protein. The invention also discloses *Pseudomonas aeruginosa* PcrV proteins that contain glycosylation site consensus sequences.

6 Claims, 16 Drawing Sheets

Specification includes a Sequence Listing.

(56) References Cited

OTHER PUBLICATIONS

Raymond, et al., "Genetic variation at the O-antigen biosynthetic locus in Pseudomonas aeruginosa." Journal of Bacteriology; 2002; pp. 3614-3622; vol. 184 (13).

Van Den Dobbelsteen, et al., "Immunogenicity and safety of a tetravlent *E. coli* O-antigen bioconjugate vaccine in animal models." Vaccine; 2016; pp. 4152-4160; vol. 34 (35).

Wacker, et al., "Prevention of *Staphylococcus aureus* Infections by Glycoprotein Vaccines Synthesized in *Escherichia coli*." Journal of Infectious Diseases; 2014; pp. 1551-1561; vol. 209.

Isar Dejban Golpasha et al: Immunization with 3-oxododecanoyl-L-homoserine lactone-r-PcrV conjugate enhances survival of mice against lethal burn infections caused by Pseudomonas aeruginosa, Bosnian Journal of Basic Medical Sciences, vol. 15, No. 2, Mar. 2, 2015 (Mar. 2, 2015).

International Search report and Written Opinion issued in Application No. PCT/EP2016/075048, dated Feb. 2, 2017.

\* cited by examiner

P AERUGINOSA PCRV-LINKED ANTIGEN VACCINES

CROSS-REFERENCE TO RELATED APPLICATIONS

This is the U.S. National Stage application submitted under 35 U.S.C. § 371 for International Application No. PCT/EP2016/075048, filed Oct. 19, 2016, which claims priority to Application No. GB 1518668.7, filed Oct. 21, 2015, all of which are incorporated herein by reference in their entireties.

REFERENCE TO SEQUENCE LISTING SUBMITTED ELECTRONICALLY VIA EFS-WEB

The content of the electronically submitted sequence listing (Name: VB65998_US_SEQLST.txt; 40,120 bytes; and Date of Creation: Oct. 19, 2016) was originally submitted in the International Application No. PCT/EP2016/075048, filed Oct. 19, 2016, and is incorporated herein by reference in its entirety.

TECHNICAL FIELD

The present invention relates to the field of conjugate based immunogenic compositions and vaccines, their manufacture and the use of such compositions in medicine. More particularly, it relates to the use of PcrV as a new carrier protein from *Pseudomonas aeruginosa*. A PcrV can be used as a carrier protein for other antigens, particularly saccharide antigens or other antigens lacking T cell epitopes. The PcrV carrier protein can act both as a carrier protein and an antigen in its own right.

BACKGROUND

Conjugation of T-independent antigens to carrier proteins has long been established as a way of enabling T-cell help to become part of the immune response for a normally T-independent antigen. In this way, an immune response can be enhanced by allowing the development of immune memory and boostability of the response. Successful conjugate vaccines which have been developed by conjugating bacterial capsular saccharides to carrier proteins are known in the art; the carrier protein having the known effect of turning the T-independent polysaccharide antigen into a T-dependent antigen capable of triggering an immune memory response. For instance WO 02/58737 discloses a vaccine comprising purified capsular polysaccharides from *N. meningitidis* serogroups A, C, W135 and Y conjugated to a carrier protein.

Several carrier proteins are known in the art with tetanus toxoid, diphtheria toxoid, CRM197 and protein D from *Haemophilus influenzae* being used as carrier protein in commercialised vaccines. Diphtheria toxin and mutant forms including CRM197 have also been used in vaccines as safe and effective T-cell dependent carriers for saccharides. CRM197 is currently used in the *Haemophilus influenzae* type b oligosaccharide CRM197 conjugate vaccine (HibTitre®; Lederle Praxis Biologicals, Rochester, N.Y.).

Disease caused by infection with strains of *Pseudomonas* (e.g., *P. aeruginosa*) represents a major threat worldwide. While development of vaccines against such infection is ongoing, there remains a major need for effective vaccines against *Pseudomonas* infection that can safely be produced in high quantities.

The present invention provides a new carrier protein. The *Pseudomonas aeruginosa* PcrV protein has not traditionally been used as a carrier protein. Herein, conjugates are disclosed in which the PcrV protein both acts as a carrier protein for a saccharide antigen and additionally acts as an antigen in its own right so that a neutralising immune response is raised against PcrR and an opsonic response is raised against an LPS.

Accordingly, in one aspect of the present invention there is provided a conjugate comprising an antigen covalently linked to a *Pseudomonas aeruginosa* PcrV carrier protein comprising an amino acid sequence which is at least 80% identical to the sequence of SEQ ID NO:1-4, wherein the antigen is linked (either directly or through a linker) to an amino acid residue of the *P. aeruginosa* PcrV carrier protein.

According to a second aspect of the invention, there is provided a PcrV protein having an amino acid sequence that is at least 80% identical to the sequence of SEQ ID NO:1-4, said amino acid sequence comprising a D/E-X-N-X-S/T consensus sequence wherein X is any amino acid apart from proline.

According to a further aspect of the invention, there is provided an immunogenic composition comprising the conjugate or the PcrV proteins of the invention and a pharmaceutically acceptable excipient.

According to a further aspect of the invention, there is provided a method of making an immunogenic composition of the invention comprising the step of mixing the conjugate or PcrV protein of the invention with a pharmaceutically acceptable excipient.

According to a further aspect of the invention, there is provided a conjugate or PcrV protein according to the invention for use in the treatment of infection and methods of treatment using the conjugate of PcrV protein according to the invention are a further aspect of the invention.

According to a further aspect of the invention, there is provided a polynucleotide encoding a *P. aeruginosa* PcrV protein according to the invention and a polynucleotide encoding a PcrV protein, having a nucleotide sequence that encodes a polypeptide with an amino acid sequence that is at least 80% identical to any one of SEQ ID NO: 1-4.

According to a further aspect of the invention, there is provided a vector comprising the polynucleotide of the invention.

According to a further aspect of the invention, there is provided a host cell comprising:
 i) A nucleic acid that encodes a glycosyltransferase;
 ii) A nucleic acid that encodes an oligosaccharyl transferase; and
 iii) A nucleic acid that encodes a *P. aeruginosa* PcrV protein according to the invention.

According to a further aspect of the invenition, there is provided a method of producing a bioconjugate that comprises a *P. aeruginosa* PcrV protein linked to a saccharide, said method comprising culturing the host cell of the invention under condtions suitable for the production of proteins.

According to a further aspect of the invention, there is provided a bioconjugate produced by the process of the invention, wherein said bioconjugate comprises a saccharide linked to a *P. aeruginosa* PcrV protein.

3A: Detection of formylated single O6 repeat unit bound to lipid A core by Western blotting. *E. coli* W3110 Δwec was transformed with a cosmid encoding the (incomplete) rfbO6 cluster and an expression plasmid encoding the O6 formyltransferase (fmtO6; SEQ NO:65). Cell extracts were harvested after overnight induction during growth at 37° C. in LB medium, digested with proteinase K, separated by SDS PAGE, and electroblotted on nitrocellulose membranes. Immunodetection with an O6 specific antiserum induced a signal in the presence of fmtO6, but not in the empty vector control. This result strongly indicates that formylation is a relelvant antigen on *P. aeruginosa* cells and a prerequisite for detection using this antiserum.

3B: Confirmation of formylation on a single O6 repeat unit released from undecaprenylpyrophosphate. *E. coli* W3110 Δwec ΔwaaL was transformed with the same plamids as above and grown in shake flasks to produce O6 O antigen single repeat units (the wzy polymerase is missing in these strains) and glycolipids were analyzed. Briefly, repeat units were extracted as glycolipids from dried cells, purified by affinity to C18 cartridges, hydrolyzed (to remove undecaprenylpyrophosphate from the O6 O antigen repeat units), labelled with 2 aminobenzamide using reductive amination, and analyzed by normal phase HPLC. Coexpression of fmtO6 gave rise to an additional signal at 61' elution time, containing oligosaccharides corresponding to the labelled, formylated O6 repeat unit, whereas in absence of the gene, the main signal was found at 58' and contained the labelled N acetylated O6 repeat unit.

Figure 4:
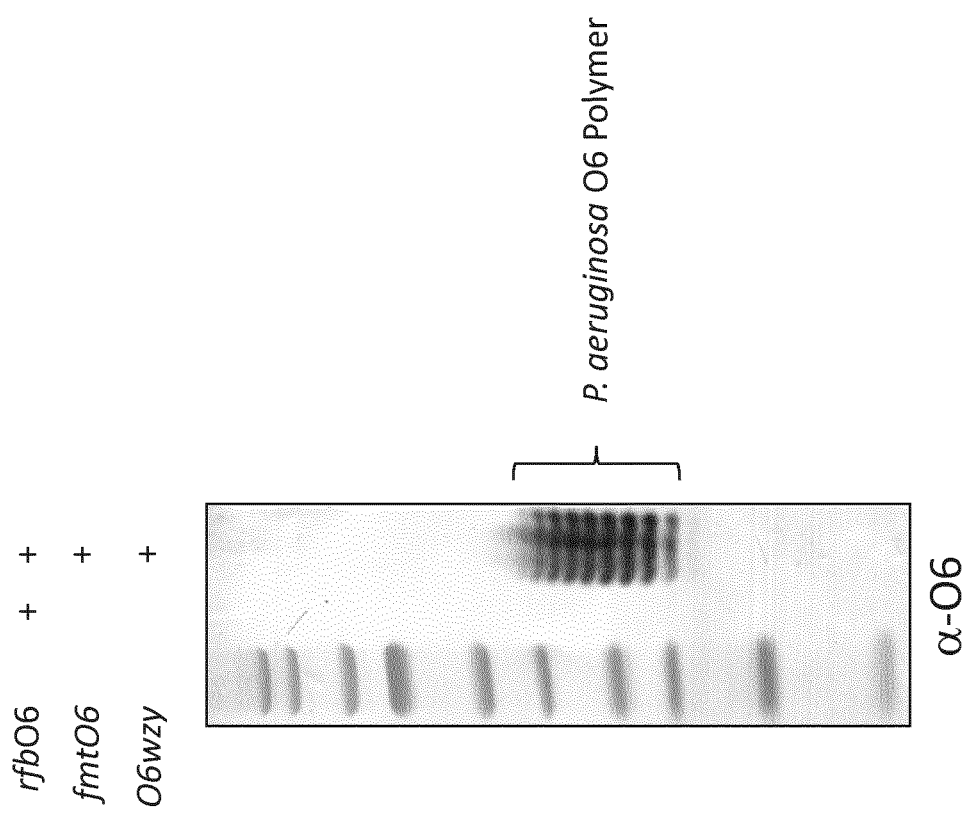

FIG. 4. Functional testing of *P. aeruginosa* O6 candidate wzy polymerase. *E. coli* W3110 Δwec cells containing a cosmid encoding the (incomplete) rfb cluster (lacking the fmtO6 and wzy genes) was transformed with plasmids encoding the fmtO6 and wzy candidate gene PAK_01823 (SEQ ID NO:66) or corresponding empty vectors. Cell extracts were treated with proteinase K and LPS analyzed by immunodetection after SDS PAGE and electrotransfer to nitrocellulose membranes.

Figure 5:
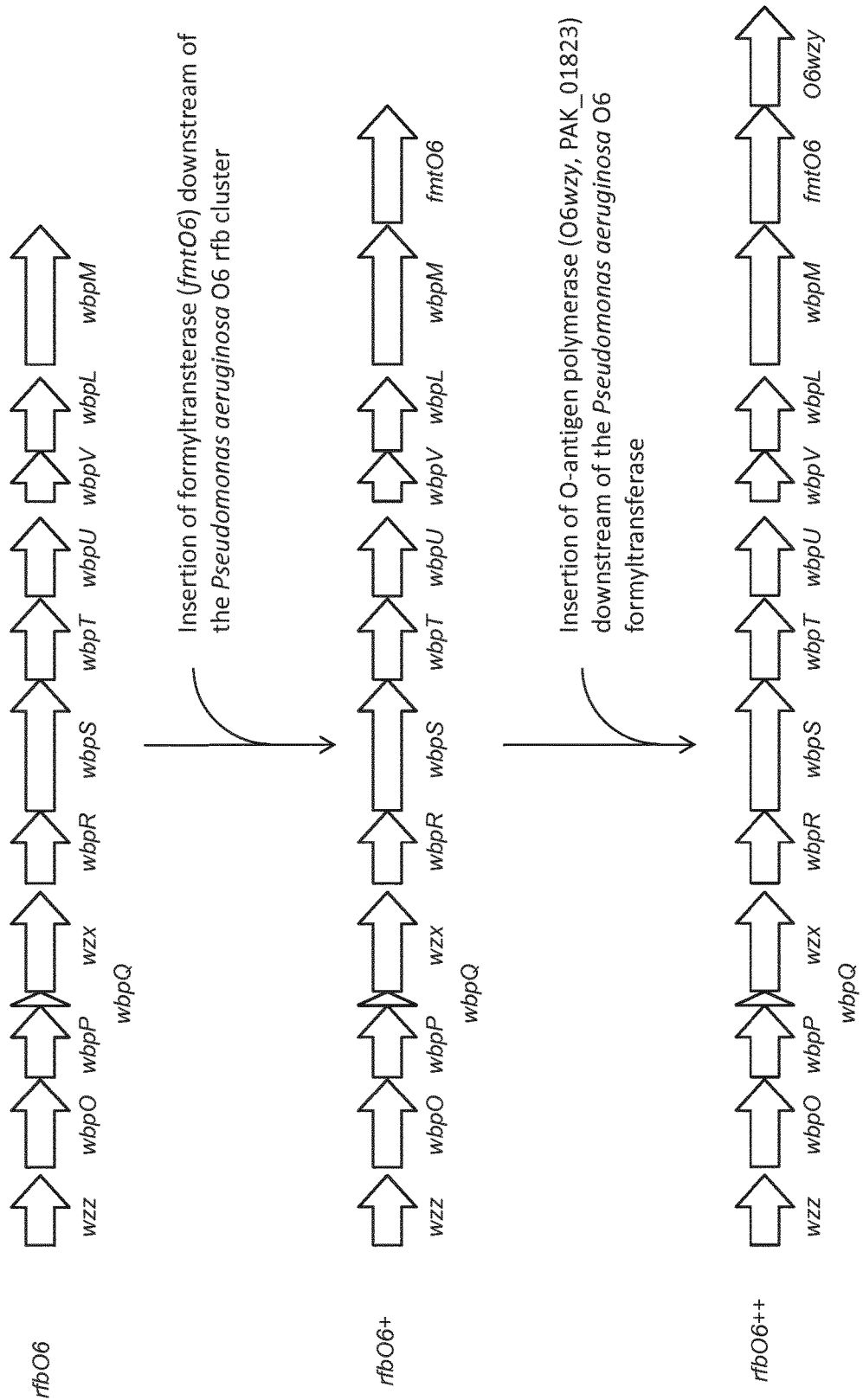

FIG. 5. Cloning of the artificial *Pseudomonas aeruginosa* O6 O antigen expression cluster. First, the rfb cluster of *P. aeruginosa* O6 strain stGVXN4017 (*Pseudomonas aeruginosa* O6 "PAK" strain) was cloned into a cosmid vector by PCR cloning using standard techniques. Bioinformatics supported homology searches identified the formyltransferase (FT) and O-antigen polymerase (wzy), which were subsequently inserted downstream of the rfb cluster in a step wise manner. The resulting gene clusters are able to commit complete *P. aeruginosa* O6 O antigen repeat unit biosynthesis (rfbO6+, no polymer) and polysaccharide (rfbO6++, in which wzy is included) biosynthesis in *E. coli* W3110 derivatives.

Figure 6A:
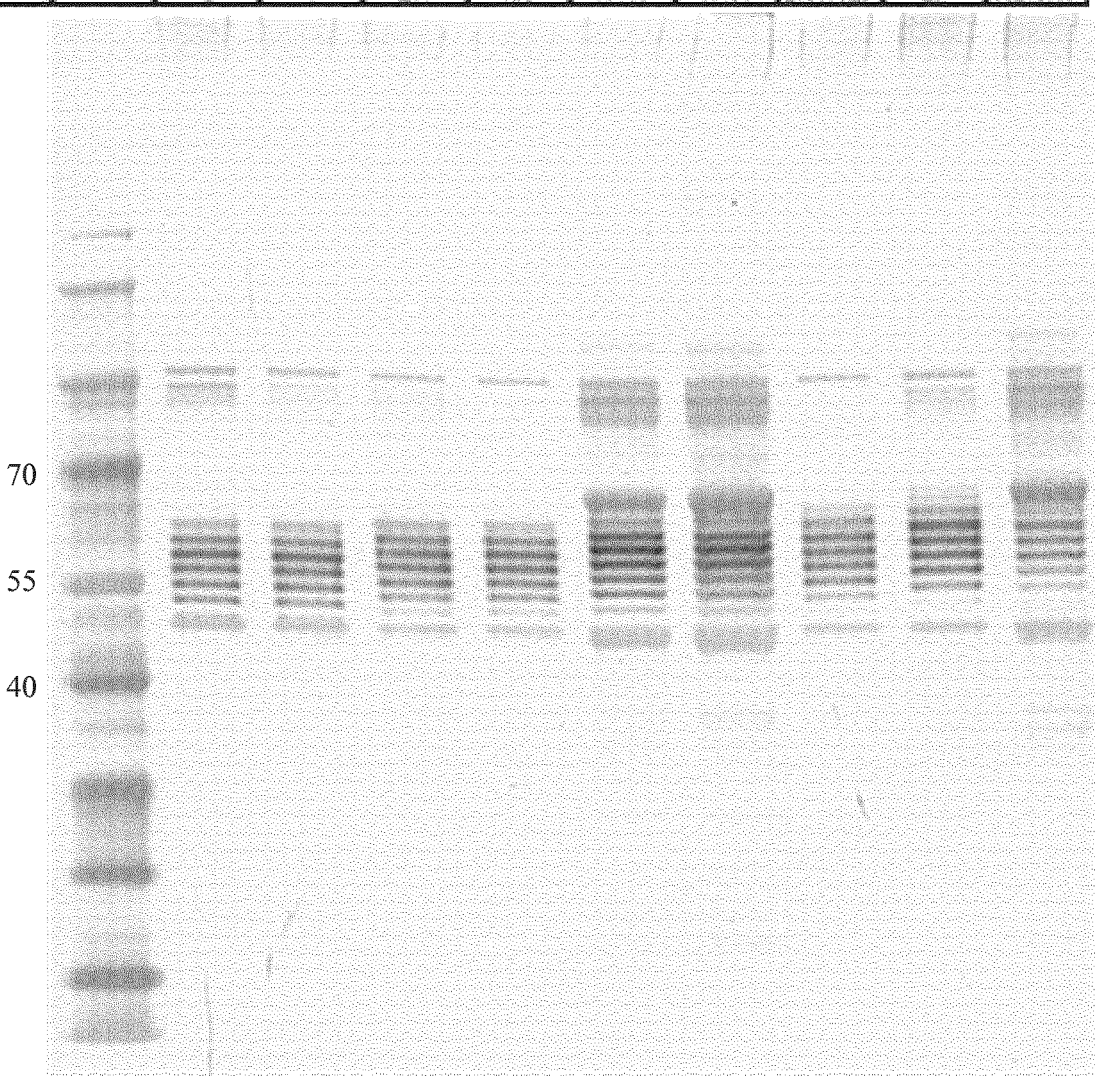
Figure 6B:
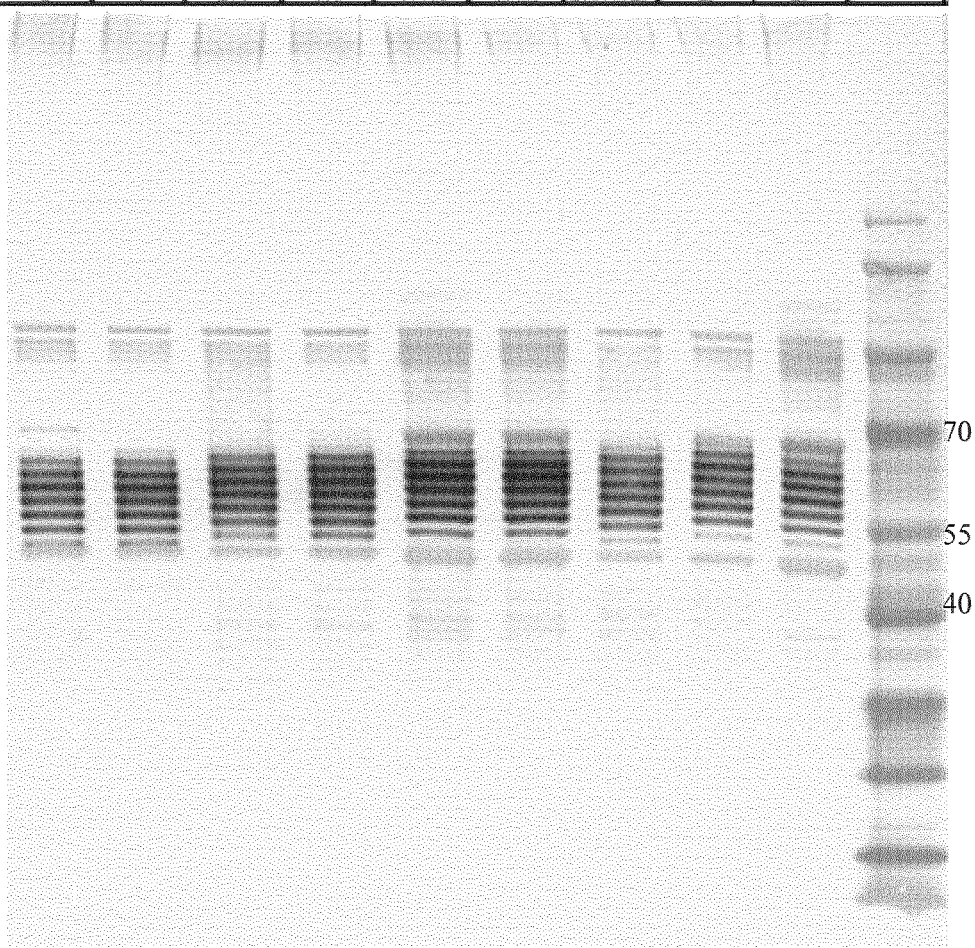
Figure 6C:
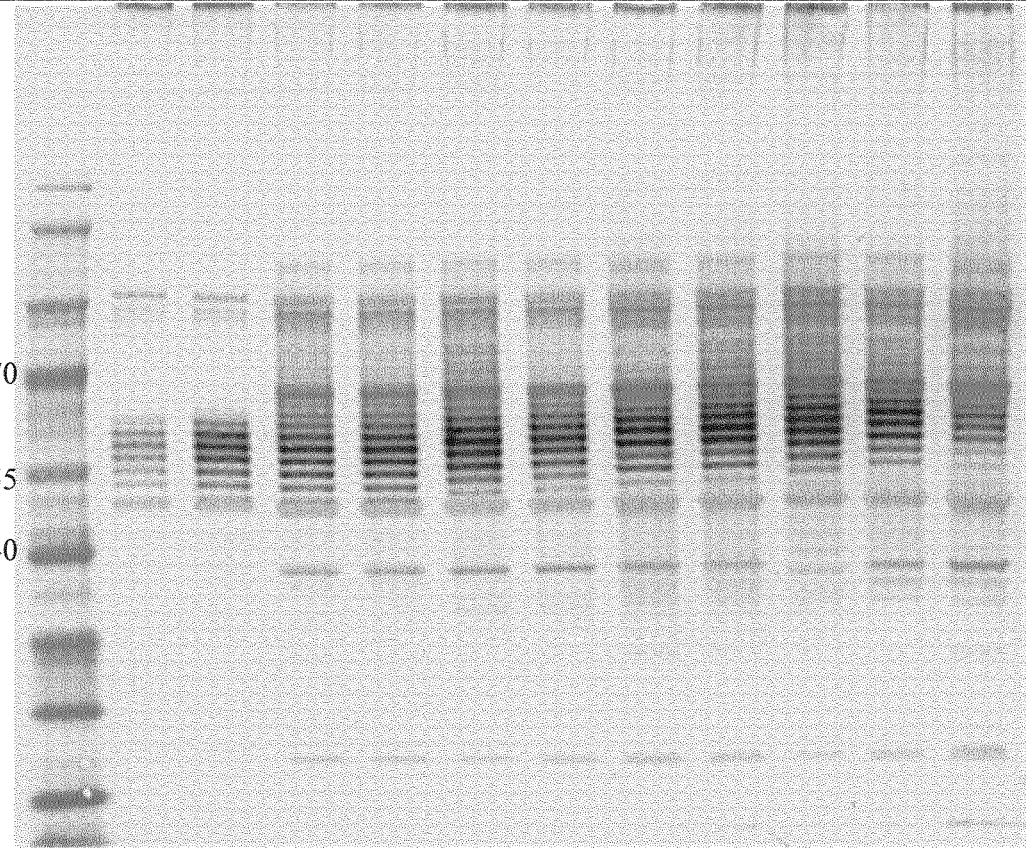

FIG. 6 depicts a Western blot of periplasmic extracts from modified host cells that produce bioconjugates. Strains as described in the Examples are indicated.

6A: results for "St7343" *E. coli* strain modified to comprise integrated pglB and integrated rfb cluster from *P. aeruginosa* O6.

6B: results for "St7209" *E. coli* strain modified to comprise plasmid-borne pglB and integrated rfb cluster from *P. aeruginosa* O6.

6C: results for "St2182" *E. coli* strain modified to comprise plasmid-borne pglB and plasmid-borne rfb cluster from *P. aeruginosa* O6.

Figure 7:
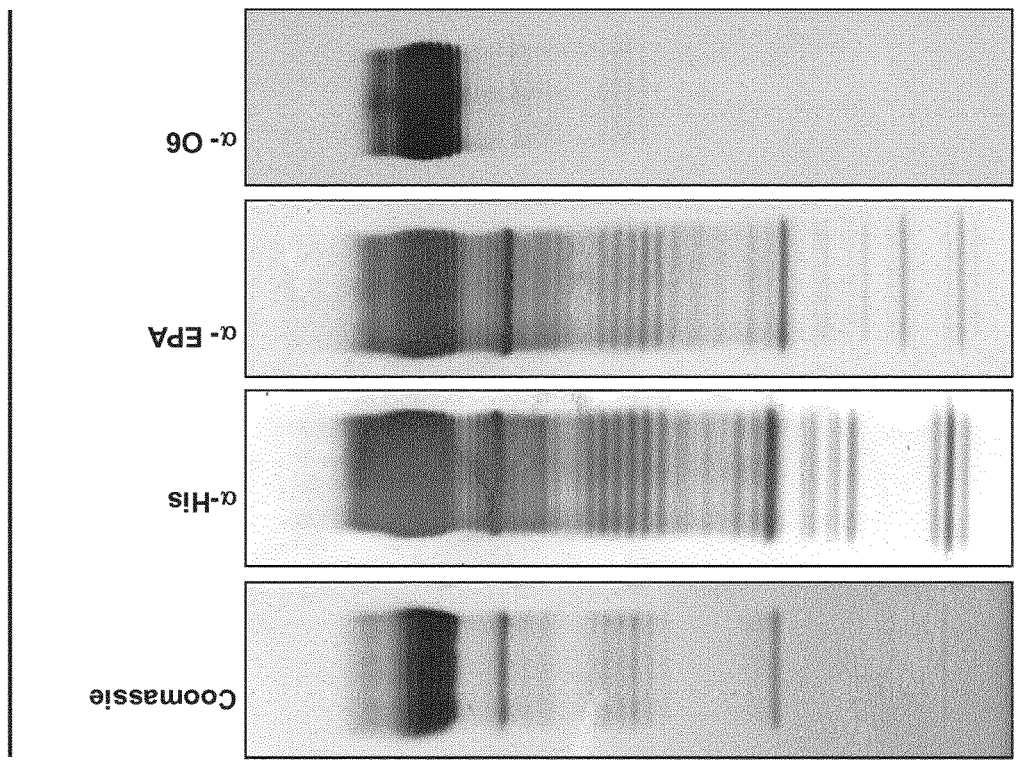

FIG. 7. Purified EPA-O6 glycoconjugate. EPA-O6 was purified from periplasmic extract of modified host cells using Metal-chelate affinity chromatography, anion exchange chromatography and size exclusion chromatography (SEC). The final SEC eluate was characterized by SDS-PAGE followed by Coomassie Blue staining or Western blot using the indicated antibodies.

Figure 8:
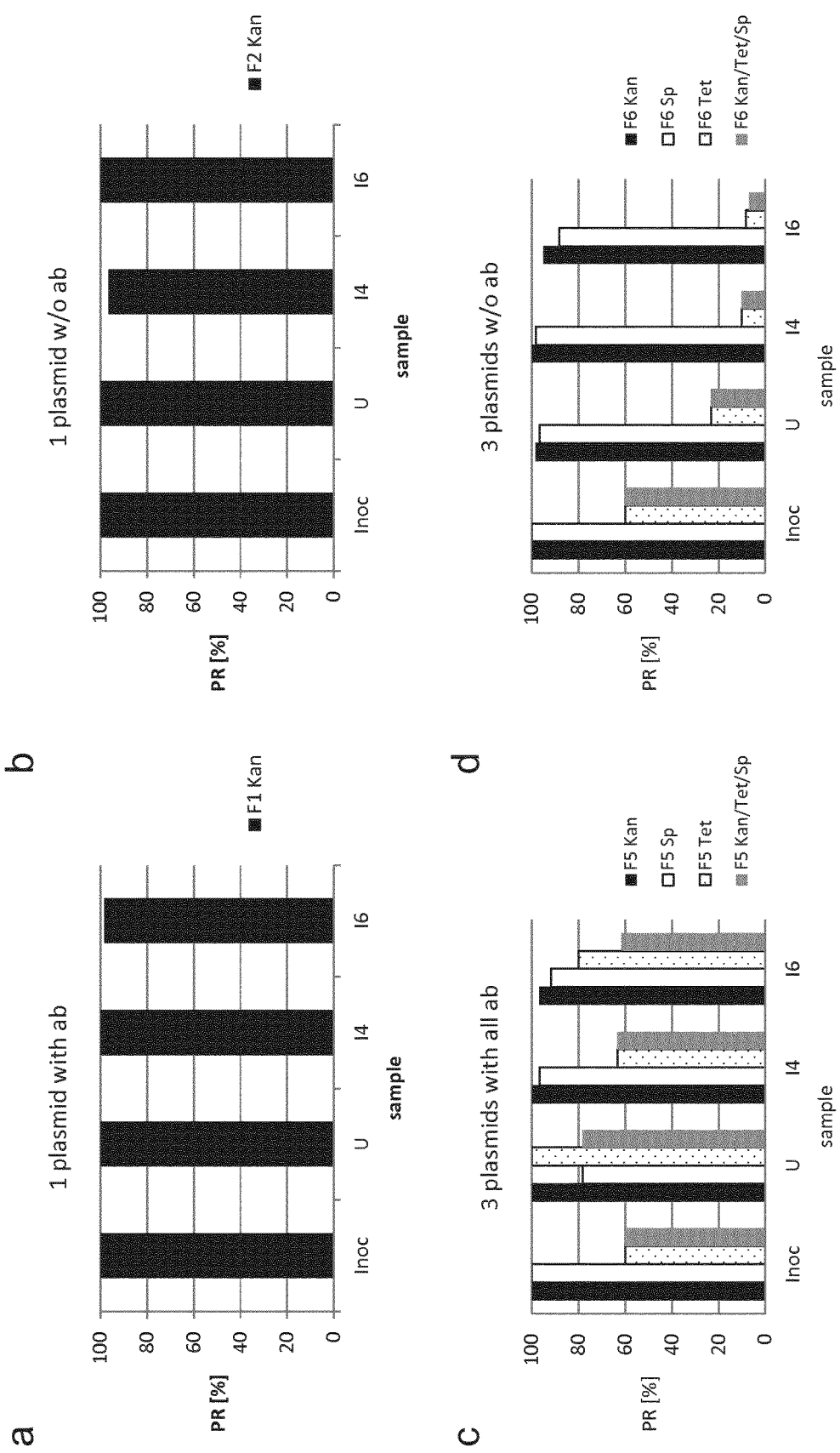

FIG. 8. Plasmid retention (PR) of 1 and 3 plasmid systems in the presence and absence of antibiotic selection pressure. The PR is expressed in % of cells that contain the respective plasmid. Figures A and B show PR of the EPA-plasmid (Kanamycin, black) in modified host cells with integrated rfb cluster and pglB in the presence (A) and absence (B) of Kanamycin. Figures C and D show PR of the EPA-plasmid (Kanamycin, black), pglB-Plasmid (Spectinomycin, white) and rfb cluster plasmid (Tetracyclin, dotted) in modified host cells in the presence (C) and absence (D) of all three antibiotics. The percentage of cells in which all three plasmids are retained is shown in grey. Inoc=Inoculum; U=uninduced cells; 14=cells 6 hours after induction; 16=cells after o/n induction.

Figure 9:
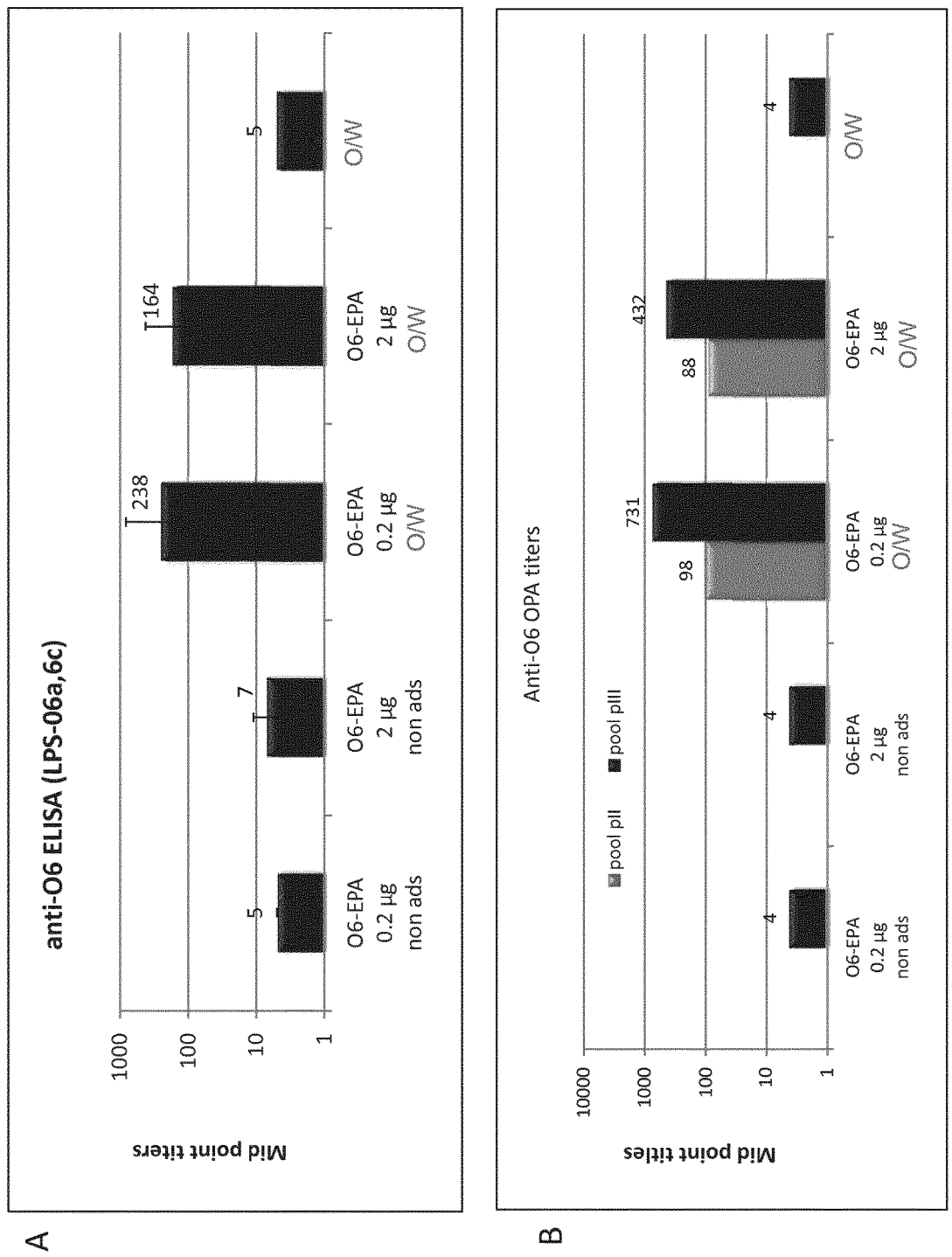

FIG. 9. Biologic activity of vaccine induced anti-O6 antiserum.

9A: ELISA mid point titers of pooled mouse sera from the different vaccination groups after the third injection. Non ads=non adjuvanted, O/W: indicates the adjuvant used, an oil-in-water emulsion adjuvant. O/W alone is a control group that did not contain a glycoconjugate.

9B: Opsonphagocytotic killing mid point titers (inducing a 50% reduction in cfu compared to control) are indicated. Pool pII and pIII are pooled sera harvested after the second and third injection.

Figure 10:
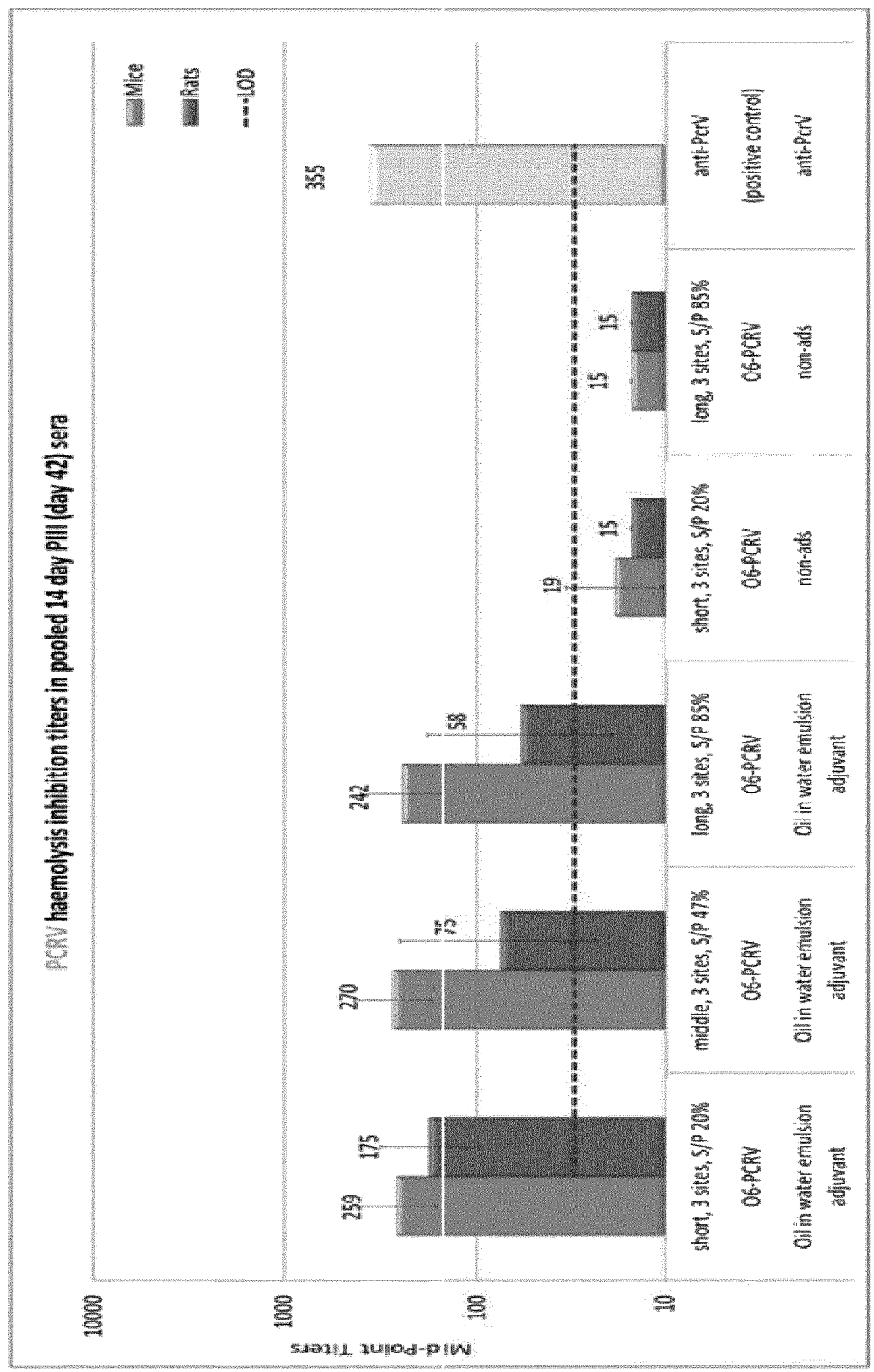

FIG. 10. PcrV haemolysis inhibition titres in pooled sera from day 14 PIII (day 42).

Figure 11:
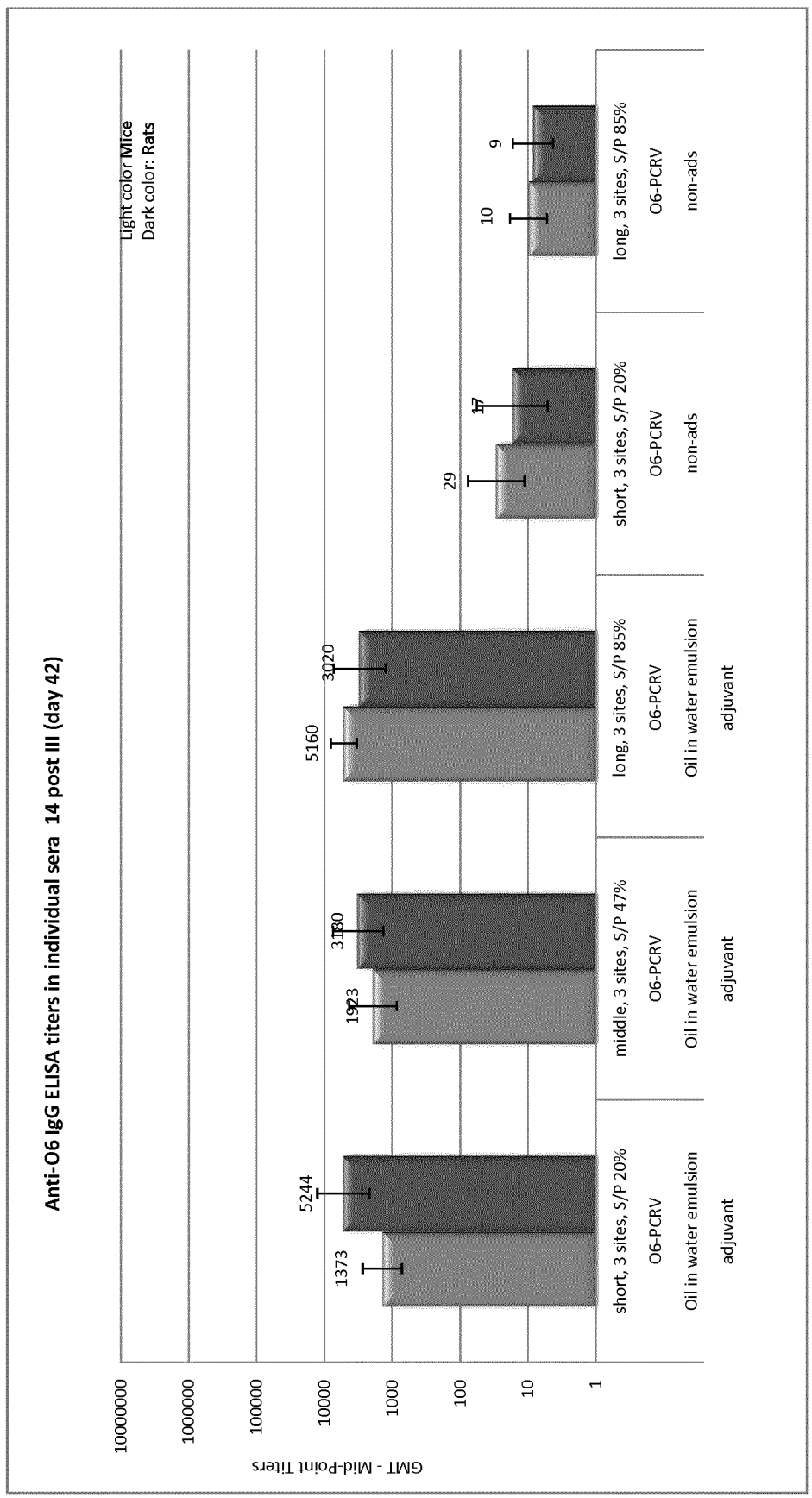

FIG. 11. Anti-O6 IgG ELISA titres in individual sera from 14 days post II (day 42).

Figure 12:
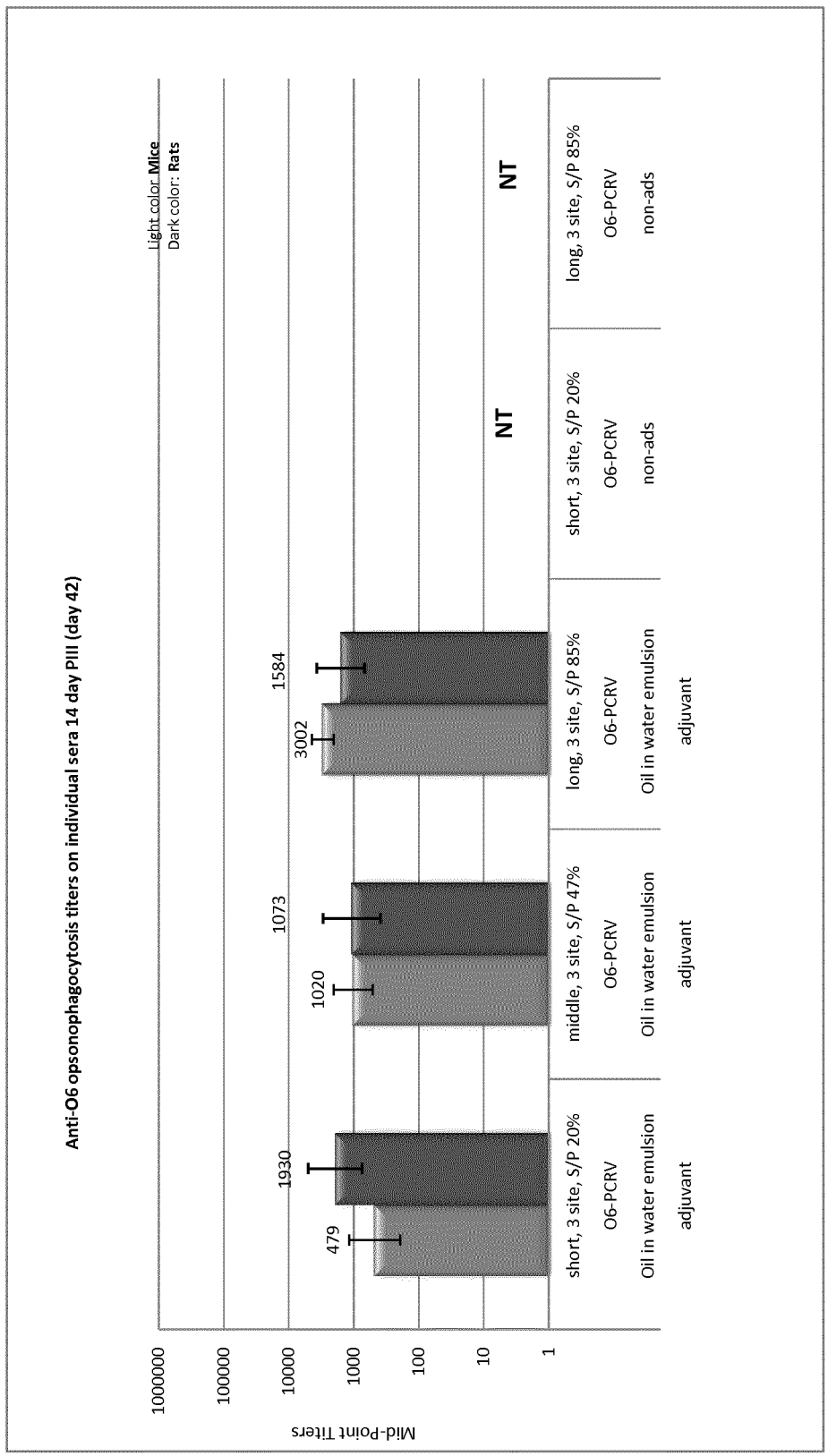

FIG. 12. Anti-O6 opsonophagocytosis titres on individual sera 14 days PIII (day 24).

Figure 13:
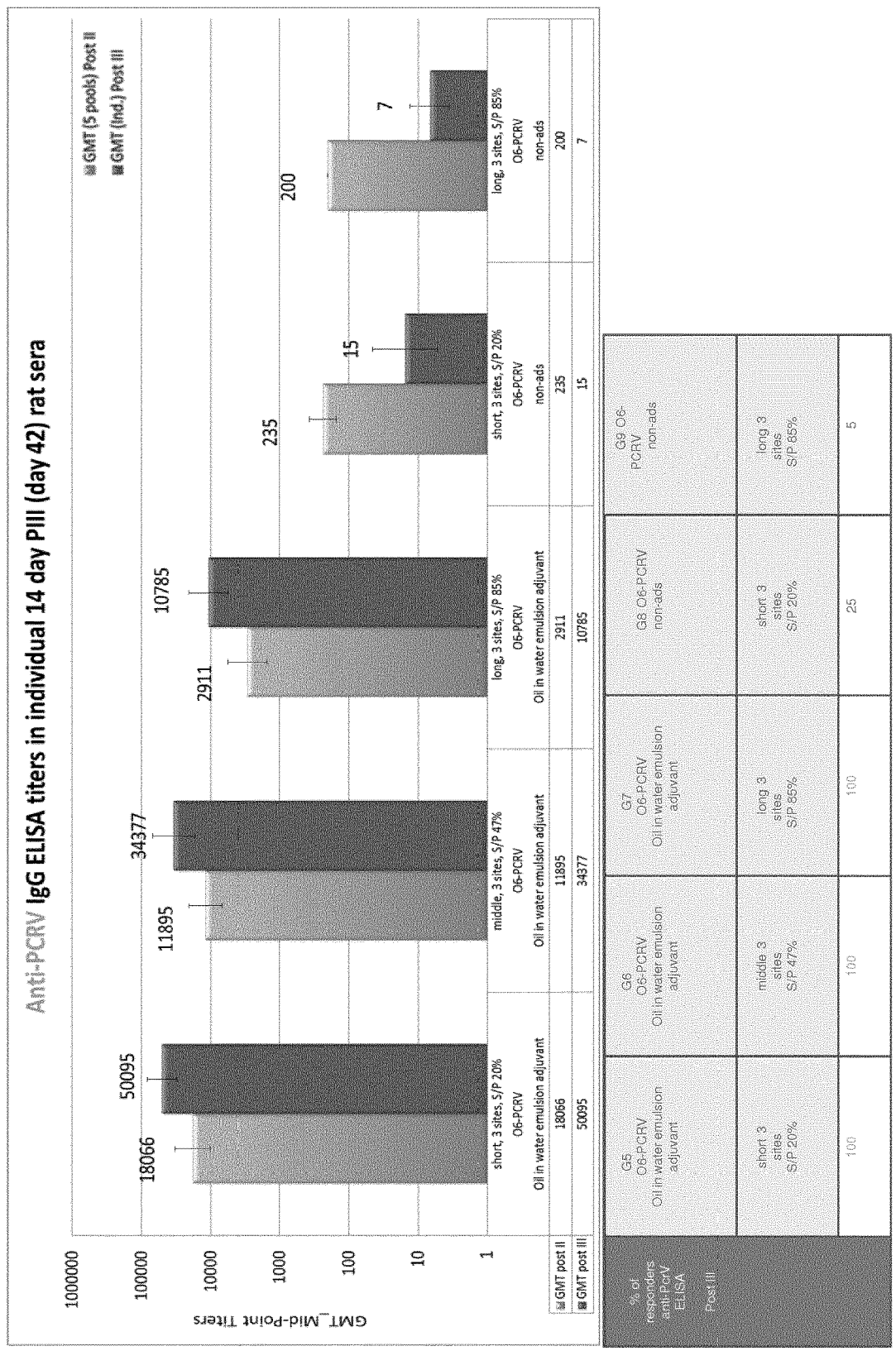

FIG. 13. Anti-PcrV IgG ELISA titres in 14 day PII (day 28) and 14 post III (day 42) rat sera.

Figure 14:
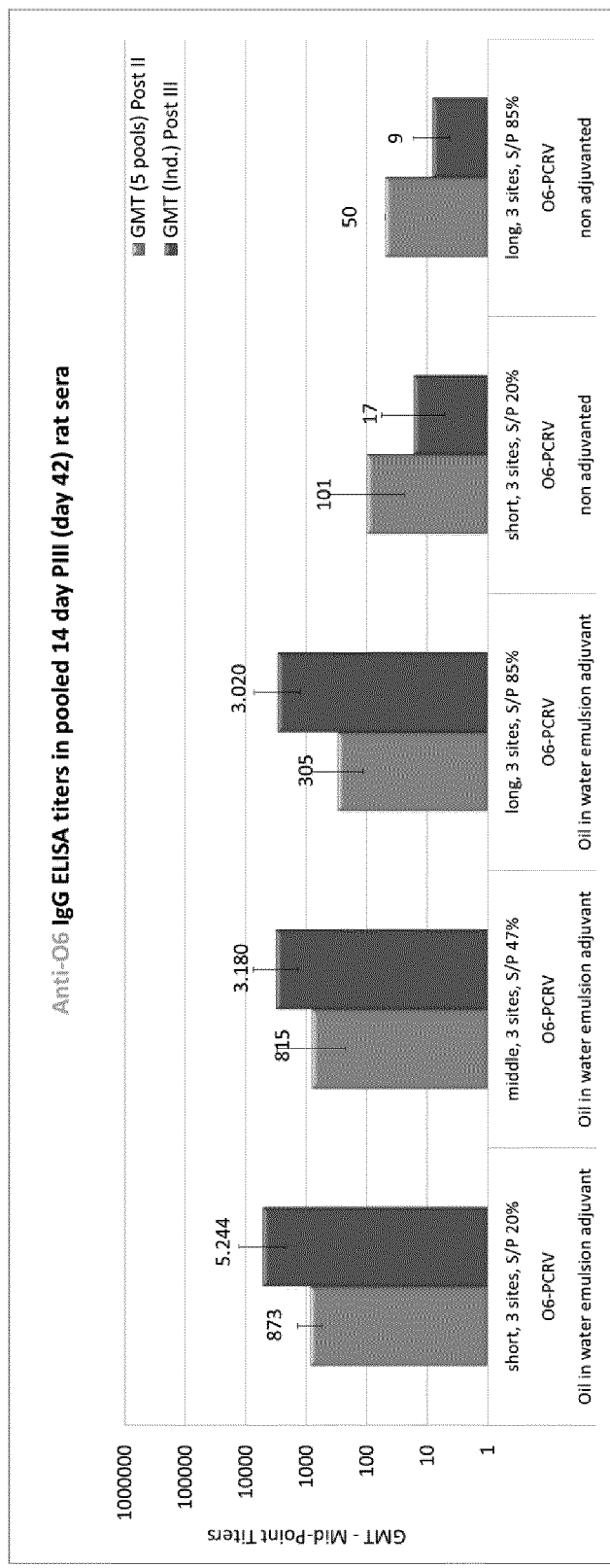

FIG. 14. Anti-O6 IgG ELISA titres in pooled 14 day post III (day 42) rat sera.

DETAILED DESCRIPTION

The present invention discloses a conjugate comprising an antigen covalently linked to a *Pseudomonas aeruginosa* PcrV carrier protein comprising an amino acid sequence which is at least 70%, 80%, 85%, 90%, 95%, 96%, 97%, 98%, 99% or 100% identical to the sequence of SEQ ID NO:1-4, wherein the antigen is linked (either directly or through a linker) to an amino acid residue of the *P. aeruginosa* PcrV carrier protein.

In an embodiment, the amino acid residue to which the antigen is linked is not an asparagine residue and in this case, the conjugate is typically produced by chemical conjugation, for which many processes are well known in the art. For example, the amino acid is selected from the group consisting of: Ala, Arg, Asp, Cys, Gly, Glu, Gln, His, Ile, Leu, Lys, Met, Phe, Pro, Ser, Thr, Trp, Tyr, and Val. Optionally, the amino acid is: an amino acid containing a terminal amine group, a lysine, an arginine, a glutaminic acid, an aspartic acid, a cysteine, a tyrosine, a histidine, an arginine or a tryptophan.

In an embodiment, the antigen is covalently linked to the *Pseudomonas aeruginosa* PcrV carrier protein through a chemical linkage obtainable using a chemical conjugation method.

In an embodiment, the chemical conjugation method is selected from the group consisting of carbodiimide chemistry, reductive animation, cyanylation chemistry (for example CDAP chemistry), maleimide chemistry, hydrazide chemistry, ester chemistry, and N-hydroysuccinimide chemistry. Optionally, the antigen is covalently linked to an aspartic acid, glutamic acid, lysine, cysteine, tyrosine, histidine, arginine or tryptophan amino acid on the *P. aerogionosa* PcrV carrier protein.

In an embodiment, the antigen is directly linked to the *P. aeruginosa* PcrV carrier protein.

In an embodiment, the antigen is attached to the *P. aeruginosa* PcrV carrier protein via a linker. Optionally, the linker is selected from the group consisting of linkers with 4-12 carbon atoms, bifunctional linkers, linkers containing 1 or 2 reactive amino groups at the end, B-proprionamido, nitrophenyl-ethylamine, haloacyl halides, 6-aminocaproic acid and ADH.

In general the following types of chemical groups on a protein carrier can be used for coupling/conjugation:

A) Carboxyl (for instance via aspartic acid or glutamic acid). In one embodiment this group is linked to amino groups on saccharides directly or to an amino group on a linker with carbodiimide chemistry e.g. with EDAC.

B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.

C) Sulphydryl (for instance via cysteine). In one embodiment this group is linked to a bromo or chloro acetylated saccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or NH2. Aldehyde groups can be generated after different treatments known in the art such as: periodate, acid hydrolysis, hydrogen peroxide, etc.

Direct Coupling Approaches:

Saccharide-OH+CNBr or CDAP→cyanate ester+NH2-Prot→conjugate

Saccharide-aldehyde+NH2-Prot→Schiff base+NaCNBH3→conjugate

Saccharide-COOH+NH2-Prot+EDAC→conjugate

Saccharide-NH2+COOH-Prot+EDAC→conjugate

Indirect Coupling Via Spacer (Linker) Approaches:

Saccharide-OH+CNBr or CDAP→cyanate ester+NH2-NH2→saccharide-NH2+COOH-Prot+EDAC→conjugate Saccharide-OH+CNBr or CDAP→cyanate ester+NH2-SH→saccharide-SH+SH-Prot (native Protein with an exposed cysteine or obtained after modification of amino groups of the protein by SPDP for instance)≥saccharide-S—S-Prot Saccharide-OH+CNBr or CDAP→cyanate ester+NH2-SH≥saccharide-SH+maleimide-Prot (modification of amino groups)→conjugate Saccharide-COOH+EDAC+NH2-NH2→saccharide NH2+EDAC+COOH-Prot→conjugate Saccharide-COOH+EDAC+NH2-SH≥saccharide-SH+SH-Prot (native Protein with an exposed cysteine or obtained after modification of amino groups of the protein by SPDP for instance)≥saccharide-S—S-Prot Saccharide-COOH+EDAC+NH2-SH≥saccharide-SH+maleimide-Prot (modification of amino groups)→conjugate Saccharide-Aldehyde+NH2-NH2→saccharide-NH2+EDAC+COOH-Prot→conjugate Note: instead of EDAC above, any suitable carbodiimide may be used.

In an embodiment, the conjugate of the invention contains an amino acid residue to which the antigen is linked, wherein the amino acid residue is an asparagine residue.

In an embodiment, the asparagine residue is not part of a D/E-X-N-X-S/T consensus sequence introduced into the amino acid sequence which is at least 50%, 60%, 70%, 80%, 85%, 90%, 92%, 95%, 96%, 97%, 98%, 99% or 100% identical to the sequence of SEQ ID NO:1-4, wherein X is any amino acid apart from proline.

However, in a further embodiment, the asparagine residue is part of a D/E-X-N-X-S/T consensus sequence introduced into the amino acid sequence which is at least 50%, 60%, 70%, 80%, 85%, 90%, 92%, 95%, 96%, 97%, 98%, 99% or 100% identical to the sequence of SEQ ID NO:1-4, wherein X is any amino acid apart from proline, wherein the asparagine residue is situated at a position equivalent to amino acids 23-166 or amino acids 281-317 or at amino acid 317 of SEQ ID NO:3. For example, amino acid 24-100, amino acid 24-50, amino acid 310-317.

In an embodiment, the asparagine residue is part of a D/E-X-N-X-S/T consensus sequence introduced into the amino acid sequence which is at least 50%, 60%, 70%, 80%, 85%, 90%, 92%, 95%, 96%, 97%, 98%, 99% or 100% identical to the sequence of SEQ ID NO:1-4, wherein X is any amino acid apart from proline, wherein the asparagine residue is situated between amino acids 1-143 or amino acids 258-294 or at amino acid 294 of SEQ ID NO:4. For example, at amino acid 1-100 or amino acid 1-50 or amino acid 1-25 or amino acid 290-294 of SEQ IS NO:4.

In an embodiment, the asparagine residue is part of a D/E-X-N-X-S/T consensus sequence, wherein X is any amino acid apart from proline, wherein the asparagine residue is not introduced by mutation into the sequence of SEQ ID NO:5 or a sequence having at least 50%, 60%, 70%, 80%, 85%, 90%, 92%, 95%, 96%, 97%, 98%, 99% or 100% identity to SEQ ID NO:5.

In an embodiment, a peptide comprising the D/E-X-N-X-S/T consensus sequence is introduced into the amino acid sequence by the removal of a PcrV peptide sequence and its replacement with the peptide comprising the D/E-X-N-X-S/T consensus sequence. In an embodiment, the PcrV peptide sequence which is removed contains 1-7 amino acids or 7, 6, 7, 4, 3, 2 or one amino acid.

In an embodiment, the peptide comprising the D/E-X-N-X-S/T consensus sequence is introduced into the amino acid sequence at a position between amino acid residue 23-166 of SEQ ID NO:3 or amino acids residue 1-143 of SEQ ID:4 at a position between amino acid residue 23-100, 23-50 of SEQ ID NO:3 or amino acids residue 1-100, 1-50 or 1-24 of SEQ ID:4.

In an embodiment, at least 1, 2, 3, 4 or 5 D/E-X-N-X-S/T consensus sequences are introduced into the sequence of any one of SEQ ID NO:1-4 or a sequence with at least 50%, 60%, 70%, 80%, 85%, 90%, 92%, 95%, 96%, 97%, 98%, 99% or 100% identity thereto.

In an embodiment, the PcrV carrier protein has a sequence comprising at least one of SEQ ID NO: 6-62, for example SEQ ID NO:6-12 and 33.

In an embodiment, the PcrV carrier protein has a sequence comprising at least 1, 2, 3, 4 or 5 of SEQ ID NO:6-12 and 33, optionally at least 3 of SEQ ID NO:6-12 and 33.

In an embodiment, the PcrV carrier protein has a sequence comprising SEQ ID NO:6 and/or SEQ ID NO:9 and/or SEQ ID NO:11 and/or SEQ ID NO:33.

In an embodiment the antigen is a saccharide such as a bacterial capsular saccharide, a bacterial lipopolysaccharides or lipooligosaccharide.

The saccharides may be selected from a group consisting of: *N. meningitidis* serogroup A capsular saccharide (MenA), *N. meningitidis* serogroup C capsular saccharide (MenC), *N. meningitidis* serogroup Y capsular saccharide (MenY), *N. meningitidis* serogroup W capsular saccharide (MenW), *H. influenzae* type b capsular saccharide (Hib), Group B *Streptococcus* group I capsular saccharide, Group B *Streptococcus* group II capsular saccharide, Group B *Streptococcus* group III capsular saccharide, Group B *Streptococcus* group IV capsular saccharide, Group B *Streptococcus* group V capsular saccharide, *Staphylococcus aureus* type 5 capsular saccharide, *Staphylococcus aureus* type 8 capsular saccharide, Vi saccharide from *Salmonella typhi*, *N. meningitidis* LPS (such as L3 and/or L2), *M. catarrhalis* LPS, *H. influenzae* LPS, *Shigella* O-antigens, *P. aeruginosa* O-antigens, *E. coli* O-antigens and from any of the capsular pneumococcal saccharides such as from serotype: 1, 2, 3, 4, 5, 6A, 6B, 7F, 8, 9N, 9V, 10A, 11A, 12F, 14, 15B, 17F, 18C, 19A, 19F, 20, 22F, 23F or 33F.

In an embodiment, the antigen is a lipopolysaccharides from *P. aeruginosa*. Optionally the antigen is a O-antigen from *P. aeruginosa*, optionally O1, O2, O3, O4, O5, O6, O7, O8, O9, O10, O11, O12, O13, O14, O15, O16, O17, O18, O19 or O20, for example O6 or O11. In an embodiment, there is provided a bioconjugate comprising a PcrV carrier protein linked to a *Pseudomonas aeruginosa* O antigen, wherein said *Pseudomonas aeruginosa* O antigen is one of the serotypes described in Knirel et al., 2006, Journal of Endotoxin Research 12(6):324-336, the disclosure of which is incorporated herein by reference in its entirety. In specific embodiments the *P. aeruginosa* O-antigen is from O6 or O11.

A further aspect of the invention is a PcrV protein having an amino acid sequence that is at least 50%, 60%, 70%, 80%, 85%, 90%, 92%, 95%, 96%, 97%, 98%, 99% or 100% identical to the sequence of SEQ ID NO:1-4, said amino acid sequence comprising a D/E-X-N-X-S/T consensus sequence wherein X is any amino acid apart from proline.

In an embodiment the D/E-X-N-X-S/T consensus sequence wherein X is any amino acid apart from proline, is situated at a position between amino acids 23-166 or amino acids 281-317 or amino acid 317 of SEQ ID NO:3.

In an embodiment, the D/E-X-N-X-S/T consensus sequence wherein X is any amino acid apart from proline, is situated between amino acids 1-143 or amino acids 258-294 or amino acid 294 of SEQ ID NO:4.

In an embodiment, a peptide comprising the D/E-X-N-X-S/T consensus sequence is introduced into the amino acid sequence by the removal of a PcrV peptide sequence and its replacement with a peptide comprising the D/E-X-N-X-S/T consensus sequence. In an embodiment, the PcrV peptide sequence contains 1-7 amino acids, optionally 7, 6, 5, 4, 3, 2 or one amino acid.

In an embodiment, the peptide comprising the D/E-X-N-X-S/T consensus sequence is introduced into the amino acid sequence at a position between amino acid residue 23-166 of SEQ ID NO:3 or amino acids residue 1-143 of SEQ ID:4.

In an embodiment, the peptide comprising the D/E-X-N-X-S/T consensus sequence is introduced into the amino acid sequence at a position between amino acid residue 23-100 or 23-48 of SEQ ID NO:3 or amino acids residue 1-75 or 1-24 of SEQ ID:4.

In an embodiment at least 2, 3 or 4 D/E-X-N-X-S/T consensus sequences or exactly 1, 2, 3, 4, 5, or 6 D/E-X-N-X-S/T consensus seuqences are introduced into the sequence of any one of SEQ ID NO:1-4 or a sequence with at least 50%, 60%, 70%, 80%, 85%, 90%, 92%, 95%, 96%, 97%, 98%, 99% or 100% identity thereto.

In an embodiment, the PcrV protein has an amino acid sequence that comprises at least one of SEQ ID NO: 6-62, optionally at least one of SEQ ID NO:6-12 and 33, optionally at least 3 of SEQ ID NO:6-12 and 33.

In an embodiment, the PcrV protein of the invention has an amino acid sequence that comprises SEQ ID NO:6 and/or SEQ ID NO:9 and/or SEQ ID NO:11 and/or SEQ ID NO:33.

In an embodiment, the PcrV carrier proteins used in the generation of the bioconjugates described herein comprise a "tag," i.e., a sequence of amino acids that allows for the isolation and/or identification of the carrier protein. For example, adding a tag to a carrier protein described herein can be useful in the purification of that protein and, hence, the purification of conjugate vaccines comprising the tagged carrier protein. Exemplary tags that can be used herein include, without limitation, histidine (HIS) tags (e.g., hexa histidine-tag, or 6×His-Tag), FLAG-TAG, and HA tags. In certain embodiments, the tags used herein are removable, e.g., removal by chemical agents or by enzymatic means, once they are no longer needed, e.g., after the protein has been purified.

In certain embodiments, the carrier proteins described herein comprise a signal sequence that targets the carrier protein to the periplasmic space of the host cell that expresses the carrier protein. In a specific embodiment, the signal sequence is from *E. coli* DsbA, *E. coli* outer membrane porin A (OmpA), *E. coli* maltose binding protein (MalE), *Erwinia* carotovorans pectate lyase (PelB), FlgI, NikA, or *Bacillus* sp. endoxylanase (XynA), heat labile *E. coli* enterotoxin LTIIb, *Bacillus* endoxylanase XynA, or *E. coli* flagellin (FlgI). In an embodiment, the PcrV protein of the invention comprises a leader sequence which is capable of directing the PcrV protein of the peripasm of the bacterium. Optionally, the leader sequence has an amino acid sequence at least 80%, 85%, 90%, 95%, 96%, 97%, 98%, 99% or 100% identical to SEQ ID NO:63. In an embodiment, an alanine residue is added between the leader sequence and the start of the sequence of the mature protein. Such an alanine residue has the advantage of leading to more efficient cleavage of the leader sequence.

In an embodiment, the PcrV protein of the invention has an amino acid sequence that comprises a peptide tag which is useful for the purification of the PcrV protein. Optionally the peptide tag is located at the C-terminus of the amino acid sequence. Optionally the peptide tag comprises six histidine residues.

A further aspect of the invention is a method of making the immunogenic composition of the invention comprising the step of mixing the conjugate or PcrV protein with a pharmaceutically acceptable excipient.

The PcrV proteins and conjugates of the invention are particularly suited for inclusion in immunogenic compositions and vaccines. A process of the invention may therefore include the step of formulating the PcrV protein or conjugate as an immunogenic composition or vaccine. A further aspect of the invention is an immunogenic composition comprising the conjugate of the invention or the PcrV protein of the invention and a pharmaceutically acceptable excipient. The immunogenic composition of the invention optionally further comprises additional antigens. Examples of such additional antigens are; a conjugate of an O-antigen and a carrier protein, a conjugate of a bacterial capsular polysaccharide and a carrier protein, a conjugate of an LOS and a carrier protein and a protein. Suitably conjugates include 1, 2, 3, 4, 5, 6, 7, 8, 9 or 10 of *P. aeruginosa* O1, O2, O3, O4, O5, O6 O7, O8, O9, O10, O11, O12, O13, O14, O15, O16, O17, O18, O19 or O20. Suitable proteins include further *P. aeruginosa* proteins such as *P. aeruginosa* Exoprotein A or variants thereof such as those described in WO 13/36574, *P. aeruginosa* OmpI or OmpF or PopB (YpoB, YopD, FliC) or hybrid proteins of OprF-OmpI (see U.S. Pat. No. 5,955,090 or 6,300,102).

Immunogenic compositions and vaccines of the invention will typically comprise "pharmaceutically acceptable excipients" which include any excipicent that does not itself induce the production of antibodies harmful to the individual receiving the composition. The compositions typically also contain a diluents such as water, saline, glycerol etc. Additionally, auxiliary substances, such as wetting or emulsifying agents, pH buffering substances, polyols and the like may be present.

The compositions comprising the conjugates or PcrV proteins described herein may comprise any additional components suitable for use in pharmaceutical administration. In specific embodiments, the compositions described herein are monovalent formulations. In other embodiments, the compositions described herein are multivalent formulations, e.g., bivalent, trivalent, and tetravalent formulations. For example, a multivalent formulation comprises more than one antigen for example more tha one conjugate.

In certain embodiments, the compositions described herein additionally comprise a preservative, e.g., the mercury derivative thimerosal. In a specific embodiment, the pharmaceutical compositions described herein comprise 0.001% to 0.01% thimerosal. In other embodiments, the pharmaceutical compositions described herein do not comprise a preservative.

In certain embodiments, the compositions described herein (e.g., the immunogenic compositions) comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a bioconjugate, but when the compound is administered alone does not generate an immune response to the bioconjugate. In some embodiments, the adjuvant generates an immune response to the conjugate or PcrV protein and does not produce an allergy or other adverse reaction. Adjuvants can enhance an immune response by several mechanisms including, e.g., lymphocyte recruitment, stimulation of B and/or T cells, and stimulation of macrophages.

Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see United Kingdom Patent GB2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057, 540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998).

In certain embodiments, the compositions described herein are formulated to be suitable for the intended route of administration to a subject. For example, the compositions described herein may be formulated to be suitable for subcutaneous, parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, the compositions described herein additionally comprise one or more buffers, e.g., phosphate buffer and sucrose phosphate glutamate buffer. In other embodiments, the compositions described herein do not comprise buffers.

In certain embodiments, the compositions described herein additionally comprise one or more salts, e.g., sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts). In other embodiments, the compositions described herein do not comprise salts.

The compositions described herein can be included in a container, pack, or dispenser together with instructions for administration.

The compositions described herein can be stored before use, e.g., the compositions can be stored frozen (e.g., at about −20° C. or at about −70° C.); stored in refrigerated conditions (e.g., at about 4° C.); or stored at room temperature.

Immunogenic compositions used as vaccines comprise an immunologically effective amount of the PcrV protein or conjugate of the invention, as well as any other components. By "immunologicaly effective amount", it is meant that the administration of that amount to an individual, either as a single dose or as part of a series is effective for treatment or prevention. This amount varies depending on the health and physical condition of the individual to be treated, age, the degree of protection desired, the formulation of the vaccine and other relevant factors. It is expected that the amount will fall in a relatively braod range that can be determined through routine trials.

The vaccines of the present invention are preferably adjuvanted. Suitable adjuvants include an aluminum salt such as aluminum hydroxide gel (alum) or aluminium phosphate, but may also be a salt of calcium, magnesium, iron or zinc, or may be an insoluble suspension of acylated tyrosine, or acylated sugars, cationically or anionically derivatized polysaccharides, or polyphosphazenes.

It is preferred that the adjuvant be selected to be a preferential inducer of either a TH1 or a TH2 type of response. High levels of Th1-type cytokines tend to favor the induction of cell mediated immune responses to a given antigen, whilst high levels of Th2-type cytokines tend to favour the induction of humoral immune responses to the antigen.

It is important to remember that the distinction of Th1 and Th2-type immune response is not absolute. In reality an individual will support an immune response which is described as being predominantly Th1 or predominantly Th2. However, it is often convenient to consider the families of cytokines in terms of that described in murine CD4+ve T cell clones by Mosmann and Coffman (Mosmann, T. R. and Coffman, R. L. (1989) TH1 and TH2 cells: different patterns of lymphokine secretion lead to different functional properties. Annual Review of Immunology, 7, p 145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of 11-4, IL-5, IL-6, IL-10. Suitable adjuvant systems which promote a predominantly Th1 response include: Monophosphoryl lipid A or a derivative thereof, particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminium salt (for instance aluminium phosphate or aluminium hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-131].

An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21, 3D-MPL and tocopherol in an oil in water emulsion is described in WO 95/17210, and is a preferred formulation. Preferably the vaccine additionally comprises a saponin, more preferably QS21. The formulation may also comprise an oil in water emulsion and tocopherol (WO 95/17210). The present invention also provides a method for producing a vaccine formulation comprising mixing a protein of the present invention together with a pharmaceutically acceptable excipient, such as 3D-MPL. Unmethylated CpG containing oligonucleotides (WO 96/02555) are also preferential inducers of a TH1 response and are suitable for use in the present invention.

The compositions of the invention may contain an oil in water emulsion, since these have been suggested to be useful as adjuvant compositions (EP 399843; WO 95/17210). Oil in water emulsions such as those described in WO95/17210 (which discloses oil in water emulsions comprising from 2 to 10% squalene, from 2 to 10% alpha tocopherol and from 0.3 to 3% tween 80 and their use alone or in combination with QS21 and/or 3D-MPL), WO99/12565 (which discloses oil in water emulsion compositions comprising a metabolisable oil, a saponin and a sterol and MPL) or WO99/11241 may be used. Further oil in water emulsions such as those disclosed in WO 09/127676 and WO 09/127677 are also suitable.

The vaccine preparations of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance pneumococcal polysaccharides could be administered separately, at the same time or 1-2 weeks after the administration of any bacterial protein component of the vaccine for optimal coordination of the immune responses with respect to each other). For co-administration, the optional Th1 adjuvant may be present in any or all of the different administrations, however it is preferred if it is present in combination with the bacterial protein component of the vaccine. In addition to a single route of administration, 2 different routes of administration may be used. For example, polysaccharides may be administered IM (or ID) and bacterial proteins may be administered IN (or ID). In addition, the vaccines of the invention may be administered IM for priming doses and IN for booster doses.

The amount of conjugate antigen in each vaccine dose is selected as an amount which induces an immunoprotective response without significant, adverse side effects in typical vaccines. Such amount will vary depending upon which specific immunogen is employed and how it is presented. Generally, it is expected that each dose will comprise 0.1-100 μg of polysaccharide, preferably 0.1-50 μg for polysaccharide conjugates, preferably 0.1-10 μg, more preferably 1-10 μg, of which 1 to 5 μg is a more preferable range.

The content of protein antigens in the vaccine will typically be in the range 1-100 μg, preferably 5-50 μg, most typically in the range 5-25 μg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The vaccines of the present invention may be stored in solution or lyophilized. Preferably the solution is lyophilized in the presence of a sugar such as sucrose, trehalose or lactose. It is still further preferable that they are lyophilized and extemporaneously reconstituted prior to use.

In an embodiment, the conjugate or PcrV protein of the invention is for use in the treatment of infection, particularly in the treatment of *P. aeruginosa* infection, for example of a human subject in need thereof.

A further aspect of the invention is a polynucleotide encoding the PcrV protein of the invention. For example a polynucleotide encoding a PcrV protein, having a nucleotide sequence that encodes a polypeptide with an amino acid sequence that is at least 50%, 60%, 70%, 80%, 85%, 90%, 92%, 95%, 96%, 97%, 98%, 99% or 100% identical to any one of SEQ ID NO: 1-4. A vector comprising such a polynucleotide is a further aspect of the invention.

A further aspect of the invention is a host cell comprising:
 i) A nucleic acid that encodes a glycosyltransferase;
 ii) A nucleic acid that encodes an oligosaccharyl transferase; and
 iii) A nucleic acid that encodes a *P. aeruginosa* PcrV protein of the invention.

Such a a modified prokaryotic host cell comprises nucleic acids encoding enzymes capable of producing a bioconjugate comprising an antigen, for example a saccharide antigen attached to a PcrV protein. Such host cells may naturally express nucleic acids specific for production of a saccharide antigen, or the host cells may be made to express such nucleic acids, i.e., in certain embodiments said nucleic acids are heterologous to the host cells. In certain embodiments, one or more of said nucleic acids specific for production of a saccharide antigen are heterologous to the host cell and intergrated into the genome of the host cell. In certain embodiments, the host cells provided herein comprise nucleic acids encoding additional enzymes active in the N-glycosylation of proteins, e.g., the host cells provided herein further comprise a nucleic acid encoding an oligosaccharyl transferase and/or one or more nucleic acids encoding other glycosyltransferases. In certain embodiments, the host cells provided herein comprise a nucleic acid encoding a carrier protein, e.g., a protein to which oligosaccharides and/or polysaccharides can be attached to form a bioconjugate. In a specific embodiment, the host cell is *E. coli*.

Nucleic acid sequences comprising rfb gene clusters that can be inserted into the host cells described herein are known in the art. In a specific embodiment, the rfb gene cluster inserted into a host cell described herein is an rfb gene cluster from *E. coli*, e.g., an *E. coli* rfb cluster from any O serogroup/O antigen known in the art, e.g., O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, or O187, and subserotypes thereof. In another specific embodiment, the rfb gene cluster inserted into a host cell described herein is an rfb gene cluster from a *Pseudomonas* strain (e.g., a *P. aeruginosa* strain), a *Salmonella* strain (e.g., a *S. enterica* strain), a *Yersinia* strain, a *Klebsiella pneumoniae* strain, a *Francisella* strain (e.g., *F. tularensis*), an *Acinetobacter baumannii* strain, a *Burkholderia* strain, or a *Shigella* strain.

Nucleic acid sequences comprising capsular polysaccharide gene clusters that can be inserted into the host cells described herein are known in the art. In a specific embodiment, the capsular polysaccharide gene cluster inserted into a host cell described herein is a capsular polysaccharide gene cluster from an *E. coli* strain, a *Streptococcus* strain (e.g., *S. pneumoniae, S. pyrogenes, S. agalacticae*), a *Staphylococcus* strain (e.g. *S. aureus*), or a *Burkholderia* strain (e.g. *B mallei, B. pseudomallei, B. thailandensis*). Disclosures of methods for making such host cells which are capable of producing conjugates are found in WO 06/119987, WO 09/104074, WO 11/62615, WO 11/138361, WO 14/57109, WO14/72405.

In a specific embodiment, provided herein is a modified prokaryotic host cell comprising nucleic acids encoding enzymes capable of producing a bioconjugate comprising a saccharide antigen, wherein said host cell comprises an rfb cluster from *Pseudomonas* or a glycosyltransferase derived from an rfb cluster from *Pseudomonas*. In a specific embodiment, said rfb cluster from *Pseudomonas* or glycosyltransferase derived from an rfb cluster from *Pseudomonas* is integrated into the genome of said host cell. In another specific embodiment, said rfb cluster from *Pseudomonas* or glycosyltransferase derived from an rfb cluster from *Pseudomonas* is an rfb cluster from *Pseudomonas aeruginosa*. In another specific embodiment, said host cell comprises a nucleic acid encoding an oligosaccharyl transferase (e.g., pglB from *Campylobacter jejuni*). In another specific embodiment, said nucleic acid encoding an oligosaccharyl transferase (e.g., pglB from *Campylobacter jejuni*) is integrated into the genome of the host cell. In a specific embodiment, said host cell comprises a nucleic acid encoding a carrier protein. In another specific embodiment, the host cell is *E. coli*.

In another specific embodiment, provided herein is a modified prokaryotic host cell comprising (i) an rfb cluster from *Pseudomonas*, wherein said rfb cluster is integrated into the genome of said host cell; (ii) a nucleic acid encoding an oligosaccharyl transferase (e.g., pglB from *Campylobacter jejuni*), wherein said nucleic acid encoding an oligosaccharyl transferase is integrated into the genome of the host cell; and (iii) a carrier protein, wherein said carrier protein is either plasmid-borne or integrated into the genome of the host cell. In another specific embodiment, said rfb cluster from *Pseudomonas* is an rfb cluster from *Pseudomonas aeruginosa*. In another specific embodiment, the host cell is *E. coli*.

In another specific embodiment, provided herein is a modified prokaryotic host cell comprising (i) a glycosyltransferase derived from an rfb cluster from *Pseudomonas*, wherein said glycosyltransferase is integrated into the genome of said host cell; (ii) a nucleic acid encoding an oligosaccharyl transferase (e.g., pglB from *Campylobacter jejuni*), wherein said nucleic acid encoding an oligosaccharyl transferase is integrated into the genome of the host cell; and (iii) a carrier protein, wherein said carrier protein is either plasmid-borne or integrated into the genome of the host cell. In another specific embodiment, said glycosyltransferase derived from an rfb cluster from *Pseudomonas* is an rfb cluster from *Pseudomonas aeruginosa*. In another specific embodiment, the host cell is *E. coli*.

In a specific embodiment, the rfb cluster from *Pseudomonas* or glycosyltransferase derived from an rfb cluster from *Pseudomonas* is an rfb cluster or glycosyltransferase from *Pseudomonas aeruginosa*. In another specific embodiment, said rfb cluster from *Pseudomonas* or glycosyltransferase derived from an rfb cluster from *Pseudomonas* is an rfb cluster or glycosyltransferase from *Pseudomonas aeruginosa* serotype O1, O2, O3, O4, O5, O6, O7, O8, O9, O10, O11, O12, O13, O14, O15, O16, O17, O18, O19, or O20. In another specific embodiment, said rfb cluster from *Pseudomonas aeruginosa* is the rfb cluster from any one of the serotypes described in Knirel et al., 2006, Journal of Endotoxin Research 12(6):324-336, the disclosure of which is incorporated herein by reference in its entirety. In a specific embodiment, said rfb cluster from *Pseudomonas* or glycosyltransferase derived from an rfb cluster from *Pseudomonas* is an rfb cluster or glycosyltransferase from *Pseudomonas aeruginosa* serotype O6 PAK strain. In a specific embodiment, said rfb cluster from *Pseudomonas* or glycosyltransferase derived from an rfb cluster from *Pseudomonas* is an rfb cluster or glycosyltransferase from *Pseudomonas aeruginosa* serotype O11, e.g., *Pseudomonas aeruginosa* strain PA103 (see, e.g., Genbank Accession No. KF364633.1). In a specific embodiment, the genes encoding a formyltransferase enzyme (GenBank: EOT23134.1; NCBI protein ID: PAK_01412; SEQ ID NO:65) and a wzy polymerase (GenBank: EOT19368.1; NCBI protein ID: PAK_01823; SEQ ID NO:66) are introduced (e.g., via plasmid or integration) in addition to said rfb cluster from *Pseudomonas aeruginosa* serotype O6 PAK strain in order to functionally extend it.

In a specific embodiment, a modified prokaryotic host cell provided herein comprises a nucleic acid that encodes a formyltransferase. In another specific embodiment, said formyltransferase is the formyltransferase presented in SEQ ID NO:65, or a homolog thereof. In another specific embodiment, said formyltransferase is incorporated (e.g., inserted into the genome of or plasmid expressed by) in said host cell as part of a *Pseudomonas* rfb cluster, wherein said *Pseudomonas* rfb cluster has been modified to comprise the formyltransferase. In another specific embodiment, said *Pseudomonas* rfb cluster is a *Pseudomonas aeruginosa* serotype O6 rfb cluster.

In another specific embodiment, a modified prokaryotic host cell provided herein comprises a nucleic acid that encodes a wzy polymerase. In another specific embodiment, said wzy polymerase is the wzy polymerase presented in SEQ ID NO:66, or a homolog thereof. In another specific embodiment, said wzy polymerase is incorporated (e.g., inserted into the genome of or plasmid expressed by) in said host cell as part of a *Pseudomonas* rfb cluster, wherein said *Pseudomonas* rfb cluster has been modified to comprise the wzy polymerase. In another specific embodiment, said *Pseudomonas* rfb cluster is a *Pseudomonas aeruginosa* serotype O6 rfb cluster.

In another specific embodiment, a modified prokaryotic host cell provided herein comprises (i) a nucleic acid that encodes a formyltransferase and (ii) a nucleic acid that encodes a wzy polymerase. In a specific embodiment, said formyltransferase is the formyltransferase presented in SEQ ID NO:65, or a homolog thereof having at least 85%, 90% or 95% identity to SEQ ID NO:65. In another specific embodiment, said wzy polymerase is the wzy polymerase presented in SEQ ID NO:66, or a homolog thereof having at least 85%, 90% or 95% identity to SEQ ID NO:66. In a specific embodiment, said formyltransferase and said wzy polymerase are incorporated (e.g., inserted into the genome of or plasmid expressed by) in said host cell as part of a *Pseudomonas* rfb cluster, wherein said *Pseudomonas* rfb cluster has been modified to comprise the formyltransferase and wzy polymerase. In another specific embodiment, said *Pseudomonas* rfb cluster is a *Pseudomonas aeruginosa* serotype O6 rfb cluster.

Nucleic acids that encode formyltransferases and nucleic acids that encode wzy polymerases that are use to generate modified *Pseudomonas* rfb clusters, e.g., modified *Pseudomonas aeruginosa* serotype O6 rfb clusters, can be inserted into the rfb cluster at multiple positions and in multiple orientations.

In a specific embodiment, the gene encoding said formyltransferase and/or the gene encoding said wzy polymerase is/are inserted downstream of the genes of the *Pseudomonas* rfb cluster, e.g., the *Pseudomonas aeruginosa* serotype O6 rfb cluster. In a specific embodiment, the the gene encoding said formyltransferase and/or the gene encoding said wzy polymerase is/are inserted downstream of the wbpM gene of the *Pseudomonas aeruginosa* serotype O6 rfb cluster.

In a specific embodiment, the gene encoding said formyltransferase and/or the gene encoding said wzy polymerase is/are inserted upstream of the genes of the *Pseudomonas* rfb cluster, e.g., the *Pseudomonas aeruginosa* serotype O6 rfb cluster. In a specific embodiment, the gene encoding said formyltransferase and/or the gene encoding said wzy polymerase is/are inserted downstream of the wzz gene of the *Pseudomonas aeruginosa* serotype O6 rfb cluster.

In a specific embodiment, the gene encoding said formyltransferase and/or the gene encoding said wzy polymerase is/are inserted in a clockwise orientation relative to the genes of the *Pseudomonas* rfb cluster, e.g., the *Pseudomonas aeruginosa* serotype O6 rfb cluster.

In a specific embodiment, the gene encoding said formyltransferase and/or the gene encoding said wzy polymerase is/are inserted in a counter-clockwise orientation relative to the genes of the *Pseudomonas* rfb cluster, e.g., the *Pseudomonas aeruginosa* serotype O6 rfb cluster.

In a specific embodiment, provided herein is a modified prokaryotic host cell comprising nucleic acids encoding enzymes capable of producing a bioconjugate comprising a *Pseudomonas* O6 antigen. In a specific embodiment, said host cell comprises the *Pseudomonas aeruginosa* serotype O6 rfb cluster, a nucleic acid encoding a wzy polymerase, and a formyltransferase. In a specific embodiment, the wzy polymerase is the *P. aeruginosa* O6 wzy polymerase (SEQ ID NO:66), or a homolog thereof (e.g., the wzy polymerase from the PAK or LESB58 strain of *Pseudomonas aeruginosa*). In another specific embodiment, the formyltransferase is the *P. aeruginosa* O6 formyltransferase (SEQ ID NO:65), or a homolog thereof (e.g., the formyltransferase from the PAK or LESB58 strain of *Pseudomonas aeruginosa*). In certain embodiments, one or more of the nucleic acids encoding the rfb cluster, the wzy polymerase, and/or the formyltransferase are inserted into the genome of the host cell, e.g., using a method described herein. In a specific embodiment, each of the nucleic acids encoding the rfb cluster, the wzy polymerase, and the formyltransferase are inserted into the genome of the host cell, e.g., using a method described herein. In certain embodiments, the host cell further comprises a nucleic acid encoding an oligosaccharyl transferase (e.g., pglB from *Campylobacter jejuni*), wherein said nucleic acid encoding an oligosaccharyl transferase is either plasmid-borne or integrated into the genome of the host cell; and a nucleic acid encoding a carrier protein, wherein said nucleic acid encoding said carrier protein is either plasmid-borne or integrated into the genome of the host cell. In a specific embodiment, said nucleic acid encoding said oligosaccharyl transferase is integrated into the genome of the host cell.

Genetic Background

Exemplary host cells that can be used to generate the modified host cells described herein include, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In a specific embodiment, the host cell used herein is *E. coli*.

In certain embodiments, the host cell genetic background is modified by, e.g., deletion of one or more genes. Exemplary genes that can be deleted in host cells (and, in some cases, replaced with other desired nucleic acid sequences) include genes of host cells involved in glycolipid biosynthesis, such as waaL (see, e.g., Feldman et al., 2005, PNAS USA 102:3016-3021), the O antigen cluster (rfb or wb), enterobacterial common antigen cluster (wec), the lipid A core biosynthesis cluster (waa), and prophage O antigen modification clusters like the gtrABS cluster. In a specific embodiment, the host cells described herein are modified such that they do not produce any O antigens other than a desired O antigen from, e.g., an O antigen *Pseudomonas*. In a specific embodiment, one or more of the waaL gene, gtrA gene, gtrB gene, gtrS gene, or a gene or genes from the wec cluster or a gene or genes from the rfb gene cluster are deleted or functionally inactivated from the genome of a prokaryotic host cell provided herein. In one embodiment, a host cell used herein is *E. coli*, wherein the waaL gene, gtrA gene, gtrB gene, gtrS gene are deleted or functionally inactivated from the genome of the host cell. In another embodiment, a host cell used herein is *E. coli*, wherein the waaL gene and gtrS gene are deleted or functionally inactivated from the genome of the host cell. In another embodiment, a host cell used herein is *E. coli*, wherein the waaL gene and genes from the wec cluster are deleted or functionally inactivated from the genome of the host cell.

Carrier Proteins

Any carrier protein suitable for use in the production of conjugate vaccines (e.g., bioconjugates for use in vaccines) can be used herein, e.g., nucleic acids encoding the carrier protein can be introduced into a host provided herein for the production of a bioconjugate comprising a carrier protein linked to *Pseudomonas* antigen. Exemplary carrier proteins include, without limitation, detoxified Exotoxin A of *P. aeruginosa* (EPA; see, e.g., Ihssen, et al., (2010) Microbial cell factories 9, 61), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin and detoxified variants thereof, *C. jejuni* AcrA, *Pseudomonas* PcrV protein, and *C. jejuni* natural glycoproteins. The PcrV protein is used in many embodiments of the invention.

In specific embodiments, the carrier proteins expressed by the modified host cells provided herein are expressed from a nucleic acid that has been integrated into the genome of the modified host cell. That is, a nucleic acid encoding the carrier protein has been integrated into the host cell genome. In certain embodiments, the carrier proteins expressed by the modified host cells provided herein are expressed from a plasmid that has been introduced into the modified host cell.

In certain embodiments, the carrier proteins used in the generation of the bioconjugates described herein are modified, e.g., modified in such a way that the protein is less toxic and/or more susceptible to glycosylation. In a specific embodiment, the carrier proteins used in the generation of the bioconjugates described herein are modified such that the number of glycosylation sites in the carrier proteins is maximized in a manner that allows for lower concentrations of the protein to be administered, e.g., in an immunogenic composition, in its bioconjugate form.

In certain embodiments, the carrier proteins described herein are modified to include 1, 2, 3, 4, 5, 6, 7, 8, 9, 10, or more glycosylation sites than would normally be associated with the carrier protein (e.g., relative to the number of glycosylation sites associated with the carrier protein in its native/natural, e.g., "wild-type" state). In specific embodiments, introduction of glycosylation sites is accomplished by insertion of glycosylation consensus sequences (e.g., Asn-X-Ser(Thr), wherein X can be any amino acid except Pro; or Asp(Glu)-X-Asn-Z-Ser(Thr), wherein X and Z are independently selected from any natural amino acid except Pro (see WO 2006/119987)) anywhere in the primary structure of the protein. Introduction of such glycosylation sites can be accomplished by, e.g., adding new amino acids to the primary structure of the protein (i.e., the glycosylation sites are added, in full or in part), or by mutating existing amino acids in the protein in order to generate the glycosylation sites (i.e., amino acids are not added to the protein, but selected amino acids of the protein are mutated so as to form glycosylation sites). Those of skill in the art will recognize that the amino acid sequence of a protein can be readily modified using approaches known in the art, e.g., recombinant approaches that include modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In certain embodiments, the classical 5 amino acid glycosylation consensus sequence may be extended by lysine residues for more efficient glycosylation, and thus the inserted consensus sequence may encode 5, 6, or 7 amino acids that should be inserted or that replace acceptor protein amino acids.

In certain embodiments, the carrier proteins used in the generation of the bioconjugates described herein comprise a "tag," i.e., a sequence of amino acids that allows for the isolation and/or identification of the carrier protein. For example, adding a tag to a carrier protein described herein can be useful in the purification of that protein and, hence, the purification of conjugate vaccines comprising the tagged carrier protein. Exemplary tags that can be used herein include, without limitation, histidine (HIS) tags (e.g., hexa histidine-tag, or 6×His-Tag), FLAG-TAG, and HA tags. In certain embodiments, the tags used herein are removable, e.g., removal by chemical agents or by enzymatic means, once they are no longer needed, e.g., after the protein has been purified.

In certain embodiments, the carrier proteins described herein comprise a signal sequence that targets the carrier protein to the periplasmic space of the host cell that expresses the carrier protein. In a specific embodiment, the signal sequence is from *E. coli* DsbA, *E. coli* outer membrane porin A (OmpA), *E. coli* maltose binding protein (MalE), *Erwinia* carotovorans pectate lyase (PelB), FlgI, NikA, or *Bacillus* sp. endoxylanase (XynA), heat labile *E. coli* enterotoxin LTIIb, *Bacillus* endoxylanase XynA, or *E. coli* flagellin (FlgI).

Glycosylation Machinery

Oligosaccharyl Transferases

Oligosaccharyl transferases transfer lipid-linked oligosaccharides to asparagine residues of nascent polypeptide chains that comprise an N-glycoxylation consensus motif, e.g., Asn-X-Ser(Thr), wherein X can be any amino acid except Pro; or Asp(Glu)-X-Asn-Z-Ser(Thr), wherein X and Z are independently selected from any natural amino acid except Pro (see WO 2006/119987). See, e.g., WO 2003/074687 and WO 2006/119987, the disclosures of which are herein incorporated by reference in their entirety.

In certain embodiments, the host cells provided herein comprise a nucleic acid that encodes an oligosaccharyl transferase. The nucleic acid that encodes an oligosaccharyl transferase can be native to the host cell, or can be introduced into the host cell using genetic approaches, as described above. The oligosaccharyl transferase can be from any source known in the art. In a specific embodiment, the oligosaccharyl transferase is an oligosaccharyl transferase from *Campylobacter*. In another specific embodiment, the oligosaccharyl transferase is an oligosaccharyl transferase from *Campylobacter jejuni* (i.e., pglB; see, e.g., Wacker et al., 2002, Science 298:1790-1793; see also, e.g., NCBI Gene ID: 3231775, UniProt Accession No. O86154). In another specific embodiment, the oligosaccharyl transferase is an oligosaccharyl transferase from *Campylobacter lari* (see, e.g., NCBI Gene ID: 7410986).

In a specific embodiment, the modified host cells provided herein comprise a nucleic acid sequence encoding an oligosaccharyl transferase, wherein said nucleic acid sequence encoding an oligosaccharyl transferase is integrated into the genome of the host cell.

Accessory Enzymes

In certain embodiments, nucleic acids encoding one or more accessory enzymes are introduced into the modified host cells described herein. Such nucleic acids encoding one or more accessory enzymes can be either plasmid-borne or integrated into the genome of the host cells described herein. Exemplary accessory enzymes include, without limitation, epimerases, branching, modifying, amidating, chain length regulating, acetylating, formylating, polymerizing enzymes.

Nucleic acid sequences encoding epimerases that can be inserted into the host cells described herein are known in the art. In certain embodiments, the epimerase inserted into a host cell described herein is an epimerase described in International Patent Application Publication No. WO 2011/062615, the disclosure of which is incorporated by reference herein in its entirety. In a specific embodiment, the epimerase is the epimerase encoded by the Z3206 gene of *E. coli* strain O157. See, e.g., WO 2011/062615 and Rush et al., 2009, The Journal of Biological Chemistry 285:1671-1680, which is incorporated by reference herein in its entirety. In a specific embodiment, the modified host cells provided herein comprise a nucleic acid sequence encoding an epimerase, wherein said nucleic acid sequence encoding an epimerase is integrated into the genome of the host cell.

In certain embodiments, a nucleic acid sequence encoding a formyltransferase is inserted into or expressed by the host cells described herein. Formyltransferases are enzymes that catalyse the transfer of a formyl group to an acceptor molecule. In a specific embodiment, a nucleic acid sequence encoding the *Pseudomonas aeruginosa* O6 formyltransferase fmtO6 (SEQ ID NO:65), or a homolog thereof, is inserted into or expressed by the host cells described herein. In another specific embodiment, a nucleic acid sequence that encodes a protein having about or at least 80%, 85%, 90%, 95%, 96%, 97%, 98%, or 99% identity or homology to SEQ ID NO:65 is inserted into or expressed by the host cells described herein.

Certain formyltransferases involved in polysaccharide biosynthesis are known, and can be inserted into or expressed by the host cells described herein. For example, vioF is an enzyme from *P. alcalifaciens* serotype O30, which is 48% identical to the formyltransferase from *Francisella tularensis* (Nagaraja et al. 2005). It converts dTDP-D-Qui4N to dTDP-D-Qui4NFo, and is involved in O-antigen biosynthesis (Liu et al. 2012, Glycobiology 22(9):1236-1244). Another formyltransferase involved in polysaccharide biosynthesis is amA (e.g., from *E. coli*), a bifunctional enzyme in which the N-terminal domain converts UDP-Ara4N to UDP-AraNFo, while the C-terminal domain is involved in oxidative decarboxylation of UDP-glucuronic acid. Both enzymatic activities are required for L-Ara4N modification of LipidA and polymyxin resistance (Breazeale et al., 2005, The Journal of Biological Chemistry 280(14): 14154-14167). Another formyltransferase involved in polysaccharide biosynthesis is wekD, an enzyme from *E. coli* serotype O119, involved in the biosynthesis of TDP-DRhaNAc3NFo (Anderson et al., 1992, Carbohydr Res. 237:249-62).

Further, domains that are related to formyltransferase activity have been characterized. The so called FMT_core domain is present in the majority of formyltransferases. Examples include the methionyl-tRNA formyltransferase, phosphoribosylglycinamide formyltransferase 1, UDP-glucuronic acid decarboxylase/UDP-4-amino-4-deoxy-L-arabinose formyltransferase, vioF from *Providencia alcalifaciens* O30, and amA from *E. coli*. The above mentioned formyltransferases use FTHF (N-10-formyltetrahydrofolate) as formyl donor. Also, formate producing enzymes using FTHF (10-formyltetrahydrofolate) as substrate contain this domain. In addition, AICARFT is present in phosphoribosylaminoimidazolecarboxamide formyltransferase/IMP cyclohydrolase and FDH_GDH is present in phosphoribosylglycinamide formyltransferase 2.

In certain embodiments, a nucleic acid sequence encoding an O antigen polymerase (wzy gene) is inserted into or expressed by the host cells described herein. O antigen polymerases are multi spanning transmembrane proteins. They use undecaprenylpyrophosphate bound O antigen repeat units as substrates to generate a linear polymer consisting of the repeat units. O antigen polymerases (wzy) are present in Gram negative bacteria that synthesize O antigen polymers via a wzy dependent mechanism.

In a specific embodiment, a nucleic acid sequence encoding the *Pseudomonas aeruginosa* wzy polymerase (SEQ ID NO:66), or a homolog thereof (e.g., the wzy polymerase from the PAK or LESB58 strain of *Pseudomonas aeruginosa*), is inserted into or expressed by the host cells described herein. Examples of bacteria known to comprise wzy polymerases include *Escherichia coli, Pseudomonas aeruginosa, Shigella flexneri* and *Salmonella typhimurium*. In another specific embodiment, a nucleic acid sequence that encodes a protein having about or at least 80%, 85%, 90%, 95%, 96%, 97%, 98%, or 99% identity or homology to SEQ ID NO:66 is inserted into or expressed by the host cells described herein.

Gene Copy Number

In certain embodiments, the copy number of a gene(s) integrated into a modified host cell provided herein is 1, 2, 3, 4, 5, 6, 7, 8, 9, or 10. In a specific embodiment, the copy number of a gene(s) integrated into a modified host cell provided herein is 1 or 2.

Benefits

The modified host cells described herein are of particular commercial importance and relevance, as they allow for large scale fermentation of bioconjugates comprising saccharide, for example, *Pseudomonas* antigens that can be used as therapeutics (e.g., in immunogenic compositions, vaccines), at a lower risk due to the increased stability of the chromosomally inserted DNA and thus expression of the DNA of interest during fermentation. The modified host cells described herein are advantageous over host cells that rely on plasmid borne expression of nucleic acids required for generation of the bioconjugates described herein because, inter alia, antibiotic selection during fermentation is not required once the heterologous DNA is inserted into the host cell genome. That is, when the insert DNA is inserted in the chromosome, it doesn't need to be selected for, because it is propagated along with replication of the host genome. Further, it is a known disadvantage in plasmid borne systems that with every generation (i.e., cycle of host cell replication) the risk for losing the plasmid increases. This loss of plasmid is due to the sometimes inappropriate distribution of plasmids to daughter cells at the stage of cell separation during cell division. At large scale, bacterial cell cultures duplicate more often than in smaller fermentation scales to reach high cell densities. Thus, higher cell stability and insert DNA expression leads to higher product yields, providing a distinct advantage. Cell stability is furthermore a process acceptance criteria for approval by regulatory authorities, while antibiotic selection is generally not desired during fermentation for various reasons, e.g., antibiotics present as impurities in the final medicinal products and bear the risk of causing allergic reactions, and antibiotics may promote antibiotic resistance (e.g., by gene transfer or selection of resistant pathogens).

The present application provides modified host cells for use in making bioconjugates comprising saccharide antigens that can be used as therapeutics (e.g., in immunogenic compositions, vaccines), wherein certain genetic elements required to drive the production of bioconjugates are integrated stably into the host cell genome. Consequently the host cell can contain a reduced number of plasmids, just a single plasmid or no plasmids at all. In some embodiments, the presence of a single plasmid can result in greater flexibility of the production strain and the ability to change the nature of the conjugation (in terms of its saccharide or carrier protein content) easily leading to greater flexibility of the production strain.

In general, a reduction in the use of plasmids leads to a production strain which is more suited for use in the production of medicinal products. A drawback of essential genetic material being present on plasmids is the requirement for selection pressure to maintain the episomal elements in the host cell. The selection pressure requires the use of antibiotics, which is undesirable for the production of medicinal products due to, e.g., the danger of allergic reactions against the antibiotics and the additional costs of manufacturing. Furthermore, selection pressure is often not complete, resulting in inhomogeneous bacterial cultures in which some clones have lost the plasmid and thus are not producing the bioconjugate. The host cells described herein therefore are able to produce a safer product that can be obtained in high yields.

Bioconjugates

The modified host cells described herein can be used to produce bioconjugates comprising a saccharide antigen, for example a *Pseudomonas* antigen linked to a carrier protein. Methods of producing bioconjugates using host cells are known in the art. See, e.g., WO 2003/074687 and WO 2006/119987. Bioconjugates, as described herein, have advantageous properties over chemical conjugates of antigen-carrier protein, in that they require less chemicals in manufacture and are more consistent in terms of the final product generated.

In a specific embodiment, provided herein is a bioconjugate comprising a carrier protein linked to a *Pseudomonas* antigen. In a specific embodiment, said *Pseudomonas* antigen is an O antigen of *Pseudomonas aeruginosa*. In a specific embodiment, provided herein is a bioconjugate comprising a *P. aeruginosa* O antigen and a carrier protein, wherein said carrier protein is EPA, PcrV (aka LcrV, EspA, SseB), PopB (YopB, YopD, FliC), or OprF, OprI. The exemplified embodiments use EPA and PcrV as carrier protein.

In a specific embodiment, provided herein is a bioconjugate comprising a carrier protein linked to a *Pseudomonas aeruginosa* O antigen, wherein said *Pseudomonas aeruginosa* O antigen is an O antigen from *Pseudomonas aeruginosa* serotype O1, O2, O3, O4, O5, O6, O7, O8, O9, O10, O11, O12, O13, O14, O15, O16, O17, O18, O19, or O20.

In a specific embodiment, provided herein is a bioconjugate comprising a carrier protein linked to a *Pseudomonas aeruginosa* O antigen, wherein said *Pseudomonas aeruginosa* O antigen is one of the serotypes described in Knirel et al., 2006, Journal of Endotoxin Research 12(6):324-336, the disclosure of which is incorporated herein by reference in its entirety.

In a specific embodiment, provided herein is a bioconjugate comprising a carrier protein linked to a *Pseudomonas aeruginosa* O antigen, wherein said *Pseudomonas aeruginosa* O antigen is an O antigen from *Pseudomonas aeruginosa* serotype O6.

In a specific embodiment, provided herein is a bioconjugate comprising a carrier protein linked to a *Pseudomonas aeruginosa* O antigen, wherein said *Pseudomonas aeruginosa* O antigen is an O antigen from *Pseudomonas aeruginosa* serotype O11. In a specific embodiment, said O antigen from *Pseudomonas aeruginosa* serotype O11 is from *Pseudomonas aeruginosa* strain PA103 (see, e.g., Genbank Accession No. KF364633.1).

The bioconjugates described herein can be purified by any method known in the art for purification of a protein, for example, by chromatography (e.g., ion exchange, anionic exchange, affinity, and sizing column chromatography), centrifugation, differential solubility, or by any other standard technique for the purification of proteins. See, e.g., Saraswat et al., 2013, Biomed. Res. Int. ID #312709 (p. 1-18); see also the methods described in WO 2009/104074. Further, the bioconjugates may be fused to heterologous polypeptide sequences described herein or otherwise known in the art to facilitate purification. The actual conditions used to purify a particular bioconjugate will depend, in part, on the synthesis strategy and on factors such as net charge, hydrophobicity, and/or hydrophilicity of the bioconjugate, and will be apparent to those having skill in the art.

Analytical Methods

Various methods can be used to analyze the structural compositions and sugar chain lengths of the bioconjugates described herein.

In one embodiment, hydrazinolysis can be used to analyze glycans. First, polysaccharides are released from their protein carriers by incubation with hydrazine according to the manufacturer's instructions (Ludger Liberate Hydrazinolysis Glycan Release Kit, Oxfordshire, UK). The nucleophile hydrazine attacks the glycosidic bond between the polysaccharide and the carrier protein and allows release of the attached glycans. N-acetyl groups are lost during this treatment and have to be reconstituted by re-N-acetylation. The free glycans are purified on carbon columns and subsequently labeled at the reducing end with the fluorophor 2-amino benzamide. See Bigge J C, Patel T P, Bruce J A, Goulding P N, Charles S M, Parekh R B: Nonselective and efficient fluorescent labeling of glycans using 2-amino benzamide and anthranilic acid. Anal Biochem 1995, 230(2): 229-238. The labeled polysaccharides are separated on a GlycoSep-N column (G L Sciences) according to the HPLC protocol of Royle et al. See Royle L, Mattu T S, Hart E, Langridge J I, Merry A H, Murphy N, Harvey D J, Dwek R A, Rudd P M: An analytical and structural database provides a strategy for sequencing O-glycans from microgram quantities of glycoproteins. Anal Biochem 2002, 304(1):70-90. The resulting fluorescence chromatogram indicates the polysaccharide length and number of repeating units. Structural information can be gathered by collecting individual peaks and subsequently performing MS/MS analysis. Thereby the monosaccharide composition and sequence of the repeating unit could be confirmed and additionally in homogeneity of the polysaccharide composition could be identified.

In another embodiment, SDS-PAGE or capillary gel electrophoresis can be used to assess glycans and bioconjugates. Polymer length for the O antigen glycans is defined by the number of repeat units that are linearly assembled. This means that the typical ladder like pattern is a consequence of different repeat unit numbers that compose the glycan. Thus, two bands next to each other in SDS PAGE or other techniques that separate by size differ by only a single repeat unit. These discrete differences are exploited when analyzing glycoproteins for glycan size: The unglycosylated carrier protein and the bioconjugate with different polymer chain lengths separate according to their electrophoretic mobilities. The first detectable repeating unit number ($n_1$) and the average repeating unit number ($n_{average}$) present on a bioconjugate are measured. These parameters can be used to demonstrate batch to batch consistency or polysaccharide stability.

In another embodiment, high mass MS and size exclusion HPLC could be applied to measure the size of the complete bioconjugates.

In another embodiment, an anthrone-sulfuric acid assay can be used to measure polysaccharide yields. See Leyva A, Quintana A, Sanchez M, Rodriguez E N, Cremata J, Sanchez J C: Rapid and sensitive anthrone-sulfuric acid assay in microplate format to quantify carbohydrate in biopharmaceutical products: method development and validation. Biologicals: journal of the International Association of Biological Standardization 2008, 36(2):134-141. In another embodiment, a Methylpentose assay can be used to measure polysaccharide yields. See, e.g., Dische et al., J Biol Chem. 1948 September; 175(2):595-603.

Change in Glycosylation Site Usage

To show that the site usage in a specific protein is changed in a multiple plasmid system as opposed to an inserted system, the glycosylation site usage must be quantified. Methods to do so are listed below.

Glycopeptide LC-MS/MS: bioconjugates are digested with protease(s), and the peptides are separated by a suitable chromatographic method (C18, Hydriphilic interaction HPLC HILIC, GlycoSepN columns, SE HPLC, AE HPLC), and the different peptides are identified using MS/MS. This method can be used with our without previous sugar chain shortening by chemical (smith degradation) or enzymatic methods. Quantification of glycopeptide peaks using UV detection at 215 to 280 nm allow relative determination of glycosylation site usage.

Size exclusion HPLC: Higher glycosylation site usage is reflected by a earlier elution time from a SE HPLC column.

Homogeneity

Bioconjugate homogeneity (i.e., the homogeneity of the attached sugar residues) can be assessed using methods that measure glycan length and hydrodynamic radius.

Other Potential Clinical/Practical Applications

Integrated strains can make a higher yield of bioconjugates due to the reduced antibiotic selection burden as compared to the three plasmid system. In addition, less proteolytic degradation occurs due to reduced metabolic burden to the cells.

Integrated strains make bioconjugates with shorter, less spread polysaccharide length distributions. Thus, the bioconjugates are easier to characterize and are better defined. In addition, insertion may reduce the extent of periplasmic stress to the cells which may lead to less proteolysis of product during the fermentation process due to the reduced antibiotic selection burden as compared to the three plasmid system.

Protein glycosylation systems require three recombinant elements in the production host: a carrier protein expression DNA, an oligosaccharyl transferase expression DNA, and a polysaccharide expression DNA. Prior art bacterial production systems contain these three elements on plasmids. Thus, there is a risk for instability during manufacture due to plasmid loss, particularly because antibiotics used for maintenance of the plasmids mustn't be present during fermentation of GMP material. Since inserted strains contain one plasmid less, they are more stable over many generations. This means that higher scale fermentations and longer incubation times (higher generation numbers) are more feasible. In addition, the absence of an antibiotic for selection makes a safer product, due to the absence of trace antibiotics which can cause allergic reactions in sensitive subjects. See COMMITTEE WE, BIOLOGICAL O, STANDARDIZATION: WHO Technical Report Series 941. In: Fifty-sixth Report. Edited by Organization W H. Geneva: World Health Organization; 2007.

Inserted strains are more genetically stable due to the fixed chromosomal insertion, thus leading to higher reproducibility of desired protein products during the production process, e.g., during culture of host cell comprising inserted heterologous DNA.

Analytical Methods for Testing Benefit

Yield. Yield is measured as carbohydrate amount derived from a liter of bacterial production culture grown in a bioreactor under controlled and optimized conditions. After purification of bioconjugate, the carbohydrate yields can be directly measured by either the anthrone assay or ELISA using carbohydrate specific antisera. Indirect measurements are possible by using the protein amount (measured by well known BCA, Lowry, or bardford assays) and the glycan length and structure to calculate a theoretical carbohydrate amount per gram of protein. In addition, yield can also be measured by drying the glycoprotein preparation from a volatile buffer and using a balance to measure the weight.

Homogeneity. Homogeneity means the variability of glycan length and possibly the number of glycosylation sites. Methods listed above can be used for this purpose. SE-HPLC allows the measurement of the hydrodynamic radius. Higher numbers of glycosylation sites in the carrier lead to higher variation in hydrodynamic radius compared to a carrier with less glycosylation sites. However, when single glycan chains are analyzed, they may be more homogenous due to the more controlled length. Glycan length is measured by hydrazinolysis, SDS PAGE, and CGE. In addition, homogeneity can also mean that certain glycosylation site usage patterns change to a broader/narrower range. These factors can be measured by Glycopeptide LC-MS/MS.

Strain stability and reproducibility. Strain stability during bacterial fermentation in absence of selective pressure is measured by direct and indirect methods that confirm presence or absence of the recombinant DNA in production culture cells. Culture volume influence can be simulated by elongated culturing times meaning increased generation times. The more generations in fermentation, the more it is likely that a recombinant element is lost. Loss of a recombinant element is considered instability. Indirect methods rely on the association of selection cassettes with recombinant DNA, e.g. the antibiotic resistance cassettes in a plasmid. Production culture cells are plated on selective media, e.g. LB plates supplemented with antibiotics or other chemicals related to a selection system, and resistant colonies are considered as positive for the recombinant DNA associated to the respective selection chemical. In the case of a multiple plasmid system, resistant colonies to multiple antibiotics are counted and the proportion of cells containing all three resistances is considered the stable population. Alternatively, quantitative PCR can be used to measure the amount of recombinant DNA of the three recombinant elements in the presence, absence of selection, and at different time points of fermentation. Thus, the relative and absolute amount of recombinant DNA is measured and compared.

Reproducibility of the production process is measured by the complete analysis of consistency batches by the methods stated in this application.

In an embodiment, there is provided a host cell wherein the nucleic acid that encodes a glycosyltransferase is derived from an rfb cluster of *Pseudomonas*, wherein said nucleic acid is optionally stably inserted into the genome of the host cell. The rfb cluster is optionally from *Pseudomonas aeruginosa*, optionally serotype O6 or O11.

In an embodiment, the host cell comprises an oligosaccharyl transferase derived from *Campylobacter*, for example wherein the oligosaccharyl transferase is PglB of *C. jejuni*.

In an embodiment, the host cell comprises the nucleic acid that encodes a *P. aeruginosa* PcrV protein in a plasmid in the host cell.

In an embodiment, the host cell further comprises a formyltranferase enzyme, wherein said nucleic acid encodes a protein having about or at least 80%, 85%, 90%, 95%, 96%, 97%, 98%, or 99% identity or homology to SEQ ID NO:65, or wherein said nucleic acid encodes SEQ ID NO:65.

In an embodiment, the host cell of the invention, further comprising a nucleic acid that encodes a wzy polymerase, wherein said nucleic acid encodes a protein having about or at least 80%, 85%, 90%, 95%, 96%, 97%, 98%, or 99% identity or homology to SEQ ID NO:66, or wherein said nucleic acid encodes SEQ ID NO:66.

In an embodiment, he host cell comprises the nucleic acid encoding a formyltransferase enzyme and/or the nucleic acid encoding a wzy polymerase which are stably inserted into the genome of the host cell. Optionally, a gene encoding a formyltransferase enzyme and/or a gene encoding a wzy polymerase is present on a plasmid in the host cell.

In an embodiment, the host cell is *E. coli*.

A further aspect of the invention is a method of producing a bioconjugate that comprises a *P. aeruginosa* PcrV protein linked to a saccharide, said method comprising culturing the host cell of the invention under condtions suitable for the production of proteins.

A further aspect of the invention is a bioconjugate produced by the process of the invention, wherein said bioconjugate comprises a saccharide linked to a *P. aeruginosa* PcrV protein.

The terms "comprising", "comprise" and "comprises" herein are intended by the inventors to be optionally substitutable with the terms "consisting of", "consist of" and "consists of", respectively, in every instance.

The term "wherein the asparagine residue is situated at a position equivalent to between amino acids . . . of SEQ ID NO: . . . " is defined as the asparagine residue being introduced into an amino acid sequence at the position that would be equivalent to the defined position if the reference sequence and the mutated sequence were lined up to maximise the sequence identity between the two sequences. The addition or deletion of amino acids from the mutated sequence could lead to a difference in the actual amino acid position of the asparagine residue in the mutated sequence, however, by lining the mutated sequence up with the reference sequence, the appropriate position for insertion of the asparagine amino acid can be established.

The term "the peptide comprising the D/E-X-N-X-S/T consensus sequence is situated at a position between amino acids . . . of SEQ ID NO: . . . " is defined as the consensus sequence being introduced into an amino acid sequence at the position that would be equivalent to the defined position, if the reference sequence and the mutated sequence were lined up to maximise the sequence identity between the two sequences. The addition or deletion of amino acids from the mutated sequence could lead to a difference in the actual amino acid position of the consensus sequence in the mutated sequence, however, by lining the mutated sequence up with the reference sequence, the appropriate position for insertion of the consensus sequence can be established.

The O-antigens of *P. aeruginosa* (O-1 to O20) are according to the classification of serotypes according to the IATS nomenclature.

All references or patent applications cited within this patent specification are incorporated by reference herein.

In order that this invention may be better understood, the following examples are set forth. These examples are for purposes of illustration only, and are not to be construed as limiting the scope of the invention in any manner.

---

```
                 Sequences of proteins and nucleic acids
       SEQ ID NO: 1-PcrV protein wild type sequence
       MEVRNLNAARELFLDELLAASAAPASAEQEELLALLRSERIVLAHAGQPLSEAQVLKALA
       WLLAANPSAPPGQGLEVLREVLQARRQPGAQWDLREFLVSAYFSLHGRLDEDVIGVYK
       DVLQTQDGKRKALLDELKALTAELKVYSVIQSQINAALSAKQGIRIDAGGIDLVDPTLYGYA
       VGDPRWKDSPEYALLSNLDTFSGKLSIKDFLSGSPKQSGELKGLSDEYPFEKDNNPVGN
       FATTVSDRSRPLNDKVNEKTTLLNDTSSRYNSAVEALNRFIQKYDSVLRDILSAI
```

-continued

SEQ ID NO: 2-PcrV
AKDQNATKVRNLNAARELFKDQNATKDELLAASKDQNATKAPASAEQEELLALLRSERIV
LAHAGQPLSEAQVLKALAWLLAANPSAPPGQGLEVLREVLQARRQPGAQWDLREFLVS
AYFSLHGRLDEDVIGVYKDVLQTQDGKRKALLDELKALTAELKVYSVIQSQINAALSAKQG
IRIDAGGIDLVDPTLYGYAVGDPRWKDSPEYALLSNLDTFSGKLSIKDFLSGSPKQSGELK
GLSDEYPFEKDNNPVGNFATTVSDRSRPLNDKVNEKTTLLNDTSSRYNSAVEALNRFIQ
KYDSVLRDILSAI

SEQ ID NO: 3
MSFKKIIKAFVIMAALVSVQAHAAEVRNLNAARELFLDELLAASAAPASAEQEELLALLRSE
RIVLAHAGQPLSEAQVLKALAWLLAANPSAPPGQGLEVLREVLQARRQPGAQWDLREFL
VSAYFSLHGRLDEDVIGVYKDVLQTQDGKRKALLDELKALTAELKVYSVIQSQINAALSAK
QGIRIDAGGIDLVDPTLYGYAVGDPRWKDSPEYALLSNLDTFSGKLSIKDFLSGSPKQSG
ELKGLSDEYPFEKDNNPVGNFATTVSDRSRPLNDKVNEKTTLLNDTSSRYNSAVEALNR
FIQKYDSVLRDILSAI

SEQ ID NO: 4-mature
AEVRNLNAARELFLDELLAASAAPASAEQEELLALLRSERIVLAHAGQPLSEAQVLKALA
WLLAANPSAPPGQGLEVLREVLQARRQPGAQWDLREFLVSAYFSLHGRLDEDVIGVYK
DVLQTQDGKRKALLDELKALTAELKVYSVIQSQINAALSAKQGIRIDAGGIDLVDPTLYGYA
VGDPRWKDSPEYALLSNLDTFSGKLSIKDFLSGSPKQSGELKGLSDEYPFEKDNNPVGN
FATTVSDRSRPLNDKVNEKTTLLNDTSSRYNSAVEALNRFIQKYDSVLRDILSAI SEQ ID NO: 5-epitope sequence
VYSVIQSQINAALSAKQGIRIDAGGIDLVDPTLYGYAVGDPRWKDSPEYALLSNLDTFSGK
LSIKDFLSGSPKQSGELKGLSDEYPFEKDNNPVGNFATTVSDRSRPLNDKVNE

SEQ ID NO: 6
AKDQNATKVRNLNAARELF

SEQ ID NO: 7
VRNKDQNATKNAARELF

SEQ ID NO: 8
VRNLNAAKDQNATKELF

SEQ ID NO: 9
ELFKDQNATKDELLAAS

SEQ ID NO: 10
DELKDQNATKAAS

SEQ ID NO: 11
DELLAASKDQNATKAP

SEQ ID NO: 12
APKDQNATKSAEQEEL

SEQ ID NO: 13
ALLRSEKDQNATKI

SEQ ID NO: 14
ALLRSERIKDQNATKLAH

SEQ ID NO: 15
LAHKDQNATKGQPL

SEQ ID NO: 16
GQPLKDQNATKEAQVLKA

SEQ ID NO: 17
EAKDQNATKVLKALA

SEQ ID NO: 18
VLKALAKDQNATKLLAA

SEQ ID NO: 19
VLKALAWKDQNATKLAA

SEQ ID NO: 20
LAAKDQNATKPSA

SEQ ID NO: 21
PSAKDQNATKPGQG

SEQ ID NO: 22
PSAPPKDQNATKQG

-continued

SEQ ID NO: 23
QGKDQNATKEVLR

SEQ ID NO: 24
QGLEKDQNATKLR

SEQ ID NO: 25
LRKDQNATKVLQAR

SEQ ID NO: 26
VLGARKDQNATKQ

SEQ ID NO: 27
VLGARRQKDQNATKGAQW

SEQ ID NO: 28
VLQARRQPGKDQNATKQW

SEQ ID NO: 29
QWKDQNATKLREFLVSAYF

SEQ ID NO: 30
LREFLVSAYFSLKDQNATKG

SEQ ID NO: 31
GKDQNATKLDEDVIGVYKD

SEQ ID NO: 32
KDVLQTKDQNATKDGKRKAL

SEQ ID NO: 33
KYDSVLRDILSAKDQNATK

SEQ ID NO: 34
MSFKKIIKAFVIMAALVSVQAHA

SEQ ID NO: 35
AXD/EXNXS/TXVRNLNAARELF

SEQ ID NO: 36
VRNXD/EXNXS/TXNAARELF

SEQ ID NO: 37
VRNLNAAXD/EXNXS/TXELF

SEQ ID NO: 38
ELFXD/EXNXS/TXDELLAAS

SEQ ID NO: 39
DELXD/EXNXS/TXAAS

SEQ ID NO: 40
DELLAASXD/EXNXS/TXAP

SEQ ID NO: 41
APXD/EXNXS/TXSAEQEEL

SEQ ID NO: 42
ALLRSEXD/EXNXS/TXI

SEQ ID NO: 43
ALLRSERIXD/EXNXS/TXLAH

SEQ ID NO: 44
LAHXD/EXNXS/TXGQPL

SEQ ID NO: 45
GQPLXD/EXNXS/TXEAQVLKA

SEQ ID NO: 46
EAXD/EXNXS/TXVLKALA

SEQ ID NO: 47
VLKALAXD/EXNXS/TXLLAA

SEQ ID NO: 48
VLKALAWXD/EXNXS/TXLAA

```
SEQ ID NO: 49
LAAXD/EXNXS/TXPSA

SEQ ID NO: 50
PSAXD/EXNXS/TXPGQG

SEQ ID NO: 51
PSAPPXD/EXNXS/TXQG

SEQ ID NO: 52
QGXD/EXNXS/TXEVLR

SEQ ID NO: 53
QGLEXD/EXNXS/TXLR

SEQ ID NO: 54
LRXD/EXNXS/TXVLQAR

SEQ ID NO: 55
VLGARXD/EXNXS/TXQ

SEQ ID NO: 56
VLGARRQXD/EXNXS/TXGAQW

SEQ ID NO: 57
VLQARRQPGXD/EXNXS/TXQW

SEQ ID NO: 58
QWXD/EXNXS/TXLREFLVSAYF

SEQ ID NO: 59
LREFLVSAYFSLXD/EXNXS/TXG

SEQ ID NO: 60
GXD/EXNXS/TXLDEDVIGVYKD

SEQ ID NO: 61
KDVLQTXD/EXNXS/TXDGKRKAL

SEQ ID NO: 62
KYDSVLRDILSAKDQNATK

SEQ ID NO: 63
MSFKKIIKAFVIMAALVSVQAHA

SEQ ID NO: 64
D/E-X-N-X-S/T

SEQ ID NO: 65-formyltransferase
Met Ser Trp Gln Leu Phe Ser Glu Lys Cys Arg Phe Leu Gly Ala Val
Glu Ile Ser Gln His Phe Trp Gly Phe Ile Val Leu Glu Ala Ser Phe
Gly Met Lys Ile Lys Ala Ala Leu Ile Val Asp Asp Leu Ser Leu Ser
Glu Trp Gln Lys Arg Ala Ile Glu Asp Ser Ser Glu Tyr Leu Asp Ile
Gln Leu Val Leu Ser Cys Arg Asn Ser Ala Thr Lys Lys Ser Val Ile
Lys His Cys Gly Tyr Tyr Phe Leu Asn Ile Leu Ser Leu Lys Asn Asp
Met Thr Arg Arg Val Gln Leu Asp Ser Arg Gly Ser Glu Val Ile His
Phe Asp Ser Asp Tyr Glu Gly Ala Trp Gln Arg Ile Pro Glu Asp Val
Cys Ala Arg Ile Leu Asp Lys Gly Ile Lys Leu Val Ile Lys Phe Gly
Met Ser Leu Leu Arg Ile Asp Gly Gly Leu Gln Arg Leu Asp Ile Leu
Ser Tyr His His Gly Asp Pro Glu Tyr Tyr Arg Gly Arg Pro Ala Gly
Phe Tyr Glu Ile Tyr Glu Asn Ala Asp Ser Val Gly Ile Ile Val Gln
Lys Leu Ser Asn Lys Leu Asp Ala Gly Glu Val Leu Val Arg Gly Tyr
Ser Lys Val His His His Ser Tyr Lys Lys Thr Ser Arg Asn Phe Tyr
Leu Asn Ser Val Val Leu Leu Arg Lys Ala Leu Val Asn Tyr Ser Arg
Gly Glu Gln Val Val Leu Glu Lys Leu Gly Lys Asn Tyr Arg Leu Pro
Ser Asn Phe Thr Val Phe Lys Phe Phe Cys Lys Thr Ile Phe Arg Gly
Leu Ala Arg Leu Ser Tyr Gly Ala Phe Phe Glu Lys Lys Trp Asn Val
Val Ala Leu Pro Tyr Asn Asp Ile Pro Ser Leu Gln Glu Leu Ser Val
Ser Ala Gly Lys Ile Pro Lys Val Glu Lys Gly Tyr Thr Phe Tyr Ala
Asp Pro Phe Phe Ser Ala Asp Gly Lys Leu Ile Arg Leu Glu Ala Leu
Asn Ala Ser Asn Gly Leu Gly Glu Ile Ile Glu Leu Lys Ala Gln Ser
Leu Asp Phe Ser Arg Val Ile Leu Lys Gly Asn His Phe Ser Tyr Pro
Tyr Ser Phe Glu Ala Ser Gly Val Glu Tyr Leu Ile Pro Glu Val Ala
Ser His Ser Ala Pro Cys Leu Leu Pro Pro Pro Phe Ala Leu Glu Ser
Lys Lys Leu Phe Gln Gly Met Glu Gly Glu Arg Ile Leu Asp Gly Thr
Leu Phe Glu His Gly Gly Arg Tyr Tyr Leu Phe Cys Gly Gln Ala Val
Ser Gly Ser Asp Asn Leu Tyr Leu Tyr Val Gly Glu Ser Leu Glu Gly
Pro Tyr Thr Ser His Pro Cys Asn Pro Val Val Met Asn Pro Gly Ser
Ala Arg Met Gly Gly Arg Ile Phe Lys Glu Gly Gly Lys Leu Tyr Arg
```

-continued

```
Phe Gly Gln Asn Asn Ser Tyr Gly Tyr Gly Ser Ser Leu Ala Val Asn
Glu Ile Glu Val Leu Asp Pro Glu His Tyr Ser Glu Lys Arg Val Ala
Asn Leu Ala Phe Gln Asp Ala Arg Gly Pro His Thr Ile Asp Ile His
Gly Gln Thr Met Ile Leu Asp Phe Tyr Gln Asp Arg Phe Ser Leu Leu
Ala Gly Tyr Arg Arg Leu Val Ala Arg Leu Leu Ser Arg Gly

SEQ ID NO: 66 wzy polymerase
Met Tyr Ala Met Leu Thr Gly Ala Thr Leu Leu Ile Phe Ala Val Ala
Ala Arg Leu Leu Ala Arg Ser Ala Ile His Pro Ser Val Ala Met Pro
Ile Thr Trp Gly Leu Gly Leu Ile Gly Val Ser Leu Ala Ser Leu Ile
Gly Phe Tyr Arg Val Glu Ser Asp Ala Leu Leu Ile Phe Leu Phe Gly
Val Met Ser Phe Ser Leu Ser Ala Gly Cys Phe Ser Phe Leu Tyr Asn
Gly Tyr Phe Arg Ala Pro Ser Ser Asn Phe Leu Phe Asp Ser Glu Leu
Arg Thr Arg Ala Leu Val Ile Phe Phe Cys Leu Ala His Ile Val Phe
Leu Thr Val Ile Tyr Arg Asp Leu Ser Ser Ile Ala Pro Thr Leu Arg
Glu Ala Ala Tyr Met Ala Arg Ala Gln Ser Val Ser Gly Glu Pro Val
Leu Ser Ser Leu Ser Met Asn Tyr Leu Gln Leu Gly Gln Thr Val Ile
Pro Leu Val Val Leu Leu Tyr Arg Gly Lys Cys Gly Val Leu Gly
Phe Leu Ala Ile Ser Val Pro Trp Met Gly Val Ile Leu Leu Ala Ser
Gly Arg Ala Ser Leu Met Gln Met Leu Val Gly Leu Phe Phe Ile Tyr
Ile Leu Val Lys Gly Ser Pro Ser Leu Lys Ser Leu Leu Val Ile Gly
Leu Ala Met Phe Leu Val Ile Ala Val Gly Ala Val Ala Thr Ser Lys
Ile Gln Phe His Glu Gly Asp Gly Ile Ser Thr Leu Phe Ile Glu Leu
Tyr Arg His Val Ala Gly Tyr Ala Leu Gln Gly Pro Val Leu Phe Asp
Arg Tyr Tyr Gln Gly Ser Ile His Leu Glu Pro Tyr Trp Ser Pro Leu
Asn Gly Phe Cys Ser Ile Leu Ala Thr Val Gly Leu Cys Gln Lys Pro
Pro Leu His Leu Asp Phe Tyr Glu Tyr Ala Pro Gly Glu Leu Gly Asn
Val Tyr Ser Met Phe Phe Ser Met Tyr Pro His Tyr Gly Ala Leu Gly
Val Ile Gly Val Met Ala Leu Tyr Gly Met Leu Cys Ser Tyr Ala Tyr
Cys Lys Ala Lys Lys Gly Ser Leu Tyr Phe Thr Val Leu Ser Ser Tyr
Leu Phe Ser Ala Ile Val Phe Ser Leu Phe Ser Asp Gln Ile Ser Thr
Ser Trp Trp Phe Tyr Val Lys Met Thr Ile Ile Leu Gly Ile Leu Cys
Phe Val Phe Arg Arg Asp Arg Met Phe Val Ile Arg Leu Pro Gln Ala
Gly SEQ ID NO: 67-nucleotide sequence of PcrV
ATGGAAGTCAGAAACCTTAATGCCGCTCGCGAGCTGTTCCTGGACGAGCTCCTGGC
CGCGTCGGCGGCGCCTGCCAGTGCCGAGCAGGAGGAACTGCTGGCCCTGTTGCGC
AGCGAGCGGATCGTGCTGGCCCACGCCGGCCAGCCGCTGAGCGAGGCGCAAGTG
CTCAAGGCGCTCGCCTGGTTGCTCGCGGCCAATCCGTCCGCGCCTCCGGGGCAGG
GCCTCGAGGTACTCCGCGAAGTCCTGCAGGCACGTCGGCAGCCCGGTGCGCAGTG
GGATCTGCGCGAGTTCCTGGTGTCGGCCTATTTCAGCCTGCACGGGCGTCTCGACG
AGGATGTCATCGGTGTCTACAAGGATGTCCTGCAGACCCAGGACGGCAAGCGCAAG
GCGCTGCTCGACGAGCTCAAGGCGCTGACCGCGGAGTTGAAGGTCTACAGCGTGAT
CCAGTCGCAGATCAACGCCGCGCTGTCGGCCAAGCAGGGCATCAGGATCGACGCT
GGCGGTATCGATCTGGTCGACCCCACGCTATATGGCTATGCCGTCGGCGATCCCAG
GTGGAAGGACAGCCCCGAGTATGCGCTGCTGAGCAATCTGGATACCTTCAGCGGCA
AGCTGTCGATCAAGGATTTTCTCAGCGGCTCGCCGAAGCAGAGCGGGGAACTCAAG
GGCCTCAGCGATGAGTACCCCTTCGAGAAGGACAACAACCCGGTCGGCAATTTCGC
CACCACGGTGAGCGACCGCTCGCGTCCGCTGAACGACAAGGTCAACGAGAAGACC
ACCCTGCTCAACGACACCAGCTCCCGCTACAACTCGGCGGTCGAGGCGCTCAACCG
CTTCATTCAGAAATACGACAGCGTCCTGCGCGACATTCTCAGCGCGATCTAG

SEQ ID NO: 68
X-S/T-X-N-X-D/E
```

EXAMPLES

Example 1: Bacterial Strains with an Inserted Oligosaccharyl Transferase and an Inserted rfb Cluster are Stable and Produce Bioconjugates This example demonstrates that bioconjugates can successfully be produced by a bacterial host strain that has been genetically modified by insertion of (i) a nucleic acid encoding an oligosaccharyl transferase and (ii) a nucleic acid encoding an rfb cluster.

Modified *E. coli* host cells were generated by inserting the following directly into the host cell genome: (i) a nucleic acid encoding the *C. jejuni* oligosaccharyl transferase (PglB) and (ii) a nucleic acid encoding the rfb cluster from *Pseudomonas aeruginosa* strain PA103. This rfb cluster encodes genes necessary for O-antigen synthesis of the *Pseudomonas aeruginosa* serogroup O11 antigen. The insertions were performed using the novel insertion method described in PCT/EP2013/071328 (see Section 5.2, above) or the pUT mini system (Biomedal Lifescience). The insertion method described in PCT/EP2013/071328 is site-specific and utilizes homologous recombination, whereas the pUT mini system is a random, transposon-mediated approach that results in a nucleic acid sequence of interest being randomly inserted into a host cell genome. The *E. coli* host cells further were modified by introduction of a plasmid that expresses detoxified *Pseudomonas* extotoxin A (EPA) as a carrier protein into the host cells. Thus, the modified *E. coli* host cells described in this example express (i) the *C. jejuni* oligosaccharyl transferase (PglB), by virtue of integration of a nucleic acid encoding the oligosaccharyl transferase into the host cell genome; (ii) genes of a *Pseudomonas aeruginosa* rfb cluster that produce the O11 antigen, by virtue of integration of a nucleic acid encoding the rfb cluster from *Pseudomonas aeruginosa* strain PA103 into the host cell genome; and (iii) the EPA carrier protein, by virtue of transforming the host cell with a plasmid comprising a nucleic acid encoding the carrier protein.

Additional modified *E. coli* host cells were generated to allow for comparison of the ability of the modified host cells comprising double integrations (integration of an oligosaccharyl transferase and integration of an rfb cluster) to produce bioconjugates (EPA-O11) with bioconjugate production by host cells having (i) only a single integration of the oligosaccharyl transferase or the rfb cluster and the remaining components (carrier protein and oligosaccharyl transferase or rfb cluster) plasmid expressed by the host cell; or (ii) no integrated components, with all components (carrier protein and oligosaccharyl transferase and rfb cluster) plasmid expressed.

Three different *E. coli* background strains were used in the analysis: (i) "St4167" (W3110 ΔwaaL, ΔrfbO16::rfbP.a.O11), which comprises a deletion of the *E. coli* waaL gene, a deletion of the *E. coli* O16 rfb cluster, and an insertion of the *P. aeruginosa* O11 rfb cluster (PCT/EP2013/071328); (ii) "St1128" (W3110 ΔwaaL), which comprises a deletion of the *E. coli* waaL gene; and (iii) "St1935" (W3110 ΔwaaL, ΔwzzE-wecG, ΔwbbIJK), which comprises deletion of the indicated genes. For insertion of the *P. aeruginosa* O11 rfb cluster in St4167, O11 rfb cluster was cloned into the pDOC plasmid and the method according to PCT/EP2013/071328 was employed. The St4167 strains represent the double integration strains.

The specific plasmids utilized to introduce EPA into the host cell strains are designated "p1077" and "p150." The latter is described in Ihssen, et al., (2010) Microbial cell factories 9, 61, and the plasmids are the same with the exception of the fact that p1077 replaces the Amp cassette of p150 with a Kan cassette.

The following St4167 variants were generated: (i) St4167 with pglB inserted in place of the host cell yahL gene (by the method of PCT/EP2013/071328) and EPA expressed by plasmid p1077; (ii) St4167 with pglB inserted in place of the host cell ompT gene (using the pUT mini system) and EPA expressed by plasmid p150; (iii) St4167 with pglB expressed by plasmid p1769 (pglB in pDOC) and EPA expressed by plasmid p1077; (iv) St4167 with pglB expressed by plasmid p939 (pEXT21 based expression plasmid for PglB with an HA tag, codon optimized) and EPA expressed by plasmid p1077; and (v) St4167 with pglB expressed by plasmid p1762 (pglB in pDOC) and EPA expressed by plasmid p1077.

The following St1128 variants were generated: (i) St1128 with pglB expressed by plasmid p939, *P. aeruginosa* O11 rfb cluster expressed by plasmid p164 (pLAFR plasmid engineered to contain the *P. aeruginosa* O11 rfb cluster), and EPA expressed by plasmid p1077; and (ii) St1128 with pglB inserted in place of the host cell yahL gene (by the method of PCT/EP2013/071328), *P. aeruginosa* O11 rfb cluster expressed by plasmid p164, and EPA expressed by plasmid p1077.

The following St1935 variants were generated: (i) St1935 with pglB inserted in place of the host cell ompT gene (by the method of PCT/EP2013/071328), *P. aeruginosa* O11 rfb cluster expressed by plasmid p164, and EPA expressed by plasmid p1077; (ii) St1935 with pglB inserted in place of the host cell yahL gene (by the method of PCT/EP2013/071328), *P. aeruginosa* O11 rfb cluster expressed by plasmid p164, and EPA expressed by plasmid p1077; and St1935 with pglB expressed by plasmid p939, *P. aeruginosa* O11 rfb cluster expressed by plasmid p164, and EPA expressed by plasmid p1077.

Figure 1:
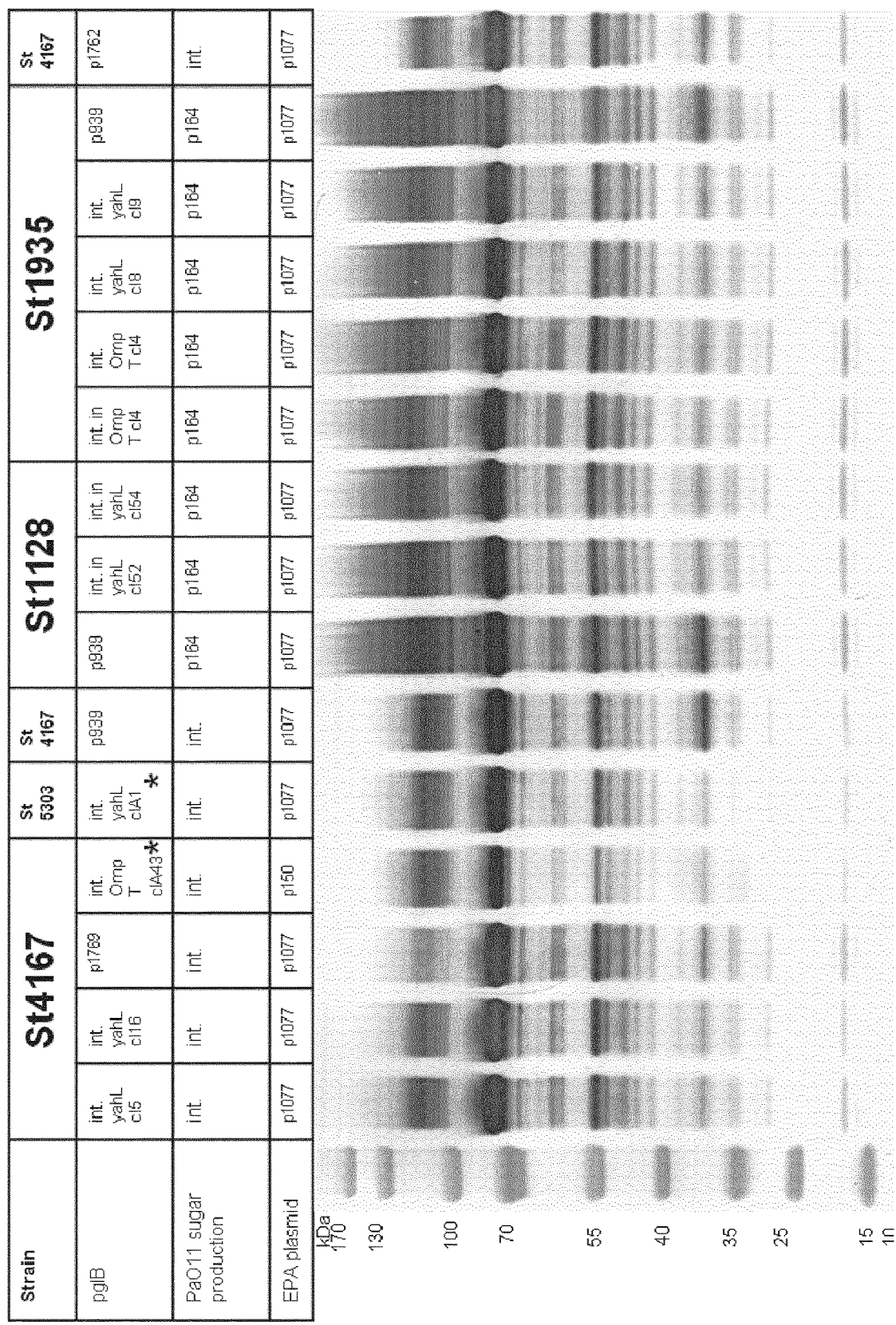
FIG. 1 Western blot of periplasmic extracts from modified host cells that produce bioconjugates. Strains as described in the Examples are indicated. "Int." refers to an integrated component. "*" refers to integration using a transposon-mediated approach.

As shown in FIG. 1, all strains expressing an oligosaccharyl transferase, carrier protein, and an rfb cluster produced bioconjugates. See the blots depicted between kDa markers 100 and 130, which correspond to EPA-O11. Importantly, this observation includes strains comprising double integration of an oligosaccharyl transferase and an rfb cluster. See, in particular, the results shown for St4167. Thus, this Example demonstrates not only that stable host cells can be generated following double insertion of genes/gene clusters into the host cell genome, but that function of the genes is maintained. Specifically, function of the inserted oligosaccharyl transferase and inserted rfb cluster was preserved, resulting in the production of bioconjugates.

Example 2: Identification of a Formyltransferase Gene that Contributes to the Synthesis of a Native *P. aeruginosa* O6 O-Antigen Oligo/Polysaccharide This example describes the identification of the *Pseudomonas aeruginosa* O6 formyltransferase.

Proteome data for the *Pseudomonas aeruginosa* O6 strain "LESB58," the genome of which is known, was searched for domains containing homology to the prototype query domains "Formyltransferase" and "FMT C-terminal domain-like" domain using the algorithm provided at www-.supfam.org/SUPERFAMILY/. The search identified 9 protein sequences with possible related domains.

To evaluate whether any of the 9 candidates identified were specific for O6 (and thereby for a formylated O antigen repreat unit) their absence in the proteome of another *Pseudomonas aeruginosa* serotype (O5, strain PAO1) was analyzed using a BLAST search (NCBI website). The *Pseudomonas aeruginosa* O5 O-antigen structure is unrelated that of *Pseudomonas aeruginosa* O6. Specifically, no formyl group is present in the O5 structure. 8 out of 9 candidates had homologues in *Pseudomonas aeruginosa* serotype O5 which indicated that these proteins were unspecific for *Pseudomonas aeruginosa* O6 strain LESB58. The remaining candidate (locus_tag=PLES_12061, GenBank: CAW25933.1; SEQ ID NO:65) had no obvious homologue in *Pseudomonas aeruginosa* serotype O5 and was therefore classified as specific for LESB58/*Pseudomonas aeruginosa* serotype O6.

To confirm O6 specificity, the presence of the discovered *Pseudomonas aeruginosa* serotype O6 formyltransferase (SEQ ID NO:65) in other *Pseudomonas aeruginosa* serotype O6 strains was verified. Proteins equivalent to the *Pseudomonas aeruginosa* serotype O6 formyltransferase (SEQ ID NO:65) were identified in four other *Pseudomonas aeruginosa* serotype O6 strains, including locus tag: PAK_01412 in strain "PAK" and locus tag: PAM18_1171 in strain M18.

Formyltransferases with low amino acid sequence identity to *Pseudomonas aeruginosa* serotype O6 formyltransferase (SEQ ID NO:65) also were identified in *Methylobacterium* sp. (33% identity, ACCESSION WP_020093860), *Thiothrix nivea* (30% identity, ACCESSION WP_002707142), *Anaerophaga thermohalophila* (28% identity, ACCESSION WP_010422313), *Halorubrum californiense* (27% identity, ACCESSION WP_008445073), *Azorhizobium caulinodans* (25% identity, ACCESSION WP_012170036) and *Burkholderia glathei* (24% identity, ACCESSION KDR39707). Taken together, these homology analyses indicated that the related genes encode an O6 specific activity related to formylation.

To test the functional activity of the *Pseudomonas aeruginosa* serotype O6 formyltransferase (SEQ ID NO:65) on the non formylated O6 repeat unit structure, the gene encoding SEQ ID NO:65 was cloned. The rare TTG START codon of the gene was replaced by ATG. A schematic representation of the cloning of the *Pseudomonas aeruginosa* serotype O6 formyltransferase (SEQ ID NO:65) into the *Pseudomonas aeruginosa* O6 rfb cluster and the relative organization of the genes is depicted in FIG. 5.

Figures 3A, 3B:
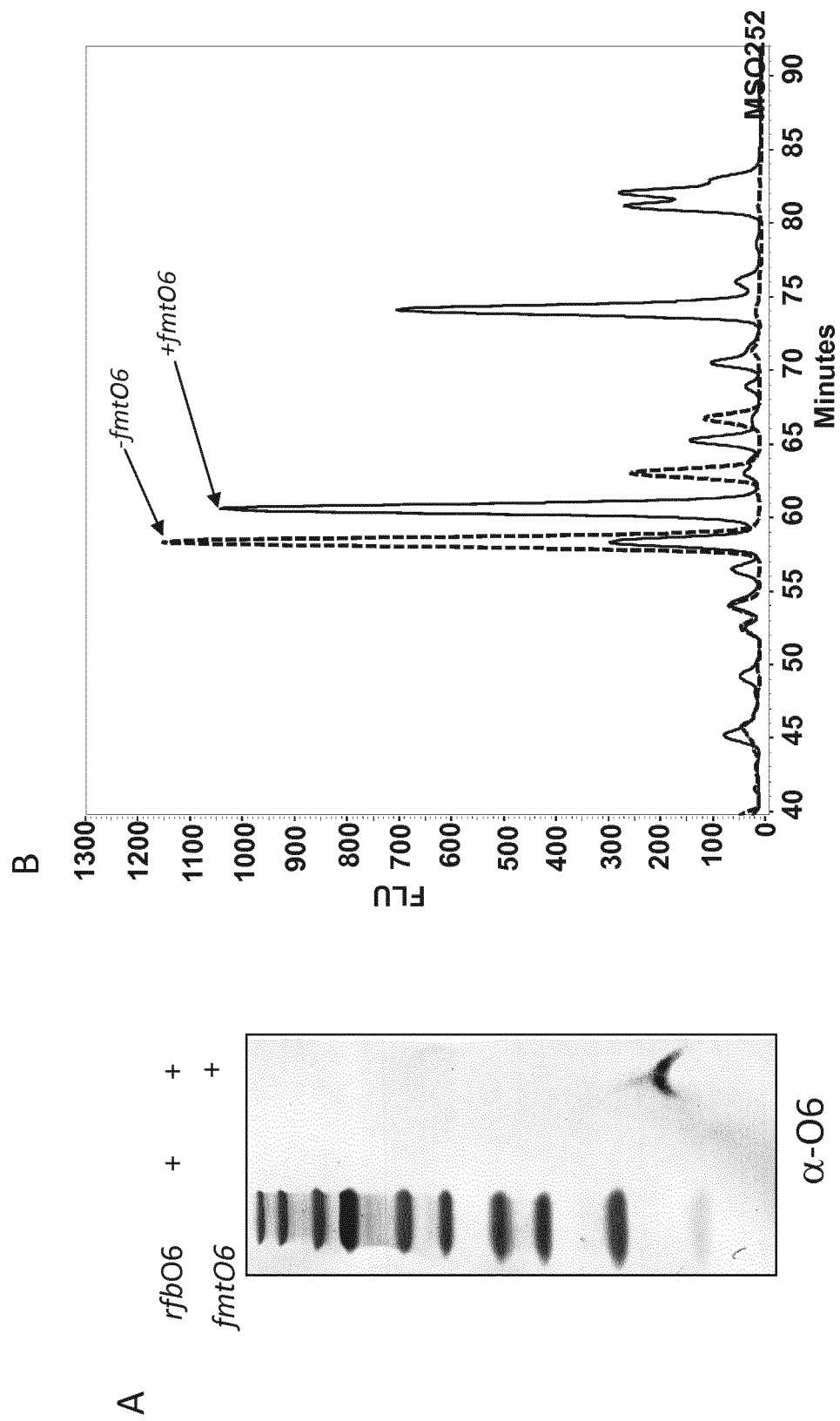
FIG. 3. Functional testing of *Pseudomonas aeruginosa* O6 formyltransferase.

Once identified, function of the *Pseudomonas aeruginosa* O6 formyltransferase was assessed. *Pseudomonas aeruginosa* serotype O6 formyltransferase (SEQ ID NO:65) was tested for functionality by co-expression with the rfb cluster genes of *Pseudomonas aeruginosa* O6 in *E. coli* strains that lack a functional ECA (wec) cluster. To show formylation, single antigen repeat units bound to lipid a core were analyzed (in a waaL positive strain). The formylated O6 O-antigen repeating unit was identified by immunodetection using an O6 specific antibody (FIG. 3A) indicating that the formyl group is a relevant epitope of the *Pseudomonas aeruginosa* O6 O antigen structure.

To show formylation on the molecular level, O6 repeat units were analyzed by MALDI MSMS. Purified and 2AB labelled repeat units showed that coexpression of *Pseudomonas aeruginosa* serotype O6 formyltransferase (SEQ ID NO:65) with the rfb cluster genes of *Pseudomonas aeruginosa* O6 gave rise to a fluorescence signal of the main peak which was shifted by 2-3 minutes (from 58 to 61', FIG. 3B).

MALDI-MSMS analysis of the material contained in the peaks at 58' resulted in a Y ion fragmentation series which is in agreement with the non formylated, N acetylated 2-AB labelled O6 repeat unit. The protonated precursor ion m/z=905, fragmented into a prominent ion series of 905→759→543→326, corresponding to losses of 146 (deoxyhexose), 216 (amidated N-acetylhexosaminuronic acid), 217 (N-acetylhexosaminuronic acid) units. Material collected at 61' obtained from cells expressing the *Pseudomonas aeruginosa* serotype O6 formyltransferase gene contained a prominent precursor ion of 891, which fragmented at 891→745→529→326, corresponding to losses of 146 (as above), 216 (as above), and 203 (amidated N-formylhexosaminuronic acid). This data proved that formylation is dependent on the expression of *Pseudomonas aeruginosa* serotype O6 formyltransferase and that accordingly the gene is encoding the formyltransferase. Thus, the gene that encodes the *Pseudomonas aeruginosa* serotype O6 formyltransferase was named fmtO6. The fact that the acetyl group of the amidated N-acetylhexosaminuronic acid is replaced by a formyl group suggests a two step mechanism wherein the acetyl group is first removed before the formyl group can be added. This model implies that a free amine group would be present at C2 as an intermediate before the formyltransferase domain attaches a formyl group to the monosaccharide. Thus, deacetylated and non formylated O antigen may be a substantial and immunologically relevant, substochiometrically present polysaccharide form of *P. aeruginosa* serotype O6.

Example 3: Identification and Testing of the Wzy Gene for Polymerization of the *P. aeruginosa* O6 O Antigen This example describes the identification of the *Pseudomonas aeruginosa* O6 wzy polymerase.

Figure 2:
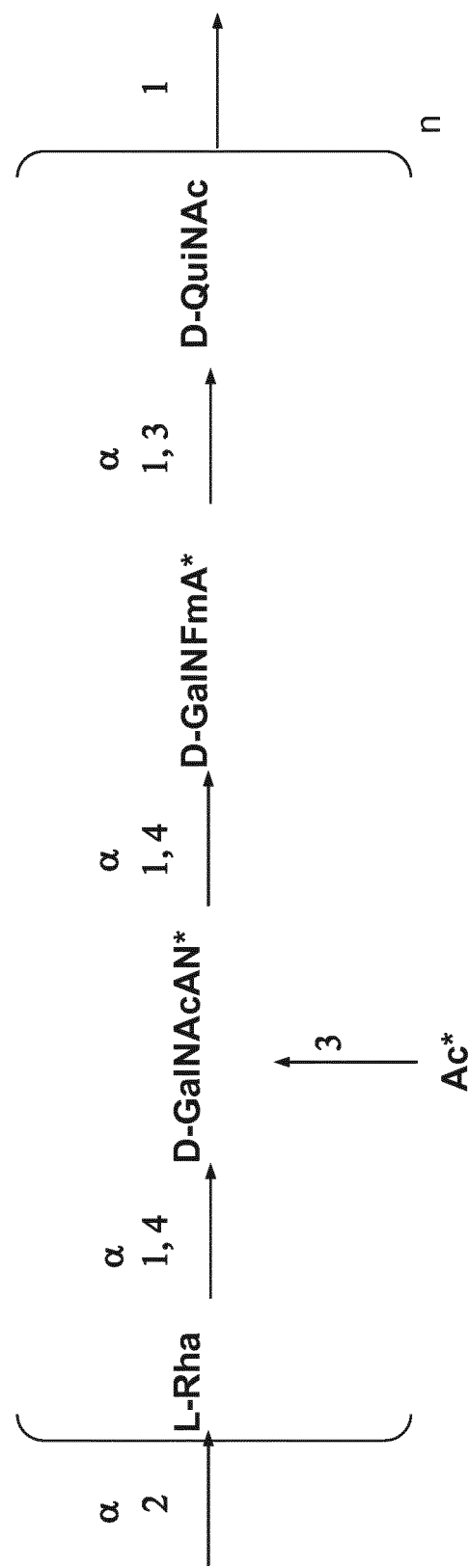
FIG. 2—Depicts the repeat unit structure of the O6 O-antigen of *Pseudomonas aeruginosa*. * indicates positions that can vary in their chemical composition according to subserotype identity. Variability is introduced by the activity of amidases that convert the acid functions of GalNAcA residues at C6 to amide, resulting in GalNAcAN (or GalNFmA to GalNFmAN; an acetyl group substitutes C3 of the GalNAcAN* residue in some subserotypes). The genes for polymerization of the repeat unit (wzy), acetylation, formylation, and amidation of one of the GalNX residues are unknown. L-Rha, L-Rhamnose; D-GalNAcAN, 6-amido-2-N-acetyl-D-galactosaminuronic acid; D-GalNFmAN, 2-N-formyl-D-galactosaminuronic; D-QuiNAc, N-acetyl-D-quinosamine.

O antigen polysaccharides constitute the outer cell surface of many Gram negative bacteria. The enzymatic machinery responsible for the biosynthesis of O antigen is often encoded in a single gene cluster called the rfb cluster. *Pseudomonas aeruginosa* serotype O6 strains express a polymeric O-antigen (FIG. 2). However, in the respective O-antigen cluster, a gene encoding an O antigen polymerase (wzy) is absent. This means that in order to recombinantly express the *P. aeruginosa* O6 O antigen in *E. coli*, identification of the wzy gene was necessary. O-antigen polymerases (wzy) are integral inner membrane proteins that catalyze the polymerization of O-antigen repeating units in the periplasmic space before "en bloc" ligation to the lipid A-core Oligosaccharide to form LPS. Wzy polymerases are highly specific for their repeat unit oligomer and homologies among wzy genes are poor.

The O-antigen of *Pseudomonas aeruginosa* O19 shares structural similarities to that of *Pseudomonas aeruginosa* O6. It was speculated that the wzy proteins that recognize both structures might also share similar properties, e.g., structure, sequence, number of transmembrane domains. The sequence of the O19 Wzy protein of *Pseudomonas aeruginosa* O19 (ACCESSION AAM27560) is known and was used as a primary query in a Blast analysis using the *Pseudomonas aeruginosa* O6 PAK strain proteome as the subject for the homology search.

To evaluate whether the candidates identified were specific for *Pseudomonas aeruginosa* O6, their presence in the proteome of another *Pseudomonas aeruginosa* serotype (O5, strain PAO1) was analyzed. The O5 O-antigen structure is unrelated to that of O6 and O19. The Top 100 results were analyzed individually for the presence in the *Pseudomonas aeruginosa* O5 proteome using blast analysis. 97 out of 100 candidates from the PAK proteome had homologues in the *Pseudomonas aeruginosa* serotype O5 proteome which indicated that these proteins were generally present in *Pseudomonas aeruginosa* strains and possibly unrelated to O6 O antigen biosynthesis. Three out of the 100 candidates had no obvious homologue in the *Pseudomonas aeruginosa* O5 proteome, and were therefore determined to be *Pseudomonas aeruginosa* O6 specific.

To test whether one of the three identified candidate proteins was a *Pseudomonas aeruginosa* O6 wzy, the three proteins were used as query in a Blast analysis. One of the three candidates, PAK_01823 (O6wzy PAK_01823; SEQ ID NO:66), shared amino acid sequence identity to other, known oligosaccharide repeat unit polymerases, e.g, 25% identity to *Streptococcus sanguinis* oligosaccharide repeat unit polymerases (ACCESSION WP_004192559) and 22% identity to *Escherichia coli* O139 oligosaccharide repeat unit polymerases (ACCESSION AAZ85718). Thus, PAK_01823 (O6wzy PAK_01823; SEQ ID NO:66) was identified as the *Pseudomonas aeruginosa* O6 wzy.

To further confirm SEQ ID NO:66 as the protein encoded by the *Pseudomonas aeruginosa* O6 wzy, the subcellular localization of the protein was predicted bioinformatically using PSORTb (www.psort.org/psortb/). The protein was predicted to be localized in the cytoplasmic membrane with 11 transmembrane domains, a feature that is common among O-antigen polymerases.

Proteins equivalent to PAK_01823 (O6wzy PAK_01823; SEQ ID NO:66) were found in other O6 positive *P. aeruginosa* strains, including the LESB58 strain (which had a *Pseudomonas aeruginosa* O6 wzy protein with only 1 aa difference compared to the PAK strain and a strain tested internally).

Next, functional testing of the *Pseudomonas aeruginosa* O6 wzy was carried out. The *Pseudomonas aeruginosa* O6 rfb cluster, the fmtO6 gene (i.e., the gene encoding SEQ ID NO:2, discussed in Example 2, above), and the gene encoding Pseudomonas aeruginosa O6 wzy (i.e., the gene encoding SEQ ID NO:66) were co-expressed in E. coli W3110 Δwec cells, and the lipopolysaccharide formed was analyzed by immunoblotting (FIG. 4). Anti-O6 antiserum detected a ladder like signal only in the sample originating from the cells that contained all three transgenes, indicating that PAK_01823 (O6wzy PAK_01823; SEQ ID NO:66) is indeed the polymerase of P. aeruginosa O6. Thus, the gene encoding PAK_01823 was named O6wzy.

To generate a single gene cluster containing all genetic elements required to enable E. coli to recombinantly express the P. aeruginosa O6 O antigen, the fmtO6 and O6wzy genes (i.e., the genes encoding SEQ ID NOs: 65 and 66, respectively) were cloned downstream of the P. aeruginosa O6 rfb cluster. A schematic representation of the cloning of the codon usage optimized Pseudomonas aeruginosa O6 O-antigen polymerase O6wzy into the cloned Pseudomonas aeruginosa O6 rfb cluster along with the O6 formyltransferase and the relative organization of the genes is depicted in FIG. 5. It further was determined that the fmtO6 and O6wzy genes (i.e., the genes encoding SEQ ID NOs: 65 and 66, respectively) could be inserted into the P. aeruginosa O6 rfb cluster at multiple positions. Specifically, the fmtO6 gene could be inserted in a clockwise orientation relative to the rfb cluster downstream of the rfb cluster or upstream of the rfb cluster under the control of a separate promotor. In addition, the fmtO6 gene could be inserted in a counterclockwise orientation relative to the rfb cluster upstream or downstream of the rfb cluster. The O6wzy gene could be inserted in a clockwise orientation relative to the rfb cluster upstream or downstream of the rfb cluster or upstream of the rfb cluster under the control of a separate promotor. All constructs described above were active in terms of P. aeruginosa O6 O antigen biosynthesis (data not shown).

Example 4: Bacterial Strains with an Inserted Oligosaccharyl Transferase and an Inserted Rfb, Completed rfbO6 Cluster are Stable and Produce Bioconjugates Example 1 demonstrates that bioconjugates can successfully be produced by a bacterial host strain that has been genetically modified by insertion of (i) a nucleic acid encoding an oligosaccharyl transferase and (ii) a nucleic acid encoding an rfb cluster. In this Example, experiments similar to those described in Example 1 were performed, using the Pseudomonas protein PcrV as a carrier protein.

Naturally, the primary amino acid sequence of PcrV (see, e.g., UniProt O30527) does not comprise an N-glycosylation consensus sequence ("glycosite"). Using the methods described in WO 2006/119987, recombinant variants of PcrV comprising one, two, three, four, or five glycosites were engineered. In particular, by manipulation of the nucleic acid sequence encoduing PcrV, PcrV variants were created that expressed one, two, three, four, or five of the optimized N-glycosylation consensuss sequence Asp(Glu)-X-Asn-Z-Ser(Thr), wherein X and Z are independently selected from any natural amino acid except Pro.

Modified E. coli host cells were generated by inserting the following directly into the host cell genome: (i) a nucleic acid encoding the C. jejuni oligosaccharyl transferase (PglB) and (ii) a nucleic acid encoding the rfb cluster from the Pseudomonas aeruginosa serotype O6 PAK strain. This rfb cluster encodes genes necessary for O-antigen synthesis of the Pseudomonas aeruginosa serogroup O6 antigen. The insertions were performed using the novel insertion method described in PCT/EP2013/071328 (see Section 5.2, above) or the pUT mini system (Biomedal Lifescience). The E. coli host cells further were modified by introduction of a plasmid that expresses PcrV comprising one to five glycosites, as described above. Thus, the modified E. coli host cells described in this example express (i) the C. jejuni oligosaccharyl transferase (PglB), by virtue of integration of a nucleic acid encoding the oligosaccharyl transferase into the host cell genome; (ii) genes of a Pseudomonas aeruginosa rfb cluster that produce the O6 antigen, by virtue of integration of a nucleic acid encoding the rfb cluster from Pseudomonas aeruginosa PAK strain into the host cell genome; and (iii) the modified PcrV carrier protein, by virtue of transforming the host cell with a plasmid comprising a modified nucleic acid encoding the carrier protein (where the nucleic acid has been modified so that it encodes one to five glycosites, as described above).

Additional modified E. coli host cells were generated to allow for comparison of the ability of the modified host cells comprising double integrations (integration of an oligosaccharyl transferase and integration of an rfb cluster) to produce bioconjugates (PcrV-O6) with bioconjugate production by host cells having (i) only a single integration of the oligosaccharyl transferase or the rfb cluster and the remaining components (carrier protein and oligosaccharyl transferase or rfb cluster) plasmid expressed by the host cell; or (ii) no integrated components, with all components (carrier protein and oligosaccharyl transferase and rfb cluster) plasmid expressed.

Three different E. coli strains were used and compared in the analysis: (i) "St7343," which comprises both pglB and the completed O6 rfb cluster inserted into the host cell genome (i.e., is a double integrated strain), and a plasmid encoding a PcrV carrier protein (with one, two, three, four, or five glycosites); (ii) "St7209," which comprises plasmid-expressed pglB, the O6 rfb cluster inserted into the host cell genome, and a plasmid encoding a PcrV carrier protein (with one, two, three, four, or five glycosites); and (iii) "St2182," which comprises plasmid-expressed pglB, plasmid-expressed O6 rfb cluster, and a plasmid encoding a PcrV carrier protein (with one, two, three, four, or five glycosites). FIG. 6 depicts the characteristics of each strain (6A: St7343; 6B: St7209; 6C: St2182).

As shown in FIG. 6, all strains expressing an oligosaccharyl transferase, carrier protein, and an rfb cluster produced bioconjugates. See the blots depicted between kDa markers 40-70 (around the kDa 55 marker), which correspond to PcrV-O6. Importantly, as shown in Example 1, this observation includes strains comprising double integration of an oligosaccharyl transferase and an rfb cluster. See, in particular, the results shown in FIG. 6A. Thus, like Example 1, this Example demonstrates not only that stable host cells can be generated following double insertion of genes/gene clusters into the host cell genome, but that function of the genes is maintained. Specifically, function of the inserted oligosaccharyl transferase and inserted rfb cluster was preserved, resulting in the production of bioconjugates.

Example 5: Production and Purification of EPA-O6 Bioconjugates

This example describes the production of bioconjugates comprising the Pseudomonas aeruginosa O6 antigen.

E. coli W3110 ΔwaaL Δwec Δrfb was transformed with plasmids comprising the Pseudomonas aeruginosa O6 rfb cluster, the oligosaccharyl transferase pglB from C. jejuni, the gene encoding the detoxified carrier protein EPA, and the QuiNAc biosynthesis/transferase genes wbpVLM (from a *Pseudomonas aeruginosa* O6 strain). Results of plasmid retention analysis are depicted in FIG. 8. Medium (LB broth) supplemented with Tetracyclin, Spectinomycin, Kanamycin and Ampicillin was inoculated with host cells containing all four plasmids. The pre-culture was grown overnight at 37° C.

The next day, medium (TB) supplemented with $MgCl_2$, Tetracyclin, Spectinomycin, Kanamycin and Ampicillin was inoculated by diluting the preculture to $OD_{600}$ 0.1. Cells were grown at 37° C. until approximately $OD_{600}$ 0.8-1.0 was reached, then expression of pglb, epa and wbpVLM was induced by the addition of 1 mM IPTG and 0.1% arabinose. Cells were harvested by centrifugation after over night induction.

EPA-O6 bioconjugates were purified from periplasmic extracts of modified host cells using Metal-chelate affinity chromatography (IMAC), anion exchange chromatography (Source Q) and size exclusion chromatography (SEC). Elution fractions containing glycoconjugates were pooled and subsequently submitted to the next chromatography step. The final SEC eluates were characterized by SDS-PAGE followed by Coomassie Blue staining or Western blot using the antibodies indicated in FIG. 7.

The EPA-O6 bioconjugate was characterized using an array of analytical methods. The level of endotoxin was measured using the LAL assay (13 EU/ml). Purity was determined by SDS-PAGE and capillary gel electrophoresis (CGE, 86% purity). The amount of protein was measured using the BCA assay (1.75 mg/ml). The amount of polysaccharide was measured using the Anthrone assay (Dubois et al., 1956; 311.6 ug/ml). The average size of the O6-Polymer was determined using a high resolution "degree-of-glycosylation" (DOG) SDS-PAGE (average of 7.9 repeating units per polymer). Determination of electric isoforms of the bioconjugate was done by isoelectric focusing (IEF). Finally, the identity of the bioconjugate was confirmed by Immunoblotting using antibodies directed against the protein (EPA) or the polysaccharide (O6).

Example 6: Immunization Studies

This Example demonstrates that the *P. aeruginosa* O6-EPA bioconjugate is immunogenic.

Female, 6 week old BALB/c OlaHsd mice (in groups of 20) were immunized intramuscularly at days 0, 14 and 28 with 0.2 µg or 2 µg of O6-EPA conjugate (see Example 5) in a non adjuvanated or adjuvanated formulation (with an oil-in-water emulsion adjuvant). A control group of 10 mice was vaccinated with ajuvant (O/W) alone. Anti-O6 ELISA were determined in individual sera collected at day 42 (14 post III) and opsonic titres were determined on pooled Post-II and Post-Ill sera. Results are shown in FIG. 9 and described in detail below.

FIG. 9A depicts the anti-O6 ELISA response. Purified O6 LPS-O6 (PaO6a,6c) was coated at 8 µg/ml in phosphate buffered saline (PBS) on high-binding microtitre plates (Nunc Maxisorp), overnight at 4° C. The plates were blocked with PBS-BSA 1% for 30 min at RT with agitation. The mouse antisera were prediluted 1/100 or 1/10 and then, further two fold dilutions were made in microplates and incubated at room temperature for 30 minutes with agitation. After washing, bound murine antibody was detected using Jackson ImmunoLaboratories Inc. peroxidase-conjugated AffiniPure Goat Anti-Mouse IgG (H+L) (ref: 115-035-003) diluted 1/5000 in PBS-tween 0.05%-BSA 0.2%. The detection antibodies were incubated for 30 minutes at room temperature with agitation. The color was developed using 4 mg OPD+5 µl H2O2 per 10 ml pH 4.5 0.1M citrate buffer for 15 minutes in the dark at room temperature. The reaction was stopped with 50 µl HCl, and the optical density (OD) was read at 490 nm relative to 620 nm.

The level of anti-O6 antibodies present in the sera was expressed in mid-point titers. A GMT of individual sera was calculated for the 20 samples in each treatment group (10 for the control group).

An immune response was observed in mice after injection of the bioconjugate formulated with the adjuvant. No difference was observed between doses. Similar observations were made regarding the percentage of seroconversion. No or very weak responses were observed with the non adjuvanted formulation.

FIG. 9B shows opsonic titer in HL60 cells from mice immunized with O6-EPA bioconjugate formulated with adjuvant or not.

The opsonophagocytosis assay (OPA) was performed in round-bottom microplates with 15 µl of HL-60 phagocytic cells (adjusted to 5 10e6 cells/ml), 15 µl of *P. aeruginosa* bacteria (grown on TSA agar plate), 15 µl of the test serum dilutions, and 15 µl of piglet complement. The inactivated test pooled sera were first diluted (1/16 or 1/50 final dilution) in HBSS-BSA 1% and added to a *P. aeruginosa* O6 strain (strain ID: HNCMB 170009, obtained from Hungarian National Collection of Medical Bacteria) diluted in order to count 200-250 CFU/well at the end of the test.

The HL-60 cells (adjusted to 5.10e6/ml) and the piglet complement (12.5% final) were then added in each well. A control with inactivated complement was included for each test sample.

The reaction mixture was incubated at 37° C. for 90 minutes with agitation. After a 1/200 dilution, 50 µl of the volume was then transferred into a flat-bottom microplate. 50 µl of MH agar followed by PBS-0.9% agar was added. Automated colony counts were performed after an overnight incubation at 30° C.

The opsonophagocytic activity is expressed as the reciprocal of the serum dilution giving at least 50% killing.

The data demonstrate the functionality of the antibodies induced after injection with the adjuvanted group.

In conclusion, this example demonstrates that the *P. aeruginosa* O6-EPA bioconjugate is both immunogenic and functional (i.e. induces antibodies that kill *P. aeruginosa* O6 in vivo).

Example 7

This example demonstrates that the *P. aeruginosa* O6-PcrV bioconjugates are immunogenic.

Immunization

Groups of 20 Balb/c 6 week old mice and groups of 20 female 6 weeks old OFA SD rats were immunized IM at days 0, 14 and 28 with 0.2 µg of O6-PcrV bioconjugate in a non-adjuvanted or oil in water emulsion adjuvanted formulation.

The IgG immune response was determined by ELISA (with an anti-O6 and anti-PcrV ELISA). The functionality of antibodies were evaluated in an opsonophagocytosis assay for O6 and in a hemolysis assay for PcrV. The immune response was evaluated in individual sera collected at day 42 (post III) and on pooled Post-II and post-III sera.

Conjugates Tested

Three *P. aeruginosa* O6-PcrV conjugates were tested. In each case, three glycosylation sites had been engineered into PcrV and the short, medium or long O6 chains were added to the glycosylation sites.

| Con-jugate | No. of en-gineered glyco-sylation sites | O6 polymer length | Protein concen-tration Mg/ml | Sugar concen-tration Mg/ml | s/p ratio | endo-toxin | purity |
|---|---|---|---|---|---|---|---|
| O6-PcrV short | 3 | short | 0.849 | 0.169 | 19.9% | <5 | 97.2% |
| O6-PcrV Medium | 3 | medium | 0.154 | 0.072 | 46.8% | 9.425 | 97.7% |
| O6-PcrV long | 3 | long | 0.531 | 0.450 | 84.7% | <5 | 100% |

Anti-O6 ELISA (on Rat Sera)

Purified O6-LPS was coated at 8 μg/ml in phosphate buffered saline (PBS) on high-binding microtitre plates (Nunc Maxisorp), overnight at 4° C. The plates were blocked with PBS-BSA 1% for 30 minutes at RT with agitation. The rat antisera were prediluted 1/100 or 1/10 and then, further twofold dilutions were made in microplates and incubated at RT for 30 minutes with agitation. After washing, bound rat antibodies were detected using Jackson ImmunoLaboratories Inc. peroxidase-conjugated AffiniPure Goat Anti-rat IgG (H+L) (ref: 112-035-003) diluted 1/2500 in PBS-tween 0.05%. The detection antibodies were incubated for 30 minutes at room temperature with agitation. The color was developed using 4 mg OPD+5 μl H2O2 per 10 ml pH 4.5 0.1M citrate buffer for 15 minutes in the dark at room temperature. The reaction was stopped with 50 μl HCl, and the optical density (OD) was read at 490 nm relative to 620 nm. The level of anti-O6 antibodies present in the sera was expressed in mid-point titers. A GMT was calculated for the 20 individual samples in each treatment group.

Anti-PcrV ELISA (on Rat Sera)

Purified PcrV His-tagged was coated at 1 μg/ml in phosphate buffered saline (PBS) on high-binding microtitre plates (Nunc Maxisorp), overnight at 4° C. The plates were blocked with PBS-BSA 1% for 30 minutes at RT with agitation. The rat antisera were prediluted 1/400 and then, further twofold dilutions were made in microplates and incubated at RT for 30 minutes with agitation. After washing, bound rat antibodies were detected using Jackson ImmunoLaboratories Inc. peroxidase-conjugated AffiniPure Goat Anti-rat IgG (H+L) (ref: 112-035-003) diluted 1/5000 in PBS-tween 0.05%. The detection antibodies were incubated for 30 minutes at room temperature with agitation. The color was developed using 4 mg OPD+5 μl H2O2 per 10 ml pH 4.5 0.1M citrate buffer for 15 minutes in the dark at room temperature. The reaction was stopped with 50 μl HCl, and the optical density (OD) was read at 490 nm relative to 620 nm.

The level of anti-PcrV antibodies present in the sera was expressed in mid-point titers. A GMT was calculated for the 20 samples in each treatment group.

Anti-O6 ELISA (on Mouse Sera)

Purified O6-LPS was coated at 8 μg/ml in phosphate buffered saline (PBS) on high-binding microtitre plates (Nunc Maxisorp), overnight at 4° C. The plates were blocked with PBS-BSA 1% for 30 minutes at RT with agitation. The mouse antisera were prediluted 1/100 or 1/10 and then, further twofold dilutions were made in microplates and incubated at RT for 30 minutes with agitation. After washing, bound mouse antibodies were detected using Jackson ImmunoLaboratories Inc. peroxidase-conjugated AffiniPure Goat Anti-mouse IgG (H+L) (ref: 115-035-003) diluted 1/2500 in PBS-tween 0.05%. The detection antibodies were incubated for 30 minutes at room temperature with agitation. The color was developed using 4 mg OPD+5 μl H2O2 per 10 ml pH 4.5 0.1M citrate buffer for 15 minutes in the dark at room temperature. The reaction was stopped with 50 μl HCl, and the optical density (OD) was read at 490 nm relative to 620 nm. The level of anti-O6 antibodies present in the sera was expressed in mid-point titers. A GMT was calculated for the 20 individual samples in each treatment group.

Anti-PcrV ELISA (on Mouse Sera)

Purified PcrV His-tagged was coated at 1 μg/ml in phosphate buffered saline (PBS) on high-binding microtitre plates (Nunc Maxisorp), overnight at 4° C. The plates were blocked with PBS-BSA 1% for 30 minutes at RT with agitation. The mouse antisera were prediluted 1/400 and then, further twofold dilutions were made in microplates and incubated at RT for 30 minutes with agitation. After washing, bound mouse antibodies were detected using Jackson ImmunoLaboratories Inc. peroxidase-conjugated AffiniPure Goat Anti-mouse IgG (H+L) (ref: 115-035-003) diluted 1/5000 in PBS-tween 0.05%. The detection antibodies were incubated for 30 minutes at room temperature with agitation. The color was developed using 4 mg OPD+5 μl H2O2 per 10 ml pH 4.5 0.1M citrate buffer for 15 minutes in the dark at room temperature. The reaction was stopped with 50 μl HCl, and the optical density (OD) was read at 490 nm relative to 620 nm.

The level of anti-PcrV antibodies present in the sera was expressed in mid-point titers. A GMT was calculated for the 20 samples in each treatment group.

Anti-O6 OPA Response

The osponophagocytosis assay (OPA) was performed in round-bottom microplates with 15 μl of HL-60 phagocytic cells (adjusted to 5 $10e^6$ cells/ml), 15 μl of *P. aeruginosa* bacteria (grown on TSA agar plate), 15 μl of the test serum dilutions and 15 μl of piglet complement. The inactivated test sera were first diluted (1/4) in HBSS-BSA 1% and added to *P. aeruginosa* strain (GVXN 5871 diluted in order to obtain 200-250 CFU/well at the end of the test).

The HL-60 cells (adjusted to 5.10e6/ml) and the piglet complement (12.5% final) were then added in each well. A control with inactivated complement was also included for each test sample.

The reaction mixture was incubated at 37° C. for 90 minutes with agitation. After a 1/200 dilution, 50 μl of the volume was then transferred into a flat-bottom microplate. 50 μl of MH agar followed by PBS-0.9% agar was added (and additional 50 μl for safety reason). Automated colony counts were performed after an overnight incubation at 30° C.

The opsonophagocytic activity was expressed as the reciprocal of the serum dilution giving at least 50% killing.

Anti-PcrV Haemolysis Inhibition Response

ATCC 29260 (PCRV+) was cultured over night at 37° C. with 5% CO2, on TSA Agar plate and harvested with 5 ml of MinS liquid media. A few μl were seeded in Wyame Fiole and grown during 4 hours.

Serial twofold dilutions of test sera were performed in 80 µl phosphate buffer saline (DPBS) in 96-well U-bottom microplates.

80 µl of 3× diluted ATCC 29260 were then added (dilution which lyses 100% of rabbit erythrocytes). 80 µl of purified and diluted rabbit erythrocytes were then added to each well. The dilution of the rabbit erythrocytes was determined for each assay in order to obtain an identical haemolysis and a standardized haemolysis inhibition. The plates were centrifugated at 1000 rpm, at 4° C. for 10 min and incubated at 37 C for 2 hours. The plates were then centrifuged at 1000 rpm for 10 minutes at 4° C. 150 µl (Supernatant) of each well were transferred to a flat bottom plate and read at 405 nm with a microtitre plate reader.

The haemolysis inhibition activity was expressed by mid-point titers (50% inhibition) of pooled sera.

Anti-O6 IgG ELISA 5 pools of 4 rats post II and individual sera post III were evaluated by ELISA on all the groups of the experiment. Results are shown on FIG. 14.

A boost effect is observed from Post II to post III pooled sera. The non-adjuvanted O6 bioconjugate has low immunogenicity in comparison with all the O6 bioconjugates formulated in an oil in water emulsion adjuvant, which are more immunogenic.

Anti-PcrV Immune Response 5 pools of 4 rats post II and individual sera post III were evaluated by ELISA on all the PcrV groups of the experiment (G5 to G9).

The geometric mean of mid-point titers obtained for both the Post II and Post III rat sera are presented in FIG. 13.

A boost effect was observed between Post II and post III pooled sera. No or a very weak immune response anti-PcrV was observed with O6-PcrV non-adjuvanted. By contrast, a good immune response was observed against PcrV protein carrier for the three O6 bio conjugates formulated in an oil in water adjuvant.

The highest antibody response was observed with the Group 5 O6-PcrV bioconjugate including 20% sugar/protein ratio (the higher protein concentration).

PcrV Haemolysis Inhibition Assay:

Results of the PcrV haemolysis inhibition assays are shown in FIG. 10. In mice immunised with the O6-PcrV conjugates, good PcrV haemolysis inhibition titres were achieved for all of the conjugates tested. PcrV was able to generate functional antibodies with good PcrV haemolysis inhibition titres for all O6-PcrV bioconjugates tested in mice. While shorter saccharide chains having a saccharide/protein ratio of 20% showed a trend towards better titres than the other conjugates, the improvement was not statistically significant.

In both mice and rats, the presence of an oil in water emulsion enhanced the immune response against PcrV.

Opsonophagocytosis Results

Results of the opsonophagocytosis assays are shown in FIG. 12. A good opsonophagocytosis response was achieved in samples where the conjugate formulation contained an oil in water adjuvant. This was not tested in unadjuvanted samples. Subsequent studies have shown very weak opsonic responses in the sera from mice immunised with non-adjuvanted conjugates.

The present disclosure is not to be limited in scope by the specific embodiments described herein. Indeed, various modifications of the subject matter provided herein, in addition to those described, will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. A conjugate comprising or consisting of an antigen covalently linked to a *Pseudomonas aeruginosa* PcrV carrier protein comprising an amino acid sequence which is at least 90% identical to the sequence of SEQ ID NO: 4, wherein the antigen is linked (either directly or through a linker) to an asparagine amino acid residue of the *P. aeruginosa* PcrV carrier protein wherein the asparagine residue is part of a D/E-X-N-X-S/T consensus sequence introduced into the amino acid sequence which is at least 90% identical to the sequence of SEQ ID NO: 4, wherein X is any amino acid apart from proline, wherein the asparagine residue is situated at a position equivalent to between amino acids 1-50 of SEQ ID NO:4; wherein the PerV carrier protein elicits a neutralizing immune response against PcrV: wherein a peptide comprising the D/E-X-N-X-S/T consensus sequence is introduced into the amino acid sequence by the removal of a PcrV peptide sequence and its replacement with the peptide comprising the D/E-X-N-X-S/T consensus sequence, wherein the PcrV peptide sequence contains 1-7 amino acids, wherein the PcrV peptide sequences contains one amino acid.

2. The conjugate of claim 1, wherein the peptide comprising the D/E-X-N-X-S/T consensus sequence is introduced into the amino acid sequence at a position between amino acid residue 1-120 of SEQ ID:4, preferably wherein the peptide comprising the D/E-X-N-X-S/T consensus sequence is introduced into the amino acid sequence at a position between amino acid residue 1-24 of SEQ ID:4.

3. The conjugate of claim 1, wherein the antigen is a saccharide, preferably wherein the antigen is a bacterial capsular saccharide or a bacterial lipopolysaccharides or lipooligosaccharide, preferably a lipopolysaccharides from *P. aeruginosa*, and preferably wherein the antigen is a O-antigen from *P. aeruginosa*, optionally O1, O2, O3, O4, O5, O6, O7, O8, O9, O10, O11, O12, O13, O14, O15, O16, O17, O18, O19 or O20.

4. An immunogenic composition comprising the conjugate of claim 1 and a pharmaceutically acceptable excipient.

5. The immunogenic composition of claim 4, further comprising additional antigens.

6. The immunogenic composition of claim 5, wherein the additional antigens are selected from the group consisting of a conjugate of and O-antigen and a carrier protein, a conjugate of a bacterial capsular polysaccharide and a carrier protein, a conjugate of a lipooligosaccharide and a carrier protein and a protein.

\* \* \* \* \*

SEQUENCE LISTING

```
<160> NUMBER OF SEQ ID NOS: 68

<210> SEQ ID NO 1
<211> LENGTH: 294
<212> TYPE: PRT
<213> ORGANISM: Pseudomonas aeruginosa

<400> SEQUENCE: 1

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
            85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125
```

```
Lys Ala Leu Leu Asp Glu Leu Lys Ala Leu Thr Ala Glu Leu Lys Val
    130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile
        290

<210> SEQ ID NO 2
<211> LENGTH: 312
<212> TYPE: PRT
<213> ORGANISM: Pseudomonas aeruginosa

<400> SEQUENCE: 2

Ala Lys Asp Gln Asn Ala Thr Lys Val Arg Asn Leu Asn Ala Ala Arg
1               5                   10                  15

Glu Leu Phe Lys Asp Gln Asn Ala Thr Lys Asp Glu Leu Leu Ala Ala
            20                  25                  30

Ser Lys Asp Gln Asn Ala Thr Lys Ala Pro Ala Ser Ala Glu Gln Glu
        35                  40                  45

Glu Leu Leu Ala Leu Leu Arg Ser Glu Arg Ile Val Leu Ala His Ala
50                  55                  60

Gly Gln Pro Leu Ser Glu Ala Gln Val Leu Lys Ala Leu Ala Trp Leu
65                  70                  75                  80

Leu Ala Ala Asn Pro Ser Ala Pro Pro Gly Gln Gly Leu Glu Val Leu
                85                  90                  95

Arg Glu Val Leu Gln Ala Arg Arg Gln Pro Gly Ala Gln Trp Asp Leu
            100                 105                 110

Arg Glu Phe Leu Val Ser Ala Tyr Phe Ser Leu His Gly Arg Leu Asp
        115                 120                 125

Glu Asp Val Ile Gly Val Tyr Lys Asp Val Leu Gln Thr Gln Asp Gly
    130                 135                 140

Lys Arg Lys Ala Leu Leu Asp Glu Leu Lys Ala Leu Thr Ala Glu Leu
145                 150                 155                 160

Lys Val Tyr Ser Val Ile Gln Ser Gln Ile Asn Ala Ala Leu Ser Ala
                165                 170                 175

Lys Gln Gly Ile Arg Ile Asp Ala Gly Gly Ile Asp Leu Val Asp Pro
            180                 185                 190

Thr Leu Tyr Gly Tyr Ala Val Gly Asp Pro Arg Trp Lys Asp Ser Pro
        195                 200                 205
```

```
Glu Tyr Ala Leu Leu Ser Asn Leu Asp Thr Phe Ser Gly Lys Leu Ser
            210                 215                 220
Ile Lys Asp Phe Leu Ser Gly Ser Pro Lys Gln Ser Gly Glu Leu Lys
225                 230                 235                 240
Gly Leu Ser Asp Glu Tyr Pro Phe Glu Lys Asp Asn Asn Pro Val Gly
                245                 250                 255
Asn Phe Ala Thr Thr Val Ser Asp Arg Ser Arg Pro Leu Asn Asp Lys
                260                 265                 270
Val Asn Glu Lys Thr Thr Leu Leu Asn Asp Thr Ser Ser Arg Tyr Asn
            275                 280                 285
Ser Ala Val Glu Ala Leu Asn Arg Phe Ile Gln Lys Tyr Asp Ser Val
            290                 295                 300
Leu Arg Asp Ile Leu Ser Ala Ile
305                 310

<210> SEQ ID NO 3
<211> LENGTH: 317
<212> TYPE: PRT
<213> ORGANISM: Pseudomonas aeruginosa

<400> SEQUENCE: 3

Met Ser Phe Lys Lys Ile Ile Lys Ala Phe Val Ile Met Ala Ala Leu
1               5                   10                  15
Val Ser Val Gln Ala His Ala Ala Glu Val Arg Asn Leu Asn Ala Ala
            20                  25                  30
Arg Glu Leu Phe Leu Asp Glu Leu Leu Ala Ala Ser Ala Ala Pro Ala
        35                  40                  45
Ser Ala Glu Gln Glu Glu Leu Leu Ala Leu Leu Arg Ser Glu Arg Ile
50                  55                  60
Val Leu Ala His Ala Gly Gln Pro Leu Ser Glu Ala Gln Val Leu Lys
65                  70                  75                  80
Ala Leu Ala Trp Leu Leu Ala Ala Asn Pro Ser Ala Pro Pro Gly Gln
                85                  90                  95
Gly Leu Glu Val Leu Arg Glu Val Leu Gln Ala Arg Arg Gln Pro Gly
            100                 105                 110
Ala Gln Trp Asp Leu Arg Glu Phe Leu Val Ser Ala Tyr Phe Ser Leu
        115                 120                 125
His Gly Arg Leu Asp Glu Asp Val Ile Gly Val Tyr Lys Asp Val Leu
130                 135                 140
Gln Thr Gln Asp Gly Lys Arg Lys Ala Leu Leu Asp Glu Leu Lys Ala
145                 150                 155                 160
Leu Thr Ala Glu Leu Lys Val Tyr Ser Val Ile Gln Ser Gln Ile Asn
                165                 170                 175
Ala Ala Leu Ser Ala Lys Gln Gly Ile Arg Ile Asp Ala Gly Gly Ile
            180                 185                 190
Asp Leu Val Asp Pro Thr Leu Tyr Gly Tyr Ala Val Gly Asp Pro Arg
        195                 200                 205
Trp Lys Asp Ser Pro Glu Tyr Ala Leu Leu Ser Asn Leu Asp Thr Phe
210                 215                 220
Ser Gly Lys Leu Ser Ile Lys Asp Phe Leu Ser Gly Ser Pro Lys Gln
225                 230                 235                 240
Ser Gly Glu Leu Lys Gly Leu Ser Asp Glu Tyr Pro Phe Glu Lys Asp
                245                 250                 255
Asn Asn Pro Val Gly Asn Phe Ala Thr Thr Val Ser Asp Arg Ser Arg
            260                 265                 270
```

```
Pro Leu Asn Asp Lys Val Asn Glu Lys Thr Thr Leu Leu Asn Asp Thr
            275                 280                 285

Ser Ser Arg Tyr Asn Ser Ala Val Glu Ala Leu Asn Arg Phe Ile Gln
    290                 295                 300

Lys Tyr Asp Ser Val Leu Arg Asp Ile Leu Ser Ala Ile
305                 310                 315
```

<210> SEQ ID NO 4
<211> LENGTH: 294
<212> TYPE: PRT
<213> ORGANISM: Pseudomonas aeruginosa

<400> SEQUENCE: 4

```
Ala Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
50                  55                  60

Ala Asn Pro Ser Ala Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile
    290
```

<210> SEQ ID NO 5
<211> LENGTH: 114
<212> TYPE: PRT
<213> ORGANISM: Pseudomonas aeruginosa -continued

<400> SEQUENCE: 5

Val Tyr Ser Val Ile Gln Ser Gln Ile Asn Ala Ala Leu Ser Ala Lys
1               5                   10                  15

Gln Gly Ile Arg Ile Asp Ala Gly Gly Ile Asp Leu Val Asp Pro Thr
            20                  25                  30

Leu Tyr Gly Tyr Ala Val Gly Asp Pro Arg Trp Lys Asp Ser Pro Glu
        35                  40                  45

Tyr Ala Leu Leu Ser Asn Leu Asp Thr Phe Ser Gly Lys Leu Ser Ile
    50                  55                  60

Lys Asp Phe Leu Ser Gly Ser Pro Lys Gln Ser Gly Glu Leu Lys Gly
65                  70                  75                  80

Leu Ser Asp Glu Tyr Pro Phe Glu Lys Asp Asn Asn Pro Val Gly Asn
                85                  90                  95

Phe Ala Thr Thr Val Ser Asp Arg Ser Arg Pro Leu Asn Asp Lys Val
            100                 105                 110

Asn Glu

<210> SEQ ID NO 6
<211> LENGTH: 19
<212> TYPE: PRT
<213> ORGANISM: Artificial
<220> FEATURE:
<223> OTHER INFORMATION: Synthetic peptide

<400> SEQUENCE: 6

Ala Lys Asp Gln Asn Ala Thr Lys Val Arg Asn Leu Asn Ala Ala Arg
1               5                   10                  15

Glu Leu Phe

<210> SEQ ID NO 7
<211> LENGTH: 17
<212> TYPE: PRT
<213> ORGANISM: Artificial
<220> FEATURE:
<223> OTHER INFORMATION: Synthetic peptide

<400> SEQUENCE: 7

Val Arg Asn Lys Asp Gln Asn Ala Thr Lys Asn Ala Ala Arg Glu Leu
1               5                   10                  15

Phe

<210> SEQ ID NO 8
<211> LENGTH: 17
<212> TYPE: PRT
<213> ORGANISM: Artificial
<220> FEATURE:
<223> OTHER INFORMATION: Synthetic peptide

<400> SEQUENCE: 8

Val Arg Asn Leu Asn Ala Ala Lys Asp Gln Asn Ala Thr Lys Glu Leu
1               5                   10                  15

Phe

<210> SEQ ID NO 9
<211> LENGTH: 17
<212> TYPE: PRT
<213> ORGANISM: Artificial
<220> FEATURE:
<223> OTHER INFORMATION: Synthetic peptide

```
<400> SEQUENCE: 9

Glu Leu Phe Lys Asp Gln Asn Ala Thr Lys Asp Glu Leu Leu Ala Ala
1               5                   10                  15

Ser

<210> SEQ ID NO 10
<211> LENGTH: 13
<212> TYPE: PRT
<213> ORGANISM: Artificial
<220> FEATURE:
<223> OTHER INFORMATION: Synthetic peptide

<400> SEQUENCE: 10

Asp Glu Leu Lys Asp Gln Asn Ala Thr Lys Ala Ala Ser
1               5                   10

<210> SEQ ID NO 11
<211> LENGTH: 16
<212> TYPE: PRT
<213> ORGANISM: Artificial
<220> FEATURE:
<223> OTHER INFORMATION: Synthetic peptide

<400> SEQUENCE: 11

Asp Glu Leu Leu Ala Ala Ser Lys Asp Gln Asn Ala Thr Lys Ala Pro
1               5                   10                  15

<210> SEQ ID NO 12
<211> LENGTH: 16
<212> TYPE: PRT
<213> ORGANISM: Artificial
<220> FEATURE:
<223> OTHER INFORMATION: Synthetic peptide

<400> SEQUENCE: 12

Ala Pro Lys Asp Gln Asn Ala Thr Lys Ser Ala Glu Gln Glu Glu Leu
1               5                   10                  15

<210> SEQ ID NO 13
<211> LENGTH: 14
<212> TYPE: PRT
<213> ORGANISM: Artificial
<220> FEATURE:
<223> OTHER INFORMATION: Synthetic peptide

<400> SEQUENCE: 13

Ala Leu Leu Arg Ser Glu Lys Asp Gln Asn Ala Thr Lys Ile
1               5                   10

<210> SEQ ID NO 14
<211> LENGTH: 18
<212> TYPE: PRT
<213> ORGANISM: Artificial
<220> FEATURE:
<223> OTHER INFORMATION: Synthetic peptide

<400> SEQUENCE: 14

Ala Leu Leu Arg Ser Glu Arg Ile Lys Asp Gln Asn Ala Thr Lys Leu
1               5                   10                  15

Ala His

<210> SEQ ID NO 15
<211> LENGTH: 14
<212> TYPE: PRT
<213> ORGANISM: Artificial
```

```
<220> FEATURE:
<223> OTHER INFORMATION: Synthetic peptide

<400> SEQUENCE: 15

Leu Ala His Lys Asp Gln Asn Ala Thr Lys Gly Gln Pro Leu
1               5                   10

<210> SEQ ID NO 16
<211> LENGTH: 18
<212> TYPE: PRT
<213> ORGANISM: Artificial
<220> FEATURE:
<223> OTHER INFORMATION: Synthetic peptide

<400> SEQUENCE: 16

Gly Gln Pro Leu Lys Asp Gln Asn Ala Thr Lys Glu Ala Gln Val Leu
1               5                   10                  15

Lys Ala

<210> SEQ ID NO 17
<211> LENGTH: 15
<212> TYPE: PRT
<213> ORGANISM: Artificial
<220> FEATURE:
<223> OTHER INFORMATION: Synthetic peptide

<400> SEQUENCE: 17

Glu Ala Lys Asp Gln Asn Ala Thr Lys Val Leu Lys Ala Leu Ala
1               5                   10                  15

<210> SEQ ID NO 18
<211> LENGTH: 17
<212> TYPE: PRT
<213> ORGANISM: Artificial
<220> FEATURE:
<223> OTHER INFORMATION: Synthetic peptide

<400> SEQUENCE: 18

Val Leu Lys Ala Leu Ala Lys Asp Gln Asn Ala Thr Lys Leu Leu Ala
1               5                   10                  15

Ala

<210> SEQ ID NO 19
<211> LENGTH: 17
<212> TYPE: PRT
<213> ORGANISM: Artificial
<220> FEATURE:
<223> OTHER INFORMATION: Synthetic peptide

<400> SEQUENCE: 19

Val Leu Lys Ala Leu Ala Trp Lys Asp Gln Asn Ala Thr Lys Leu Ala
1               5                   10                  15

Ala

<210> SEQ ID NO 20
<211> LENGTH: 13
<212> TYPE: PRT
<213> ORGANISM: Artificial
<220> FEATURE:
<223> OTHER INFORMATION: Synthetic peptide

<400> SEQUENCE: 20

Leu Ala Ala Lys Asp Gln Asn Ala Thr Lys Pro Ser Ala
1               5                   10
```

```
<210> SEQ ID NO 21
<211> LENGTH: 14
<212> TYPE: PRT
<213> ORGANISM: Artificial
<220> FEATURE:
<223> OTHER INFORMATION: Synthetic peptide

<400> SEQUENCE: 21

Pro Ser Ala Lys Asp Gln Asn Ala Thr Lys Pro Gly Gln Gly
1               5                   10

<210> SEQ ID NO 22
<211> LENGTH: 14
<212> TYPE: PRT
<213> ORGANISM: Artificial
<220> FEATURE:
<223> OTHER INFORMATION: Synthetic peptide

<400> SEQUENCE: 22

Pro Ser Ala Pro Pro Lys Asp Gln Asn Ala Thr Lys Gln Gly
1               5                   10

<210> SEQ ID NO 23
<211> LENGTH: 13
<212> TYPE: PRT
<213> ORGANISM: Artificial
<220> FEATURE:
<223> OTHER INFORMATION: Synthetic peptide

<400> SEQUENCE: 23

Gln Gly Lys Asp Gln Asn Ala Thr Lys Glu Val Leu Arg
1               5                   10

<210> SEQ ID NO 24
<211> LENGTH: 13
<212> TYPE: PRT
<213> ORGANISM: Artificial
<220> FEATURE:
<223> OTHER INFORMATION: Synthetic peptide

<400> SEQUENCE: 24

Gln Gly Leu Glu Lys Asp Gln Asn Ala Thr Lys Leu Arg
1               5                   10

<210> SEQ ID NO 25
<211> LENGTH: 14
<212> TYPE: PRT
<213> ORGANISM: Artificial
<220> FEATURE:
<223> OTHER INFORMATION: Synthetic peptide

<400> SEQUENCE: 25

Leu Arg Lys Asp Gln Asn Ala Thr Lys Val Leu Gln Ala Arg
1               5                   10

<210> SEQ ID NO 26
<211> LENGTH: 13
<212> TYPE: PRT
<213> ORGANISM: Artificial
<220> FEATURE:
<223> OTHER INFORMATION: Synthetic peptide

<400> SEQUENCE: 26

Val Leu Gly Ala Arg Lys Asp Gln Asn Ala Thr Lys Gln
1               5                   10
```

<210> SEQ ID NO 27
<211> LENGTH: 18
<212> TYPE: PRT
<213> ORGANISM: Artificial
<220> FEATURE:
<223> OTHER INFORMATION: Synthetic peptide

<400> SEQUENCE: 27

Val Leu Gly Ala Arg Arg Gln Lys Asp Gln Asn Ala Thr Lys Gly Ala
1               5                   10                  15

Gln Trp

<210> SEQ ID NO 28
<211> LENGTH: 18
<212> TYPE: PRT
<213> ORGANISM: Artificial
<220> FEATURE:
<223> OTHER INFORMATION: Synthetic peptide

<400> SEQUENCE: 28

Val Leu Gln Ala Arg Arg Gln Pro Gly Lys Asp Gln Asn Ala Thr Lys
1               5                   10                  15

Gln Trp

<210> SEQ ID NO 29
<211> LENGTH: 19
<212> TYPE: PRT
<213> ORGANISM: Artificial
<220> FEATURE:
<223> OTHER INFORMATION: Synthetic peptide

<400> SEQUENCE: 29

Gln Trp Lys Asp Gln Asn Ala Thr Lys Leu Arg Glu Phe Leu Val Ser
1               5                   10                  15

Ala Tyr Phe

<210> SEQ ID NO 30
<211> LENGTH: 20
<212> TYPE: PRT
<213> ORGANISM: Artificial
<220> FEATURE:
<223> OTHER INFORMATION: Synthetic peptide

<400> SEQUENCE: 30

Leu Arg Glu Phe Leu Val Ser Ala Tyr Phe Ser Leu Lys Asp Gln Asn
1               5                   10                  15

Ala Thr Lys Gly
            20

<210> SEQ ID NO 31
<211> LENGTH: 19
<212> TYPE: PRT
<213> ORGANISM: Artificial
<220> FEATURE:
<223> OTHER INFORMATION: Synthetic peptide

<400> SEQUENCE: 31

Gly Lys Asp Gln Asn Ala Thr Lys Leu Asp Glu Asp Val Ile Gly Val
1               5                   10                  15

Tyr Lys Asp

```
<210> SEQ ID NO 32
<211> LENGTH: 20
<212> TYPE: PRT
<213> ORGANISM: Artificial
<220> FEATURE:
<223> OTHER INFORMATION: Synthetic peptide

<400> SEQUENCE: 32

Lys Asp Val Leu Gln Thr Lys Asp Gln Asn Ala Thr Lys Asp Gly Lys
1               5                   10                  15

Arg Lys Ala Leu
            20

<210> SEQ ID NO 33
<211> LENGTH: 19
<212> TYPE: PRT
<213> ORGANISM: Artificial
<220> FEATURE:
<223> OTHER INFORMATION: Synthetic peptide

<400> SEQUENCE: 33

Lys Tyr Asp Ser Val Leu Arg Asp Ile Leu Ser Ala Lys Asp Gln Asn
1               5                   10                  15

Ala Thr Lys

<210> SEQ ID NO 34
<211> LENGTH: 23
<212> TYPE: PRT
<213> ORGANISM: Artificial
<220> FEATURE:
<223> OTHER INFORMATION: Synthetic peptide

<400> SEQUENCE: 34

Met Ser Phe Lys Lys Ile Ile Lys Ala Phe Val Ile Met Ala Ala Leu
1               5                   10                  15

Val Ser Val Gln Ala His Ala
            20

<210> SEQ ID NO 35
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa represents any amino acid other than Pro
<220> FEATURE:
<221> NAME/KEY: MISC_FEATURE
<222> LOCATION: (3)..(3)
<223> OTHER INFORMATION: Xaa represents Asp or Glu
<220> FEATURE:
<221> NAME/KEY: MISC_FEATURE
<222> LOCATION: (4)..(4)
<223> OTHER INFORMATION: Xaa represents any amino acid other than Pro
<220> FEATURE:
<221> NAME/KEY: MISC_FEATURE
<222> LOCATION: (6)..(6)
<223> OTHER INFORMATION: Xaa represents any amino acid other than Pro
<220> FEATURE:
<221> NAME/KEY: MISC_FEATURE
<222> LOCATION: (7)..(7)
<223> OTHER INFORMATION: Xaa represents Ser or Thr
<220> FEATURE:
<221> NAME/KEY: MISC_FEATURE
<222> LOCATION: (8)..(8)
<223> OTHER INFORMATION: Xaa represents any amino acid other than Pro
```

<400> SEQUENCE: 35

Ala Xaa Xaa Xaa Asn Xaa Xaa Xaa Val Arg Asn Leu Asn Ala Ala Arg
1               5                   10                  15

Glu Leu Phe

<210> SEQ ID NO 36
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa represents any amino acid other than Pro
<220> FEATURE:
<221> NAME/KEY: MISC_FEATURE
<222> LOCATION: (5)..(5)
<223> OTHER INFORMATION: Xaa represents Asp or Glu
<220> FEATURE:
<221> NAME/KEY: MISC_FEATURE
<222> LOCATION: (6)..(6)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents any amino acid other than Pro
<220> FEATURE:
<221> NAME/KEY: MISC_FEATURE
<222> LOCATION: (9)..(9)
<223> OTHER INFORMATION: Xaa represents Ser or Thr
<220> FEATURE:
<221> NAME/KEY: MISC_FEATURE
<222> LOCATION: (10)..(10)
<223> OTHER INFORMATION: Xaa represents any amino acid other than Pro

<400> SEQUENCE: 36

Val Arg Asn Xaa Xaa Xaa Asn Xaa Xaa Xaa Asn Ala Ala Arg Glu Leu
1               5                   10                  15

Phe

<210> SEQ ID NO 37
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa represents any amino acid other than Pro
<220> FEATURE:
<221> NAME/KEY: MISC_FEATURE
<222> LOCATION: (9)..(9)
<223> OTHER INFORMATION: Xaa represents Asp or Glu
<220> FEATURE:
<221> NAME/KEY: MISC_FEATURE
<222> LOCATION: (10)..(10)
<223> OTHER INFORMATION: Xaa represents any amino acid other than Pro
<220> FEATURE:
<221> NAME/KEY: MISC_FEATURE
<222> LOCATION: (12)..(12)
<223> OTHER INFORMATION: Xaa represents any amino acid other than Pro
<220> FEATURE:
<221> NAME/KEY: MISC_FEATURE
<222> LOCATION: (13)..(13)
<223> OTHER INFORMATION: Xaa represents Ser or Thr
<220> FEATURE:
<221> NAME/KEY: MISC_FEATURE
<222> LOCATION: (14)..(14)
<223> OTHER INFORMATION: Xaa represents any amino acid other than Pro

<400> SEQUENCE: 37

Val Arg Asn Leu Asn Ala Ala Xaa Xaa Xaa Asn Xaa Xaa Xaa Glu Leu
1               5                   10                  15

Phe

<210> SEQ ID NO 38
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa represents any amino acid other than Pro
<220> FEATURE:
<221> NAME/KEY: MISC_FEATURE
<222> LOCATION: (5)..(5)
<223> OTHER INFORMATION: Xaa represents Asp or Glu
<220> FEATURE:
<221> NAME/KEY: MISC_FEATURE
<222> LOCATION: (6)..(6)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents any amino acid other than Pro
<220> FEATURE:
<221> NAME/KEY: MISC_FEATURE
<222> LOCATION: (9)..(9)
<223> OTHER INFORMATION: Xaa represents Ser or Thr
<220> FEATURE:
<221> NAME/KEY: MISC_FEATURE
<222> LOCATION: (10)..(10)
<223> OTHER INFORMATION: Xaa represents any amino acid other than Pro

<400> SEQUENCE: 38

Glu Leu Phe Xaa Xaa Xaa Asn Xaa Xaa Xaa Asp Glu Leu Leu Ala Ala
1               5                   10                  15

Ser

<210> SEQ ID NO 39
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa represents any amino acid other than Pro
<220> FEATURE:
<221> NAME/KEY: MISC_FEATURE
<222> LOCATION: (5)..(5)
<223> OTHER INFORMATION: Xaa represents Asp or Glu
<220> FEATURE:
<221> NAME/KEY: MISC_FEATURE
<222> LOCATION: (6)..(6)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents any amino acid other than Pro
<220> FEATURE:
<221> NAME/KEY: MISC_FEATURE
<222> LOCATION: (9)..(9)
<223> OTHER INFORMATION: Xaa represents Ser or Thr
<220> FEATURE:
<221> NAME/KEY: MISC_FEATURE
<222> LOCATION: (10)..(10)
<223> OTHER INFORMATION: Xaa represents any amino acid other than Pro

```
<400> SEQUENCE: 39

Asp Glu Leu Xaa Xaa Xaa Asn Xaa Xaa Xaa Ala Ala Ser
1               5                   10

<210> SEQ ID NO 40
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa represents any amino acid other than Pro
<220> FEATURE:
<221> NAME/KEY: MISC_FEATURE
<222> LOCATION: (9)..(9)
<223> OTHER INFORMATION: Xaa represents Asp or Glu
<220> FEATURE:
<221> NAME/KEY: MISC_FEATURE
<222> LOCATION: (10)..(10)
<223> OTHER INFORMATION: Xaa represents any amino acid other than Pro
<220> FEATURE:
<221> NAME/KEY: MISC_FEATURE
<222> LOCATION: (12)..(12)
<223> OTHER INFORMATION: Xaa represents any amino acid other than Pro
<220> FEATURE:
<221> NAME/KEY: MISC_FEATURE
<222> LOCATION: (13)..(13)
<223> OTHER INFORMATION: Xaa represents Ser or Thr
<220> FEATURE:
<221> NAME/KEY: MISC_FEATURE
<222> LOCATION: (14)..(14)
<223> OTHER INFORMATION: Xaa represents any amino acid other than Pro

<400> SEQUENCE: 40

Asp Glu Leu Leu Ala Ala Ser Xaa Xaa Xaa Asn Xaa Xaa Xaa Ala Pro
1               5                   10                  15

<210> SEQ ID NO 41
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa represents any amino acid other than Pro
<220> FEATURE:
<221> NAME/KEY: MISC_FEATURE
<222> LOCATION: (4)..(4)
<223> OTHER INFORMATION: Xaa represents Asp or Glu
<220> FEATURE:
<221> NAME/KEY: MISC_FEATURE
<222> LOCATION: (5)..(5)
<223> OTHER INFORMATION: Xaa represents any amino acid other than Pro
<220> FEATURE:
<221> NAME/KEY: MISC_FEATURE
<222> LOCATION: (7)..(7)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents Ser or Thr
<220> FEATURE:
<221> NAME/KEY: MISC_FEATURE
<222> LOCATION: (9)..(9)
<223> OTHER INFORMATION: Xaa represents any amino acid other than Pro

<400> SEQUENCE: 41

Ala Pro Xaa Xaa Xaa Asn Xaa Xaa Xaa Ser Ala Glu Gln Glu Glu Leu
1               5                   10                  15
```

```
<210> SEQ ID NO 42
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents Asp or Glu
<220> FEATURE:
<221> NAME/KEY: MISC_FEATURE
<222> LOCATION: (9)..(9)
<223> OTHER INFORMATION: Xaa represents any amino acid other than Pro
<220> FEATURE:
<221> NAME/KEY: MISC_FEATURE
<222> LOCATION: (11)..(11)
<223> OTHER INFORMATION: Xaa represents any amino acid other than Pro
<220> FEATURE:
<221> NAME/KEY: MISC_FEATURE
<222> LOCATION: (12)..(12)
<223> OTHER INFORMATION: Xaa represents Ser or Thr
<220> FEATURE:
<221> NAME/KEY: MISC_FEATURE
<222> LOCATION: (13)..(13)
<223> OTHER INFORMATION: Xaa represents any amino acid other than Pro

<400> SEQUENCE: 42

Ala Leu Leu Arg Ser Glu Xaa Xaa Xaa Asn Xaa Xaa Xaa Ile
1               5                   10

<210> SEQ ID NO 43
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa represents any amino acid other than Pro
<220> FEATURE:
<221> NAME/KEY: MISC_FEATURE
<222> LOCATION: (10)..(10)
<223> OTHER INFORMATION: Xaa represents Asp or Glu
<220> FEATURE:
<221> NAME/KEY: MISC_FEATURE
<222> LOCATION: (11)..(11)
<223> OTHER INFORMATION: Xaa represents any amino acid other than Pro
<220> FEATURE:
<221> NAME/KEY: MISC_FEATURE
<222> LOCATION: (13)..(13)
<223> OTHER INFORMATION: Xaa represents any amino acid other than Pro
<220> FEATURE:
<221> NAME/KEY: MISC_FEATURE
<222> LOCATION: (14)..(14)
<223> OTHER INFORMATION: Xaa represents Ser or Thr
<220> FEATURE:
<221> NAME/KEY: MISC_FEATURE
<222> LOCATION: (15)..(15)
<223> OTHER INFORMATION: Xaa represents any amino acid other than Pro

<400> SEQUENCE: 43

Ala Leu Leu Arg Ser Glu Arg Ile Xaa Xaa Xaa Asn Xaa Xaa Xaa Leu
1               5                   10                  15

Ala His
```

```
<210> SEQ ID NO 44
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa represents any amino acid other than Pro
<220> FEATURE:
<221> NAME/KEY: MISC_FEATURE
<222> LOCATION: (5)..(5)
<223> OTHER INFORMATION: Xaa represents Asp or Glu
<220> FEATURE:
<221> NAME/KEY: MISC_FEATURE
<222> LOCATION: (6)..(6)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents any amino acid other than Pro
<220> FEATURE:
<221> NAME/KEY: MISC_FEATURE
<222> LOCATION: (9)..(9)
<223> OTHER INFORMATION: Xaa represents Ser or Thr
<220> FEATURE:
<221> NAME/KEY: MISC_FEATURE
<222> LOCATION: (10)..(10)
<223> OTHER INFORMATION: Xaa represents any amino acid other than Pro

<400> SEQUENCE: 44

Leu Ala His Xaa Xaa Xaa Asn Xaa Xaa Xaa Gly Gln Pro Leu
1               5                   10

<210> SEQ ID NO 45
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa represents any amino acid other than Pro
<220> FEATURE:
<221> NAME/KEY: MISC_FEATURE
<222> LOCATION: (6)..(6)
<223> OTHER INFORMATION: Xaa represents Asp or Glu
<220> FEATURE:
<221> NAME/KEY: MISC_FEATURE
<222> LOCATION: (7)..(7)
<223> OTHER INFORMATION: Xaa represents any amino acid other than Pro
<220> FEATURE:
<221> NAME/KEY: MISC_FEATURE
<222> LOCATION: (9)..(9)
<223> OTHER INFORMATION: Xaa represents any amino acid other than Pro
<220> FEATURE:
<221> NAME/KEY: MISC_FEATURE
<222> LOCATION: (10)..(10)
<223> OTHER INFORMATION: Xaa represents Ser or Thr
<220> FEATURE:
<221> NAME/KEY: MISC_FEATURE
<222> LOCATION: (11)..(11)
<223> OTHER INFORMATION: Xaa represents any amino acid other than Pro

<400> SEQUENCE: 45

Gly Gln Pro Leu Xaa Xaa Xaa Asn Xaa Xaa Xaa Glu Ala Gln Val Leu
1               5                   10                  15

Lys Ala
```

```
<210> SEQ ID NO 46
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa represents any amino acid other than Pro
<220> FEATURE:
<221> NAME/KEY: MISC_FEATURE
<222> LOCATION: (4)..(4)
<223> OTHER INFORMATION: Xaa represents Asp or Glu
<220> FEATURE:
<221> NAME/KEY: MISC_FEATURE
<222> LOCATION: (5)..(5)
<223> OTHER INFORMATION: Xaa represents any amino acid other than Pro
<220> FEATURE:
<221> NAME/KEY: MISC_FEATURE
<222> LOCATION: (7)..(7)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents Ser or Thr
<220> FEATURE:
<221> NAME/KEY: MISC_FEATURE
<222> LOCATION: (9)..(9)
<223> OTHER INFORMATION: Xaa represents any amino acid other than Pro

<400> SEQUENCE: 46

Glu Ala Xaa Xaa Xaa Asn Xaa Xaa Xaa Val Leu Lys Ala Leu Ala
1               5                   10                  15

<210> SEQ ID NO 47
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents Asp or Glu
<220> FEATURE:
<221> NAME/KEY: MISC_FEATURE
<222> LOCATION: (9)..(9)
<223> OTHER INFORMATION: Xaa represents any amino acid other than Pro
<220> FEATURE:
<221> NAME/KEY: MISC_FEATURE
<222> LOCATION: (11)..(11)
<223> OTHER INFORMATION: Xaa represents any amino acid other than Pro
<220> FEATURE:
<221> NAME/KEY: MISC_FEATURE
<222> LOCATION: (12)..(12)
<223> OTHER INFORMATION: Xaa represents Ser or Thr
<220> FEATURE:
<221> NAME/KEY: MISC_FEATURE
<222> LOCATION: (13)..(13)
<223> OTHER INFORMATION: Xaa represents any amino acid other than Pro

<400> SEQUENCE: 47

Val Leu Lys Ala Leu Ala Xaa Xaa Xaa Asn Xaa Xaa Xaa Leu Leu Ala
1               5                   10                  15

Ala
```

```
<210> SEQ ID NO 48
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa represents any amino acid other than Pro
<220> FEATURE:
<221> NAME/KEY: MISC_FEATURE
<222> LOCATION: (9)..(9)
<223> OTHER INFORMATION: Xaa represents Asp or Glu
<220> FEATURE:
<221> NAME/KEY: MISC_FEATURE
<222> LOCATION: (10)..(10)
<223> OTHER INFORMATION: Xaa represents any amino acid other than Pro
<220> FEATURE:
<221> NAME/KEY: MISC_FEATURE
<222> LOCATION: (12)..(12)
<223> OTHER INFORMATION: Xaa represents any amino acid other than Pro
<220> FEATURE:
<221> NAME/KEY: MISC_FEATURE
<222> LOCATION: (13)..(13)
<223> OTHER INFORMATION: Xaa represents Ser or Thr
<220> FEATURE:
<221> NAME/KEY: MISC_FEATURE
<222> LOCATION: (14)..(14)
<223> OTHER INFORMATION: Xaa represents any amino acid other than Pro

<400> SEQUENCE: 48

Val Leu Lys Ala Leu Ala Trp Xaa Xaa Xaa Asn Xaa Xaa Xaa Leu Ala
1               5                   10                  15

Ala

<210> SEQ ID NO 49
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa represents any amino acid other than Pro
<220> FEATURE:
<221> NAME/KEY: MISC_FEATURE
<222> LOCATION: (5)..(5)
<223> OTHER INFORMATION: Xaa represents Asp or Glu
<220> FEATURE:
<221> NAME/KEY: MISC_FEATURE
<222> LOCATION: (6)..(6)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents any amino acid other than Pro
<220> FEATURE:
<221> NAME/KEY: MISC_FEATURE
<222> LOCATION: (9)..(9)
<223> OTHER INFORMATION: Xaa represents Ser or Thr
<220> FEATURE:
<221> NAME/KEY: MISC_FEATURE
<222> LOCATION: (10)..(10)
<223> OTHER INFORMATION: Xaa represents any amino acid other than Pro

<400> SEQUENCE: 49

Leu Ala Ala Xaa Xaa Xaa Asn Xaa Xaa Xaa Pro Ser Ala
1               5                   10
```

```
<210> SEQ ID NO 50
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa represents any amino acid other than Pro
<220> FEATURE:
<221> NAME/KEY: MISC_FEATURE
<222> LOCATION: (5)..(5)
<223> OTHER INFORMATION: Xaa represents Asp or Glu
<220> FEATURE:
<221> NAME/KEY: MISC_FEATURE
<222> LOCATION: (6)..(6)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents any amino acid other than Pro
<220> FEATURE:
<221> NAME/KEY: MISC_FEATURE
<222> LOCATION: (9)..(9)
<223> OTHER INFORMATION: Xaa represents Ser or Thr
<220> FEATURE:
<221> NAME/KEY: MISC_FEATURE
<222> LOCATION: (10)..(10)
<223> OTHER INFORMATION: Xaa represents any amino acid other than Pro

<400> SEQUENCE: 50

Pro Ser Ala Xaa Xaa Xaa Asn Xaa Xaa Xaa Pro Gly Gln Gly
1               5                   10

<210> SEQ ID NO 51
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa represents any amino acid other than Pro
<220> FEATURE:
<221> NAME/KEY: MISC_FEATURE
<222> LOCATION: (7)..(7)
<223> OTHER INFORMATION: Xaa represents Asp or Glu
<220> FEATURE:
<221> NAME/KEY: MISC_FEATURE
<222> LOCATION: (8)..(8)
<223> OTHER INFORMATION: Xaa represents any amino acid other than Pro
<220> FEATURE:
<221> NAME/KEY: MISC_FEATURE
<222> LOCATION: (10)..(10)
<223> OTHER INFORMATION: Xaa represents any amino acid other than Pro
<220> FEATURE:
<221> NAME/KEY: MISC_FEATURE
<222> LOCATION: (11)..(11)
<223> OTHER INFORMATION: Xaa represents Ser or Thr
<220> FEATURE:
<221> NAME/KEY: MISC_FEATURE
<222> LOCATION: (12)..(12)
<223> OTHER INFORMATION: Xaa represents any amino acid other than Pro

<400> SEQUENCE: 51

Pro Ser Ala Pro Pro Xaa Xaa Xaa Asn Xaa Xaa Xaa Gln Gly
1               5                   10

<210> SEQ ID NO 52
<211> LENGTH: 13
<212> TYPE: PRT
<213> ORGANISM: Artificial
```

```
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa represents any amino acid other than Pro
<220> FEATURE:
<221> NAME/KEY: MISC_FEATURE
<222> LOCATION: (4)..(4)
<223> OTHER INFORMATION: Xaa represents Asp or Glu
<220> FEATURE:
<221> NAME/KEY: MISC_FEATURE
<222> LOCATION: (5)..(5)
<223> OTHER INFORMATION: Xaa represents any amino acid other than Pro
<220> FEATURE:
<221> NAME/KEY: MISC_FEATURE
<222> LOCATION: (7)..(7)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents Ser or Thr
<220> FEATURE:
<221> NAME/KEY: MISC_FEATURE
<222> LOCATION: (9)..(9)
<223> OTHER INFORMATION: Xaa represents any amino acid other than Pro

<400> SEQUENCE: 52

Gln Gly Xaa Xaa Xaa Asn Xaa Xaa Xaa Glu Val Leu Arg
1               5                   10

<210> SEQ ID NO 53
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa represents any amino acid other than Pro
<220> FEATURE:
<221> NAME/KEY: MISC_FEATURE
<222> LOCATION: (6)..(6)
<223> OTHER INFORMATION: Xaa represents Asp or Glu
<220> FEATURE:
<221> NAME/KEY: MISC_FEATURE
<222> LOCATION: (7)..(7)
<223> OTHER INFORMATION: Xaa represents any amino acid other than Pro
<220> FEATURE:
<221> NAME/KEY: MISC_FEATURE
<222> LOCATION: (9)..(9)
<223> OTHER INFORMATION: Xaa represents any amino acid other than Pro
<220> FEATURE:
<221> NAME/KEY: MISC_FEATURE
<222> LOCATION: (10)..(10)
<223> OTHER INFORMATION: Xaa represents Ser or Thr
<220> FEATURE:
<221> NAME/KEY: MISC_FEATURE
<222> LOCATION: (11)..(11)
<223> OTHER INFORMATION: Xaa represents any amino acid other than Pro

<400> SEQUENCE: 53

Gln Gly Leu Glu Xaa Xaa Xaa Asn Xaa Xaa Xaa Leu Arg
1               5                   10

<210> SEQ ID NO 54
<211> LENGTH: 14
<212> TYPE: PRT
<213> ORGANISM: Artificial
<220> FEATURE:
<223> OTHER INFORMATION: Synthetic peptide
```

```
<220> FEATURE:
<221> NAME/KEY: MISC_FEATURE
<222> LOCATION: (3)..(3)
<223> OTHER INFORMATION: Xaa represents any amino acid other than Pro
<220> FEATURE:
<221> NAME/KEY: MISC_FEATURE
<222> LOCATION: (4)..(4)
<223> OTHER INFORMATION: Xaa represents Asp or Glu
<220> FEATURE:
<221> NAME/KEY: MISC_FEATURE
<222> LOCATION: (5)..(5)
<223> OTHER INFORMATION: Xaa represents any amino acid other than Pro
<220> FEATURE:
<221> NAME/KEY: MISC_FEATURE
<222> LOCATION: (7)..(7)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents Ser or Thr
<220> FEATURE:
<221> NAME/KEY: MISC_FEATURE
<222> LOCATION: (9)..(9)
<223> OTHER INFORMATION: Xaa represents any amino acid other than Pro

<400> SEQUENCE: 54

Leu Arg Xaa Xaa Xaa Asn Xaa Xaa Xaa Val Leu Gln Ala Arg
1               5                   10

<210> SEQ ID NO 55
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa represents any amino acid other than Pro
<220> FEATURE:
<221> NAME/KEY: MISC_FEATURE
<222> LOCATION: (7)..(7)
<223> OTHER INFORMATION: Xaa represents Asp or Glu
<220> FEATURE:
<221> NAME/KEY: MISC_FEATURE
<222> LOCATION: (8)..(8)
<223> OTHER INFORMATION: Xaa represents any amino acid other than Pro
<220> FEATURE:
<221> NAME/KEY: MISC_FEATURE
<222> LOCATION: (10)..(10)
<223> OTHER INFORMATION: Xaa represents any amino acid other than Pro
<220> FEATURE:
<221> NAME/KEY: MISC_FEATURE
<222> LOCATION: (11)..(11)
<223> OTHER INFORMATION: Xaa represents Ser or Thr
<220> FEATURE:
<221> NAME/KEY: MISC_FEATURE
<222> LOCATION: (12)..(12)
<223> OTHER INFORMATION: Xaa represents any amino acid other than Pro

<400> SEQUENCE: 55

Val Leu Gly Ala Arg Xaa Xaa Xaa Asn Xaa Xaa Xaa Gln
1               5                   10

<210> SEQ ID NO 56
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa represents any amino acid other than Pro
```

```
<220> FEATURE:
<221> NAME/KEY: MISC_FEATURE
<222> LOCATION: (9)..(9)
<223> OTHER INFORMATION: Xaa represents Asp or Glu
<220> FEATURE:
<221> NAME/KEY: MISC_FEATURE
<222> LOCATION: (10)..(10)
<223> OTHER INFORMATION: Xaa represents any amino acid other than Pro
<220> FEATURE:
<221> NAME/KEY: MISC_FEATURE
<222> LOCATION: (12)..(12)
<223> OTHER INFORMATION: Xaa represents any amino acid other than Pro
<220> FEATURE:
<221> NAME/KEY: MISC_FEATURE
<222> LOCATION: (13)..(13)
<223> OTHER INFORMATION: Xaa represents Ser or Thr
<220> FEATURE:
<221> NAME/KEY: MISC_FEATURE
<222> LOCATION: (14)..(14)
<223> OTHER INFORMATION: Xaa represents any amino acid other than Pro

<400> SEQUENCE: 56

Val Leu Gly Ala Arg Arg Gln Xaa Xaa Xaa Asn Xaa Xaa Xaa Gly Ala
1               5                   10                  15

Gln Trp

<210> SEQ ID NO 57
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: Xaa represents any amino acid other than Pro
<220> FEATURE:
<221> NAME/KEY: MISC_FEATURE
<222> LOCATION: (11)..(11)
<223> OTHER INFORMATION: Xaa represents Asp or Glu
<220> FEATURE:
<221> NAME/KEY: MISC_FEATURE
<222> LOCATION: (12)..(12)
<223> OTHER INFORMATION: Xaa represents any amino acid other than Pro
<220> FEATURE:
<221> NAME/KEY: MISC_FEATURE
<222> LOCATION: (14)..(14)
<223> OTHER INFORMATION: Xaa represents any amino acid other than Pro
<220> FEATURE:
<221> NAME/KEY: MISC_FEATURE
<222> LOCATION: (15)..(15)
<223> OTHER INFORMATION: Xaa represents Ser or Thr
<220> FEATURE:
<221> NAME/KEY: MISC_FEATURE
<222> LOCATION: (16)..(16)
<223> OTHER INFORMATION: Xaa represents any amino acid other than Pro

<400> SEQUENCE: 57

Val Leu Gln Ala Arg Arg Gln Pro Gly Xaa Xaa Xaa Asn Xaa Xaa Xaa
1               5                   10                  15

Gln Trp

<210> SEQ ID NO 58
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa represents any amino acid other than Pro
```

```
<220> FEATURE:
<221> NAME/KEY: MISC_FEATURE
<222> LOCATION: (4)..(4)
<223> OTHER INFORMATION: Xaa represents Asp or Glu
<220> FEATURE:
<221> NAME/KEY: MISC_FEATURE
<222> LOCATION: (5)..(5)
<223> OTHER INFORMATION: Xaa represents any amino acid other than Pro
<220> FEATURE:
<221> NAME/KEY: MISC_FEATURE
<222> LOCATION: (7)..(7)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents Ser or Thr
<220> FEATURE:
<221> NAME/KEY: MISC_FEATURE
<222> LOCATION: (9)..(9)
<223> OTHER INFORMATION: Xaa represents any amino acid other than Pro

<400> SEQUENCE: 58

Gln Trp Xaa Xaa Xaa Asn Xaa Xaa Xaa Leu Arg Glu Phe Leu Val Ser
1               5                   10                  15

Ala Tyr Phe

<210> SEQ ID NO 59
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: Xaa represents any amino acid other than Pro
<220> FEATURE:
<221> NAME/KEY: MISC_FEATURE
<222> LOCATION: (14)..(14)
<223> OTHER INFORMATION: Xaa represents Asp or Glu
<220> FEATURE:
<221> NAME/KEY: MISC_FEATURE
<222> LOCATION: (15)..(15)
<223> OTHER INFORMATION: Xaa represents any amino acid other than Pro
<220> FEATURE:
<221> NAME/KEY: MISC_FEATURE
<222> LOCATION: (17)..(17)
<223> OTHER INFORMATION: Xaa represents any amino acid other than Pro
<220> FEATURE:
<221> NAME/KEY: MISC_FEATURE
<222> LOCATION: (18)..(18)
<223> OTHER INFORMATION: Xaa represents Ser or Thr
<220> FEATURE:
<221> NAME/KEY: MISC_FEATURE
<222> LOCATION: (19)..(19)
<223> OTHER INFORMATION: Xaa represents any amino acid other than Pro

<400> SEQUENCE: 59

Leu Arg Glu Phe Leu Val Ser Ala Tyr Phe Ser Leu Xaa Xaa Xaa Asn
1               5                   10                  15

Xaa Xaa Xaa Gly
            20

<210> SEQ ID NO 60
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa represents any amino acid other than Pro
```

```
<220> FEATURE:
<221> NAME/KEY: MISC_FEATURE
<222> LOCATION: (3)..(3)
<223> OTHER INFORMATION: Xaa represents Asp or Glu
<220> FEATURE:
<221> NAME/KEY: MISC_FEATURE
<222> LOCATION: (4)..(4)
<223> OTHER INFORMATION: Xaa represents any amino acid other than Pro
<220> FEATURE:
<221> NAME/KEY: MISC_FEATURE
<222> LOCATION: (6)..(6)
<223> OTHER INFORMATION: Xaa represents any amino acid other than Pro
<220> FEATURE:
<221> NAME/KEY: MISC_FEATURE
<222> LOCATION: (7)..(7)
<223> OTHER INFORMATION: Xaa represents Ser or Thr
<220> FEATURE:
<221> NAME/KEY: MISC_FEATURE
<222> LOCATION: (8)..(8)
<223> OTHER INFORMATION: Xaa represents any amino acid other than Pro

<400> SEQUENCE: 60

Gly Xaa Xaa Xaa Asn Xaa Xaa Xaa Leu Asp Glu Asp Val Ile Gly Val
1               5                   10                  15

Tyr Lys Asp

<210> SEQ ID NO 61
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa represents any amino acid other than Pro
<220> FEATURE:
<221> NAME/KEY: MISC_FEATURE
<222> LOCATION: (8)..(8)
<223> OTHER INFORMATION: Xaa represents Asp or Glu
<220> FEATURE:
<221> NAME/KEY: MISC_FEATURE
<222> LOCATION: (9)..(9)
<223> OTHER INFORMATION: Xaa represents any amino acid other than Pro
<220> FEATURE:
<221> NAME/KEY: MISC_FEATURE
<222> LOCATION: (11)..(11)
<223> OTHER INFORMATION: Xaa represents any amino acid other than Pro
<220> FEATURE:
<221> NAME/KEY: MISC_FEATURE
<222> LOCATION: (12)..(12)
<223> OTHER INFORMATION: Xaa represents Ser or Thr
<220> FEATURE:
<221> NAME/KEY: MISC_FEATURE
<222> LOCATION: (13)..(13)
<223> OTHER INFORMATION: Xaa represents any amino acid other than Pro

<400> SEQUENCE: 61

Lys Asp Val Leu Gln Thr Xaa Xaa Xaa Asn Xaa Xaa Xaa Asp Gly Lys
1               5                   10                  15

Arg Lys Ala Leu
            20

<210> SEQ ID NO 62
<211> LENGTH: 19
<212> TYPE: PRT
<213> ORGANISM: Artificial
<220> FEATURE:
<223> OTHER INFORMATION: Synthetic peptide
```

```
<400> SEQUENCE: 62

Lys Tyr Asp Ser Val Leu Arg Asp Ile Leu Ser Ala Lys Asp Gln Asn
1               5                   10                  15

Ala Thr Lys

<210> SEQ ID NO 63
<211> LENGTH: 23
<212> TYPE: PRT
<213> ORGANISM: Artificial
<220> FEATURE:
<223> OTHER INFORMATION: Synthetic peptide

<400> SEQUENCE: 63

Met Ser Phe Lys Lys Ile Ile Lys Ala Phe Val Ile Met Ala Ala Leu
1               5                   10                  15

Val Ser Val Gln Ala His Ala
            20

<210> SEQ ID NO 64
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa represents Asp or Glu
<220> FEATURE:
<221> NAME/KEY: MISC_FEATURE
<222> LOCATION: (2)..(2)
<223> OTHER INFORMATION: Xaa represents any amino acid other than Pro
<220> FEATURE:
<221> NAME/KEY: MISC_FEATURE
<222> LOCATION: (4)..(4)
<223> OTHER INFORMATION: Xaa represents any amino acid other than Pro
<220> FEATURE:
<221> NAME/KEY: MISC_FEATURE
<222> LOCATION: (5)..(5)
<223> OTHER INFORMATION: Xaa represents Ser or Thr

<400> SEQUENCE: 64

Xaa Xaa Asn Xaa Xaa
1               5

<210> SEQ ID NO 65
<211> LENGTH: 558
<212> TYPE: PRT
<213> ORGANISM: Pseudomonas aeruginosa

<400> SEQUENCE: 65

Met Ser Trp Gln Leu Phe Ser Glu Lys Cys Arg Phe Leu Gly Ala Val
1               5                   10                  15

Glu Ile Ser Gln His Phe Trp Gly Phe Ile Val Leu Glu Ala Ser Phe
            20                  25                  30

Gly Met Lys Ile Lys Ala Ala Leu Ile Val Asp Asp Leu Ser Leu Ser
        35                  40                  45

Glu Trp Gln Lys Arg Ala Ile Glu Asp Ser Ser Glu Tyr Leu Asp Ile
    50                  55                  60

Gln Leu Val Leu Ser Cys Arg Asn Ser Ala Thr Lys Lys Ser Val Ile
65                  70                  75                  80

Lys His Cys Gly Tyr Tyr Phe Leu Asn Ile Leu Ser Leu Lys Asn Asp
                85                  90                  95
```

```
Met Thr Arg Arg Val Gln Leu Asp Ser Arg Gly Ser Glu Val Ile His
            100                 105                 110
Phe Asp Ser Asp Tyr Glu Gly Ala Trp Gln Arg Ile Pro Glu Asp Val
            115                 120                 125
Cys Ala Arg Ile Leu Asp Lys Gly Ile Lys Leu Val Ile Lys Phe Gly
            130                 135                 140
Met Ser Leu Leu Arg Ile Asp Gly Gly Leu Gln Arg Leu Asp Ile Leu
145                 150                 155                 160
Ser Tyr His His Gly Asp Pro Glu Tyr Tyr Arg Gly Arg Pro Ala Gly
                165                 170                 175
Phe Tyr Glu Ile Tyr Glu Asn Ala Asp Ser Val Gly Ile Ile Val Gln
            180                 185                 190
Lys Leu Ser Asn Lys Leu Asp Ala Gly Glu Val Leu Val Arg Gly Tyr
            195                 200                 205
Ser Lys Val His His Ser Tyr Lys Lys Thr Ser Arg Asn Phe Tyr
            210                 215                 220
Leu Asn Ser Val Val Leu Leu Arg Lys Ala Leu Val Asn Tyr Ser Arg
225                 230                 235                 240
Gly Glu Gln Val Val Leu Glu Lys Leu Gly Lys Asn Tyr Arg Leu Pro
            245                 250                 255
Ser Asn Phe Thr Val Phe Lys Phe Phe Cys Lys Thr Ile Phe Arg Gly
            260                 265                 270
Leu Ala Arg Leu Ser Tyr Gly Ala Phe Phe Glu Lys Lys Trp Asn Val
            275                 280                 285
Val Ala Leu Pro Tyr Asn Asp Ile Pro Ser Leu Gln Glu Leu Ser Val
            290                 295                 300
Ser Ala Gly Lys Ile Pro Lys Val Glu Lys Gly Tyr Thr Phe Tyr Ala
305                 310                 315                 320
Asp Pro Phe Phe Ser Ala Asp Gly Lys Leu Ile Arg Leu Glu Ala Leu
            325                 330                 335
Asn Ala Ser Asn Gly Leu Gly Glu Ile Ile Glu Leu Lys Ala Gln Ser
            340                 345                 350
Leu Asp Phe Ser Arg Val Ile Leu Lys Gly Asn His Phe Ser Tyr Pro
            355                 360                 365
Tyr Ser Phe Glu Ala Ser Gly Val Glu Tyr Leu Ile Pro Glu Val Ala
            370                 375                 380
Ser His Ser Ala Pro Cys Leu Leu Pro Pro Phe Ala Leu Glu Ser
385                 390                 395                 400
Lys Lys Leu Phe Gln Gly Met Glu Gly Glu Arg Ile Leu Asp Gly Thr
            405                 410                 415
Leu Phe Glu His Gly Gly Arg Tyr Tyr Leu Phe Cys Gly Gln Ala Val
            420                 425                 430
Ser Gly Ser Asp Asn Leu Tyr Leu Tyr Val Gly Glu Ser Leu Glu Gly
            435                 440                 445
Pro Tyr Thr Ser His Pro Cys Asn Pro Val Val Met Asn Pro Gly Ser
            450                 455                 460
Ala Arg Met Gly Gly Arg Ile Phe Lys Glu Gly Lys Leu Tyr Arg
465                 470                 475                 480
Phe Gly Gln Asn Asn Ser Tyr Gly Tyr Gly Ser Ser Leu Ala Val Asn
            485                 490                 495
Glu Ile Glu Val Leu Asp Pro Glu His Tyr Ser Glu Lys Arg Val Ala
            500                 505                 510
```

```
Asn Leu Ala Phe Gln Asp Ala Arg Gly Pro His Thr Ile Asp Ile His
        515                 520                 525

Gly Gln Thr Met Ile Leu Asp Phe Tyr Gln Arg Phe Ser Leu Leu
    530                 535                 540

Ala Gly Tyr Arg Arg Leu Val Ala Arg Leu Leu Ser Arg Gly
545                 550                 555

<210> SEQ ID NO 66
<211> LENGTH: 417
<212> TYPE: PRT
<213> ORGANISM: Pseudomonas aeruginosa

<400> SEQUENCE: 66

Met Tyr Ala Met Leu Thr Gly Ala Thr Leu Leu Ile Phe Ala Val Ala
1               5                   10                  15

Ala Arg Leu Leu Ala Arg Ser Ala Ile His Pro Ser Val Ala Met Pro
            20                  25                  30

Ile Thr Trp Gly Leu Gly Leu Ile Gly Val Ser Leu Ala Ser Leu Ile
        35                  40                  45

Gly Phe Tyr Arg Val Glu Ser Asp Ala Leu Ile Phe Leu Phe Gly
    50                  55                  60

Val Met Ser Phe Ser Leu Ser Ala Gly Cys Phe Ser Phe Leu Tyr Asn
65                  70                  75                  80

Gly Tyr Phe Arg Ala Pro Ser Ser Asn Phe Leu Phe Asp Ser Glu Leu
                85                  90                  95

Arg Thr Arg Ala Leu Val Ile Phe Phe Cys Leu Ala His Ile Val Phe
            100                 105                 110

Leu Thr Val Ile Tyr Arg Asp Leu Ser Ser Ile Ala Pro Thr Leu Arg
        115                 120                 125

Glu Ala Ala Tyr Met Ala Arg Ala Gln Ser Val Ser Gly Glu Pro Val
    130                 135                 140

Leu Ser Ser Leu Ser Met Asn Tyr Leu Gln Leu Gly Gln Thr Val Ile
145                 150                 155                 160

Pro Leu Val Val Leu Leu Tyr Leu Arg Gly Lys Cys Gly Val Leu Gly
                165                 170                 175

Phe Leu Ala Ile Ser Val Pro Trp Met Gly Val Ile Leu Leu Ala Ser
            180                 185                 190

Gly Arg Ala Ser Leu Met Gln Met Leu Val Gly Leu Phe Phe Ile Tyr
        195                 200                 205

Ile Leu Val Lys Gly Ser Pro Ser Leu Lys Ser Leu Leu Val Ile Gly
    210                 215                 220

Leu Ala Met Phe Leu Val Ile Ala Val Gly Ala Val Ala Thr Ser Lys
225                 230                 235                 240

Ile Gln Phe His Glu Gly Asp Gly Ile Ser Thr Leu Phe Ile Glu Leu
                245                 250                 255

Tyr Arg His Val Ala Gly Tyr Ala Leu Gln Gly Pro Val Leu Phe Asp
            260                 265                 270

Arg Tyr Tyr Gln Gly Ser Ile His Leu Glu Pro Tyr Trp Ser Pro Leu
        275                 280                 285

Asn Gly Phe Cys Ser Ile Leu Ala Thr Val Gly Leu Cys Gln Lys Pro
    290                 295                 300

Pro Leu His Leu Asp Phe Tyr Glu Tyr Ala Pro Gly Glu Leu Gly Asn
305                 310                 315                 320

Val Tyr Ser Met Phe Phe Ser Met Tyr Pro His Tyr Gly Ala Leu Gly
                325                 330                 335
```

```
Val Ile Gly Val Met Ala Leu Tyr Gly Met Leu Cys Ser Tyr Ala Tyr
                340                 345                 350

Cys Lys Ala Lys Lys Gly Ser Leu Tyr Phe Thr Val Leu Ser Ser Tyr
            355                 360                 365

Leu Phe Ser Ala Ile Val Phe Ser Leu Phe Ser Asp Gln Ile Ser Thr
        370                 375                 380

Ser Trp Trp Phe Tyr Val Lys Met Thr Ile Ile Leu Gly Ile Leu Cys
385                 390                 395                 400

Phe Val Phe Arg Arg Asp Arg Met Phe Val Ile Arg Leu Pro Gln Ala
                405                 410                 415

Gly

<210> SEQ ID NO 67
<211> LENGTH: 885
<212> TYPE: DNA
<213> ORGANISM: Pseudomonas aeruginosa

<400> SEQUENCE: 67
atggaagtca gaaaccttaa tgccgctcgc gagctgttcc tggacgagct cctggccgcg      60
tcggcggcgc ctgccagtgc cgagcaggag gaactgctgg ccctgttgcg cagcgagcgg     120
atcgtgctgg cccacgccgg ccagccgctg agcgaggcgc aagtgctcaa ggcgctcgcc     180
tggttgctcg cggccaatcc gtccgcgcct ccggggcagg gctcgaggt actccgcgaa      240 gtcctgcagg cacgtcggca gcccggtgcg cagtgggatc tgcgcgagtt cctggtgtcg     300
gcctatttca gcctgcacgg gcgtctcgac gaggatgtca tcggtgtcta caaggatgtc     360
ctgcagaccc aggacggcaa gcgcaaggcg ctgctcgacg agctcaaggc gctgaccgcg     420
gagttgaagg tctacagcgt gatccagtcg cagatcaacg ccgcgctgtc ggccaagcag     480
ggcatcagga tcgacgctgg cggtatcgat ctggtcgacc ccacgctata tggctatgcc     540
gtcggcgatc ccaggtggaa ggacagcccc gagtatgcgc tgctgagcaa tctggatacc     600
ttcagcggca agctgtcgat caaggatttt ctcagcggct cgccgaagca gagcggggaa     660
ctcaagggcc tcagcgatga gtacccctc gagaaggaca caacccggt cggcaatttc      720 gccaccacgg tgagcgaccg ctcgcgtccg ctgaacgaca aggtcaacga aagaccacc     780 ctgctcaacg acaccagctc ccgctacaac tcggcggtcg aggcgctcaa ccgcttcatt     840
cagaaatacg acagcgtcct gcgcgacatt ctcagcgcga tctag                    885

<210> SEQ ID NO 68
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa represents any amino acid other than Pro
<220> FEATURE:
<221> NAME/KEY: MISC_FEATURE
<222> LOCATION: (2)..(2)
<223> OTHER INFORMATION: Xaa represents Asp or Glu
<220> FEATURE:
<221> NAME/KEY: MISC_FEATURE
<222> LOCATION: (3)..(3)
<223> OTHER INFORMATION: Xaa represents any amino acid other than Pro
<220> FEATURE:
<221> NAME/KEY: MISC_FEATURE
<222> LOCATION: (5)..(5)
<223> OTHER INFORMATION: Xaa represents any amino acid other than Pro
```

```
<220> FEATURE:
<221> NAME/KEY: MISC_FEATURE
<222> LOCATION: (6)..(6)
<223> OTHER INFORMATION: Xaa represents Ser or Thr
<220> FEATURE:
<221> NAME/KEY: MISC_FEATURE
<222> LOCATION: (7)..(7)
<223> OTHER INFORMATION: Xaa represents any amino acid other than Pro

<400> SEQUENCE: 68

Xaa Xaa Xaa Asn Xaa Xaa Xaa
1               5
```